US006641614B1

(12) United States Patent
Wagner et al.

(10) Patent No.: US 6,641,614 B1
(45) Date of Patent: *Nov. 4, 2003

(54) MULTI-VARIABLE-HEIGHT FUSION DEVICE

(75) Inventors: Erik J. Wagner, Austin, TX (US); Michael C. Dinsdale, Richardson, TX (US)

(73) Assignee: Spinal Concepts, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/046,759

(22) Filed: Mar. 24, 1998

Related U.S. Application Data

(63) Continuation-in-part of application No. 08/847,172, filed on May 1, 1997.

(51) Int. Cl.[7] ................................................. A61F 2/44
(52) U.S. Cl. ................................................. 623/17.15
(58) Field of Search ........................... 623/17.15, 17.16, 623/17.11; 606/61

(56) References Cited

U.S. PATENT DOCUMENTS

| 5,522,899 A | * | 6/1996 | Michelson | 623/17 |
| 5,653,763 A | * | 8/1997 | Errico et al. | 623/17.11 |
| 5,782,832 A | | 7/1998 | Larsen et al. | |
| 6,045,579 A | * | 4/2000 | Hochshuler et al. | 623/17.16 |

FOREIGN PATENT DOCUMENTS

| DE | 4323956 C | 10/1994 |
| EP | 0260044 A | 3/1988 |
| EP | WO 88/03781 | 6/1988 |
| EP | 0578320 A1 | 1/1994 |
| EP | 0778007 A1 | 6/1997 |
| FR | 2717068 | 9/1995 |
| FR | 2732887 A1 | 10/1996 |
| FR | 2736535 A1 | 1/1997 |
| SU | 1424826 A | 9/1988 |
| WO | WO 97/00054 | 1/1997 |
| WO | 97/06753 A | 2/1997 |
| WO | WO 98/14142 | 4/1998 |

OTHER PUBLICATIONS

Danek Group, Inc. Medical Division Publication entitled, "TSRH Spinal System—Unmatched versatility," 1992, pp. 1–4.
Danek Surgical Technique Manual entitled, "TSRH Spinal Implant System," Date Unknown, pp. 1–16.
Danek Surgical Technique Manual entitled, "TSRH Crosslink," Date Unknown, pp. 1–8.
Dickman Curtis A., et al., BNI Quarterly Publication entitled, "Techniques of Screw Fixation of the Cervical Spine," vol. 9. No. 4, Fall 1993, pp. 27–39.
Slone et al., RadioGraphics Publication entitled, "Spinal Fixation," vol. 13 No. 2, Mar. 1993, pp. 341–356.
Synthes Spine Publication entitled, "The Universal Spinal System—Internal Fixation for the Spine," 1994, pp. 1–15.

(List continued on next page.)

*Primary Examiner*—Bruce Snow
(74) *Attorney, Agent, or Firm*—Meyertons, Hood, Kivlin, Kowert & Goetzel, P.C.; Eric B. Meyertons

(57) ABSTRACT

Method and apparatus for promoting a spinal fusion between neighboring vertebrae are disclosed. Apparatus may be located within the intervertebral disc space and preferably includes a pair of engaging plates for contacting the vertebrae. An alignment device may be used to alter the vertical height between the engaging plates to customize the apparatus to fit a given patient. In one embodiment, the alignment device includes two turnbuckles and two pairs of cam blocks for adjusting the height between the engaging plates.

41 Claims, 39 Drawing Sheets

OTHER PUBLICATIONS

AcroMed Publication entitled, "The ISOLA Spinal System—Versatility, simplicity and minimal profile in the surgical treatment of the spine," 1994, pp. 1–15.

AcroMed Corporation Publication entitled "ISOLA® Transverse Rod Connectors: Principles and Techniques," Date Unknown, pp. I,ii,1–8.

Danek Publication entitled, "AXIS—Fixation System," 1993, pp. 1–6.

Synthes Publication entitled, "Small Notched Titanium Reconstruction Plate System," 1996, pp. 1–6.

J. Neurosurg Publication entitled, "Posterior plates in the management of cervical instability: long–term results in 44 patients," vol. 81, 1994, pp. 341–349.

BNI Quarterly Publication entitled, "Lateral Mass Posterior Plating and Facet Fusion for Cervical Spine Instability," vol. 7, No. 2, 1991, pp. i,ii, 1–12.

Beadling, Lee, Orthopedics Today Publication entitled, "FDA Clears Spinal Cages for Interbody Lumbar Fusion," pp. 1–2.

MedPro Month Publication entitled, "Trends in Spine & Disk Surgery," vol. VI, No. 11–12, pp. 280–284.

Surgical Dynamics Ray Threaded Fusion Cage Device Surgical Technique Manual, pp. 1–10.

Surgical Dynamics Ray Threaded Fusion Cage, pp. 1–6.

AcroMed Publication entitled, "AcroMed Spinal Solutions for Cervical Pathologies," 07–95, pp. 1–8.

Codman Publication entitled, "Sof'wire Cable System," 6 pp.

Huhn, Stephen L. et al., "Posterior Spinal Osteosynthesis for Cervical Fracture/Dislocation Using a Flexible Multistrand Cable System: Technical Note," Neurosurgery, vol. 29, No. 6, 1991, pp. 943–946.

Dickman, Curtis A. et al., "Wire Fixation for the Cervical Spine: Biomechanical Principles and Surgical Techniques," BNI Quarterly, vol. 9, No. 4, Fall 1993, pp. 2–16.

Publication by AcroMed entitled, "ACROMED Cable System by Songer," 9/93, 4 pp.

M. Aebi, MD, et al., "Treatment of Cervical Spine Injuries with Anterior Plating: Indications, Techniques, and Results," vol. 16, No. 3S, Mar., 1991 Supplement, pp. S38–S45.

Foley, M.D. et al., "Aline Anterior Cervical Plating System," Smith & Nephew Richards, Inc. Orthopaedics Catalog Information, 9/96, pp. 1–16.

Lowery, Gary L., M.D., Ph.D., Sofamor Danek Group, Inc. Publication entitled, "Orion Anterior Cervical Plate System: Surgical Technique," 1994, pp. 1–24.

Apfelbaum, R., M.D., Aesculap Scientific Information publication entitled, "Posterior Transarticular C1–2 Screw Fixation for Atlantoaxial Instability," 1993, pp. 1–15.

Danek Titanium Cable System publication by Danek Group, Inc., 1994, 6.pp.

Publication entitled, "Spinal Disorders", 4 pp.

O'Brien, John P., Ph.D., Orthopaedic Product News Article entitled, "Interbody Fusion of the Lumbar Spine," pp. 1–3.

Roy et al., "Variation of Young's Modulus and Hardness in Human Lumbar Vertebrae Measured by Nanoindentation", pp. 1–4.

Sofamor Danek publication entitled, "Atlas Cable System: Evolution of the Cable System for Spinal Applications," 1995, 2 pp.

AcroMed Publication entitled, "AcroMed Songer Cable System: Ordering information for Implants and Instruments." 4/96, 4 pp.

Songer, Matthew, M.D., "Acromed Cable System by Songer: Cervical Technique Manual," pp. 1–17.

Songer, Matthew N., M.D., "ACROMED Cable System by Songer: Technique Manual," 1993, pp. 1–20.

Oxland, Thomas R., Ph.D., et al., SpineTech Inc. Publication entitled, "Biomechanical Rationale—The BAK Interbody Fusion System: An Innovative Solution," pp. 1–16.

SpineTech, Inc. publication entitled, "Patient Information on Spinal Fusion Surgery and the BAK Interbody Fusion System," 10 pp.

SpineTech, Inc. publication entitled, "BAK/Cervical Interbody Fusion System," 1994, 2 pp.

SpineTech, Inc. publications entitled, "Instrumentation BAK Interbody Fusion System," "Biomechanics BAK Interbody Fusion System," and "Porosity BAK Interbody Fusion System," 1996, 12 pp.

SpineTech, Inc. publication entitled, "The BAK Interbody Fusion System," 1996, 4 pp.

Depuy Motech, Inc. publication entitled, "Moss Miami 3–Dimensional Spinal Instrumentation: Taking Spinal Instrumentation to a New Dimension," 1995, 8 pp.

Shufflebarger, Harry L., M.D., "Moss Miami Spinal Instrumentation System: Methods of Fixation of the Spondylopelvic Junction," Lumbosacral and Spinopelvic Fixation, 1996 by Raven Publishers, Philadelphia, pp. 381–393.

Shufflebarger, Harry L., M.D., Dupuy Motech publication entitled, "Clinical Issue: Rod Rotation in Scoliosis Surgery," 5 pp.

AcroMed publication entitled, "Instruments," 3 pp.

SpineTech, Inc. publication entitled, "The Bone Harvester," 1996, 2 pp.

Wright Medical Technology Publication entitled, "Versalok Low Back Fixation System," 1996, pp. 1–4.

Danek Medical, Inc. Publication entitled, "TSRH Lumbar System," 1991, pp. 1–4.

Spinal Concepts Inc. Publication entitled, "The BacFixss—Posterior Lower Back Fixation System—Written Surgical Technique," 1997, pp. 1–11.

Dialog Web results for search for English language abstract for SU1424826 published Sep. 23, 1988, downloaded and printed from www.dialogweb.com on Jan. 22, 1999 (2 pages).

Dialog Web results for search for English language abstract for DE 4323956 published Jul. 19, 1993, downloaded and printed from www.dialogweb.com on Jan. 22, 1999 (2 pages).

Dialog Web results for search for English language abstract for FR 2717068 published Sep. 15, 1995, downloaded and printed from www.dialogweb.com on Jan. 22, 1999 (1 page).

International Search Report PCT/US 97/16971 dated Feb. 6, 1998.

International Search Report mailed Sep. 1, 1998, PCT/US98/08832.

* cited by examiner

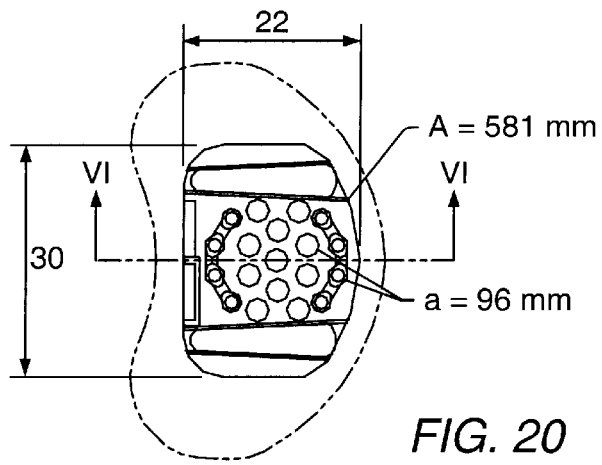
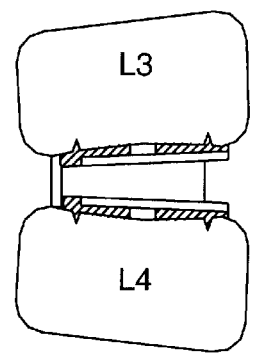
*FIG. 20*  *FIG. 21*
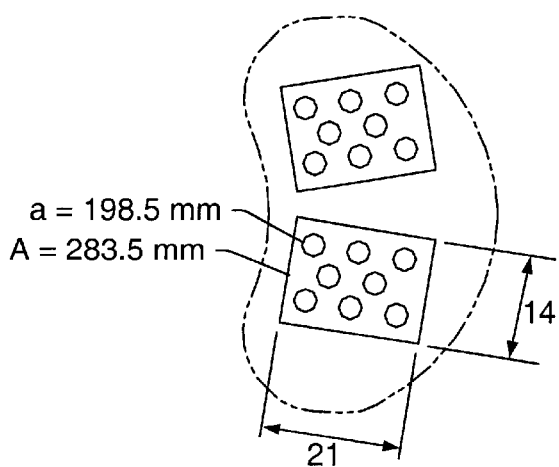
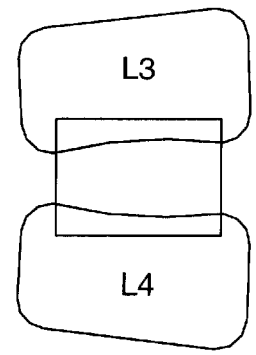
*FIG. 22*  *FIG. 23*
(PRIOR ART)  (PRIOR ART)
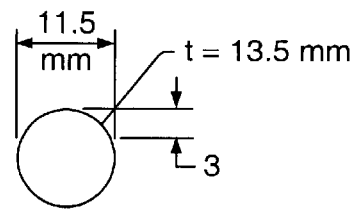
*FIG. 24*
(PRIOR ART)

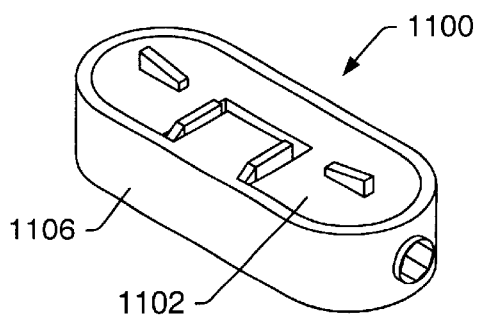
FIG. 50A
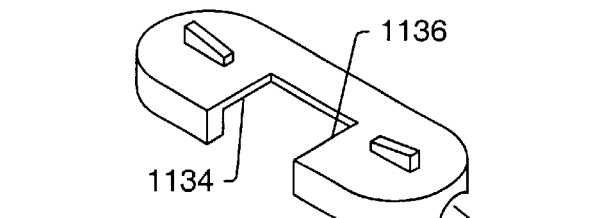
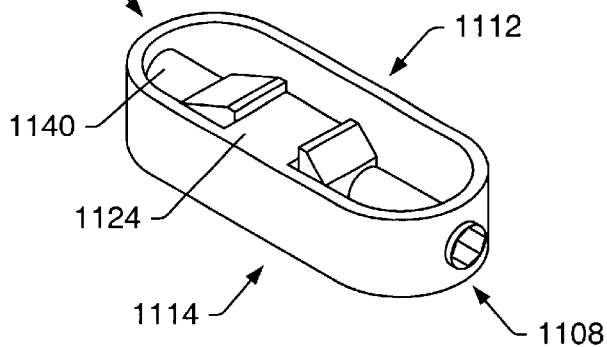
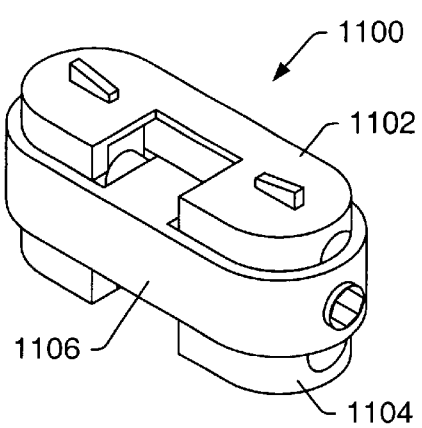
FIG. 50B
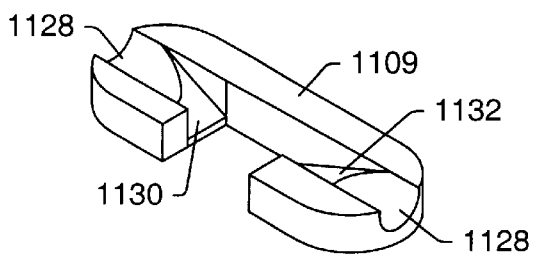
FIG. 50C

MULTI-VARIABLE-HEIGHT FUSION DEVICE

PRIOR APPLICATION

This application is a continuation-in-part of U.S. patent application Ser. No. 08/847,172 filed on May 1, 1997.

BACKGROUND OF THE INVENTION

1. Field of the Invention

The present invention generally relates to methods and apparatus for promoting an intervertebral fusion, and more particularly to an apparatus for insertion into a space between adjacent vertebrae to facilitate an intervertebral fusion while maintaining a substantially natural lordosis of the human spine.

2. Description of the Related Art

Intervertebral discs that become degenerated due to various factors such as trauma or aging typically have to be partially or fully removed. Removal of an intervertebral disc can destabilize the spine, making it necessary to replace the vertebral disc to maintain the height of the spine and to restore stability. Spinal implants are often used to prevent collapse of the spine and promote fusion. U.S. Ser. No. 08/740,123 filed Oct. 24, 1996 relates to methods and apparatus for facilitating a spinal fusion and is incorporated by reference as if fully set forth herein.

After an intervertebral disc is removed, an implant device is typically inserted between neighboring vertebrae to maintain normal disc spacing and restore spinal stability, thereby facilitating an intervertebral fusion. A conventional implant device disposed between neighboring vertebrae is depicted in FIGS. 1 and 2. The implant device contains a pair of engaging elements 20 that typically contain threading 10 to engage the vertebrae. Prior to inserting the engaging elements, a vertebral drill is typically inserted within the surgical wound to drill into the cortical endplate and remove fibrous and nuclear material. A vertebral tap may then be used to cut threads into the ends of the neighboring vertebrae. The engaging elements tend to be relatively inflexible and substantially undeflectable. The engaging elements are typically packed with bone graft to facilitate a spinal fusion.

Conventional implant devices tend to not maintain the "lordosis" or natural curvature of the lower lumbar spine. As shown in FIG. 1, the implant device contains parallel engaging sides 12 and 13 to contact vertebra 15. It is typically required that the engaging sides be parallel to prevent the fusion cage from slipping from the intervertebral space. The parallel configuration of the fusion cage tends to alter the lordosis of the spine. Such a loss of lordosis may result in an increased risk to other intervertebral discs located adjacent to the fusion level that may degenerate due to the altered force transmission in the spine.

FIG. 2 depicts a front view of the engaging elements 20 of the implant device. The engaging elements are substantially cylindrical and the region of contact between an engaging element and a vertebra is defined by arcuate portion 22. The cylindrical geometry of the engaging elements tends to provide a relatively small area of contact between the fusion cage and the vertebrae. The weight of the spine creates pressure on the vertebrae that is concentrated proximate the arcuate portions. Subsidence or deformation of the cortical layer of the vertebrae tends to result.

U.S. Pat. No. 5,522,899 to Michelson relates to a spinal implant for placement into the spinal disc space to stabilize the spine and participate in a vertebra to vertebra bony fusion. U.S. Pat. No. 5,489,308 to Kuslich et al. relates to an implant for use in spinal stabilization that includes a cylindrical body having external threading and radially disposed openings positioned to chip bone into an interior portion of the body when the implant is installed. The above-mentioned patents are incorporated by reference as if fully set forth herein.

The above-mentioned prior methods and systems inadequately address, among other things, the need to maintain the natural lordosis of the spine. It is therefore desirable that an improved spinal implant be derived for facilitating an intervertebral body fusion.

SUMMARY OF THE INVENTION

In accordance with the present invention, a spinal implant is provided that largely eliminates or reduces the aforementioned disadvantages of conventional implant devices. An embodiment of the invention relates to a fusion device for facilitating an interbody fusion between neighboring vertebrae of a human spine. The fusion device preferably includes a pair of sides or engaging plates for engaging the vertebrae and an alignment device disposed between the engaging plates for separating the engaging plates to maintain the engaging plates in lordotic alignment. The alignment device is preferably adapted to adjust the height between the engaging plates to customize the fusion device to a particular patient. The height of the fusion device preferably varies along the length of the device such that the height proximate an anterior end of the device differs from the height proximate a posterior end of the device.

The engaging plates are preferably substantially planar so as to inhibit subsidence of the vertebrae. The engaging plates may contain protrusions extending from their outer faces for enhancing an engagement between the vertebra and the engaging plate. The protrusions may be adapted to extend into the vertebra. The engaging plates preferably include a plurality of openings to allow bone growth to occur through the engaging plates. The openings in the face of the engaging plates preferably have a total area that is between about 60 percent and about 80 percent of a total surface area of the face (including the area of the openings).

The fusion device may include a retaining plate proximate the posterior end that serves as a backing against which bone graft may be packed between the engaging plates. The fusion device may also include a removable end cap proximate the anterior end for maintaining bone graft between the engaging plates.

In an embodiment, the alignment device includes a first strut and a second strut that extend between the engaging plates to define the separation distance therebetween. The fusion device preferably includes a first side and a second side opposite the first side. The first strut preferably runs from the anterior end to the posterior end along a location proximate the first side, and the second strut preferably runs from the anterior end to the posterior end along a location proximate the second side. The engaging plates preferably include a pair of slots sized to receive ends of the struts. The slots may have a substantially dovetail-shaped cross section that is conformed to the shape of the ends. Each slot is preferably tapered such that its width narrows in a direction from the anterior end to the posterior end whereby the width of the slot proximate the posterior end is less than the width of the end of the strut. The ends of the struts preferably have a lateral width that tapers in substantially the same manner as the slots such that a locking taper engagement is formable between the slots and the ends of the struts.

The height of each strut preferably varies along the length of the strut such that the separation distance between the engaging plates differs between the anterior end and the posterior end to allow the lordosis of the spine to be maintained. The first and second struts may have differing heights to cause the height of the fusion device to vary along the device from the first side to the second side to correct for a lateral deviation in the spinal column. Each of the struts may include a hinge to allow an upper member of the strut to pivot with respect to a lower member of the strut.

In an alternate embodiment, the engaging plates include slots and the fusion device further includes a pair of pins disposed within the slots. Each engaging plate preferably includes a rib extending in a substantially perpendicular direction from its face. The slot for receiving the pins is preferably disposed on the rib. The pins are preferably substantially elongated and may extend in a direction from the first side to the second side. The fusion device preferably further includes a rotatable connector engaging the pins. Rotation of the connector preferably causes movement of the pins relative to one another to alter the height of the fusion device to create a desired lordotic alignment.

The connector is preferably adapted to move axially between the engaging plates and may contain a retaining ring for contacting an engaging plate to limit movement of the connector through the fusion device. The connector preferably moves axially between the engaging plates in a direction from the anterior end to the posterior end, thereby moving the first pin toward the anterior end and the second pin toward the posterior end to increase the height between the engaging plates. The connector may be a screw having a threaded portion. The first pin may include a threaded opening for receiving a threaded portion of the connector. The second pin may be connected to an unthreaded portion of the connector.

The pins preferably include a receiving section and an end. The ends of the pins are preferably sized to fit within the slots in the ribs of the engaging plates. The receiving section may have a width greater than that of the ends of the pins and preferably contains an opening for receiving the connector.

One engaging plate preferably includes a first slot that may terminate in an end that extends in a diverging direction from an end of another slot contained on the other engaging plate. Movement of one of the pins preferably draws the ends of the slots together to alter the amount of separation between the engaging plates. The movement of the pins relative to one another preferably alters the height proximate the anterior end at a faster rate than the height proximate the posterior end is altered to achieve a desired lordotic alignment.

In an alternate embodiment, the fusion device contains a load-sharing member to promote a spinal fusion. The load-sharing member may be axially disposed within the struts. The load-sharing member is preferably substantially deflectable to allow movement of one of the engaging plates when a compressive force is exerted on the engaging plates. A predetermined spacing preferably exists between the upper and lower members. Application of a compressive force onto the engaging plates preferably deflects the load-sharing member and decreases the predetermined spacing between the members, thereby decreasing the height of the strut. The deflection of the load-sharing member preferably imparts stress to bone graft proximate the engaging plates to promote the development and growth of bone in accordance with Wolff's law.

The load-sharing member may be a pin having a circular cross-section and preferably is disposed in a bore extending axially through the strut. The bore preferably has a greater width than that of the load-sharing member to provide space for deflection of the load-sharing member. The load-sharing member may serve as a hinge-pin about which the upper member of the strut pivots with respect to the lower member of the strut.

The fusion device preferably further includes a connector for engaging the load-sharing member to impart force to the load-sharing member to cause it to deflect. The strut may include a threaded opening in its end for receiving the connector. The predetermined spacing between the upper and lower members may be set to a desired length by altering the position of the connector in the opening in the end of the strut. The load-sharing member may include an indention having a substantially planar surface to provide a site for engagement with the connector. The connector preferably engages the load-sharing member at a fulcrum point located at a predetermined horizontal distance from a support location where the lower member of the strut contacts the load-sharing member. The material properties of the load-sharing member and the distance between the fulcrum point and the support location are preferably controlled such that the modulus of elasticity across the strut is substantially equal to the modulus of elasticity of bone.

In an alternate embodiment, the fusion device may include a bracket assembly separating the engaging plates and supporting the alignment device. The alignment device may include at least one screw coupled to at least one cam block. In the context of this description, "screw" refers generally to any elongated member having external threading. The cam block may include an opening through which the cam block is coupled to the screw. An inner surface of the opening may include threading that is complementary to the threading at an end of the screw. The threading of the screw and the threading of the cam block may form an engagement such that rotation of the screw in a first angular direction causes the cam block to move in a first lateral direction and such that rotation of the screw in an angular direction opposite the first angular direction causes the cam block to move in a lateral direction opposite the first lateral direction.

The inner face of each of the engaging plates may include sloped tracks. The cam block may include an upper surface and a lower surface. The surfaces of the cam block may be beveled or sloped to correspond to the slope of the tracks, such that the cam block fits into the tracks in the inner surfaces of the engaging plates. The surfaces of the cam block and the tracks in the inner faces of the engaging plates may be configured such that movement of the cam block toward the exterior of the fusion device increases the height between the engaging plates and such that movement of the cam block toward the interior of the fusion device decreases the height between the engaging plates. Alternatively, the surfaces of the cam block and the tracks in the inner faces of the engaging plates may be configured such that movement of the cam block toward the exterior of the fusion device decreases the height between the engaging plates and such that movement of the cam block toward the interior of the fusion device increases the height between the engaging plates. Alternatively, in embodiments in which the fusion device includes more than one screw, the fusion device may include cam blocks and tracks in the engaging plates incorporating each of the above mentioned design elements.

The alignment device may include a single screw coupled to a single cam block. Alternatively, the alignment device may include a pair of screws, each of which is coupled to a single cam block. The screws may be situated such that a first screw is substantially parallel to and substantially adjacent a first edge of the fusion device. A second screw may be situated substantially parallel to and substantially adjacent a second edge of the fusion device opposite the first edge. Alternatively, the first screw may be substantially parallel to and substantially adjacent a first edge of the fusion device, and the second screw may be substantially parallel to and substantially adjacent a second edge of the fusion device adjacent to the first edge. Alternatively, the alignment device may include three screws, each of which is coupled to a single cam block, such that a first screw is substantially parallel to and substantially adjacent a first edge of the fusion device. A second screw may then be situated substantially parallel to and substantially adjacent a second edge of the fusion device opposite the first edge, and a third screw may be situated substantially parallel to and substantially adjacent a third edge located substantially perpendicular to and substantially adjacent the first edge and the second edge. Alternatively, the first screw may be substantially parallel to and substantially adjacent a first edge of the fusion device, the second screw may be substantially parallel to and substantially adjacent a second edge of the fusion device, and the third screw may be substantially parallel to and substantially between the first and the second screws.

In an alternate embodiment, the alignment device may include at least one screw coupled to a cam block as previously described, and the inner face of each of the engaging plates may include sloped tracks as previously described. A tip of each of the screws may be substantially unthreaded. The alignment device may further include a stationary block positioned between the engaging plates. The stationary block may include openings into which the unthreaded tip of each of the screws may be inserted. The stationary block may support each of the screws and preserve the engagement between the screws and the cam blocks during use.

The alignment device may include two screws, each of which is coupled to a cam block. The screws may be aligned such that the screws are positioned at an angle with respect to one another. Alternatively, the screws may be aligned such that the screws share a common axis of rotation. Two screws are said to share a "common axis of rotation" if the spatial relation of the longitudinal axes of rotation of the two screws is such that the longitudinal axis about which a first screw may be rotated and the longitudinal axis about which a second screw may be rotated are defined by the same line, irrespective of the physical dimensions (e.g., the diameters) of the screws or the longitudinal separation between the screws.

Alternatively, the alignment device may include three screws, each of which is coupled to a cam block. A first screw may share a common axis of rotation with a second screw, and a third screw may be aligned substantially perpendicular to the first screw and the second screw. Alternatively, the first screw may be oriented substantially perpendicular to the second screw, and the third screw may be oriented substantially at a first obtuse angle to the first screw and substantially at a second obtuse angle to the second screw. Alternatively, the first screw may be oriented substantially at a first non-perpendicular angle to the second screw and substantially at a second non-perpendicular angle to the third screw. Alternatively, the first screw may be oriented substantially parallel to the second screw, with the third screw situated between and substantially parallel to the first screw and the second screw.

Alternatively, the alignment device may include four screws, each of which is coupled to a cam block. A first screw may share a first common axis of rotation with a second screw, and a third screw may share a second common axis of rotation with a fourth screw. The first screw and the second screw may be situated substantially parallel to and substantially adjacent a first edge of the fusion device. The third screw and the fourth screw may be aligned substantially parallel to the first screw and the second screw and substantially adjacent an edge of the fusion device opposite the first edge. Alternatively, the first screw may share a common axis of rotation with the second screw, and the third screw may share a common axis of rotation with the fourth screw. The third screw and the fourth screw may be aligned substantially perpendicular to the first screw and the second screw. Alternatively, the first screw may share a common axis of rotation with the second screw and the third screw may share a common axis of rotation with the fourth screw. The third screw and the fourth screw may be aligned at a substantially non-perpendicular angle to the first screw and the second screw. The fusion device may be configured such that its cross-section is substantially rectangular. The first screw and the second screw may then be aligned substantially along a first diagonal of the rectangle, and third screw and the fourth screw may then be aligned substantially along a second diagonal of the rectangle intersecting the first diagonal.

In an alternate embodiment, the alignment device may include at least one screw configured to be coupled to a pair of cam blocks configured as described above. The inner face of each of the engaging plates may include sloped tracks as previously described. The screw may include a substantially unthreaded portion having a first diameter and a substantially threaded portion having a second diameter greater than the first diameter. Alternatively, the screw may include a substantially unthreaded portion having a first diameter and a substantially threaded portion having a second diameter substantially equal to the first diameter. Each of the cam blocks may include an opening through which the cam block is coupled to the screw. The inner surface of the opening in a first cam block may be substantially unthreaded. The inner surface of the opening in a second cam block may include threading that is complementary to the threading of the screw. The bracket assembly may include projections into the interior of the fusion device and having inner surfaces having threading that is complementary to the threading of the screw. Rotation of the screw in a first angular direction may thus cause the screw to move in a first lateral direction with respect to the bracket assembly, and rotation of the screw in an angular direction opposite the first angular direction may thus cause the screw to move in a lateral direction opposite the first lateral direction.

The unthreaded opening in the first cam block may be substantially similar in diameter to the diameter of the unthreaded portion of the screw. The unthreaded portion of the screw may pass through the opening in the first cam block such that the screw is free to rotate within the opening in the first cam block. The screw may further include a flange coupled to the screw at a first end of the screw adjacent the unthreaded portion of the screw. The first end of the screw may include an indentation sized and shaped such that a tip of an adjusting tool may be inserted into the indentation. The adjusting tool may be a screwdriver. Preferably, the adjusting tool is an allen wrench. The adjusting tool may be used to rotate the screw. The diameter of the threaded portion of the screw and the diameter of the flange may be sufficiently larger than the diameter of the opening in the first cam block such that coupling is maintained between the first cam block and the screw as the screw is rotated (i.e., the screw remains inserted in the opening through the first cam block) and such that the first cam block is constrained to move laterally in the same direction as the screw when the screw is rotated. The threading of the screw and the threading of the second cam block may form an engagement between the second cam block and the screw such that rotation of the screw causes the second cam block to move in a lateral direction opposite the direction of lateral motion of the screw.

The alignment device may include a single screw coupled to a pair of cam blocks and situated substantially parallel to and substantially adjacent an edge of the fusion device. Alternatively, the alignment device may include a pair of screws that are each coupled to a pair of cam blocks. The screws may be situated such that a first screw is substantially parallel to and substantially adjacent a first edge of the fusion device. A second screw may be situated substantially parallel to and substantially adjacent a second edge of the fusion device opposite the first edge. Alternatively, the first screw may be situated substantially parallel to and substantially adjacent a first edge of the fusion device and the second screw may be situated substantially parallel to and substantially adjacent a second edge of the fusion device adjacent to the first edge. Alternatively, the alignment device may include three screws, each of the screws being coupled to a pair of cam blocks, such that a first screw is substantially parallel to and substantially adjacent a first edge of the fusion device. A second screw may then be situated substantially parallel to and substantially adjacent a second edge of the fusion device opposite the first edge, and a third screw may be situated substantially parallel to and substantially adjacent a third edge of the fusion device located substantially perpendicular to the first edge and the second edge.

In an alternate embodiment, the screw in the alignment device may be a turnbuckle. In the context of this description, "turnbuckle" refers to a screw having external threading in a first direction at a first end and external threading in a direction opposite the first direction at a second end opposite the first end. The turnbuckle may be coupled to a pair of cam blocks via threaded openings in the cam blocks. An inner surface of each of the openings may include threading that is complementary to the threading at one of the ends of the turnbuckle. The threading of the turnbuckle and the threading of the cam blocks may form an engagement such that rotation of the turnbuckle in a first direction causes the cam blocks to move away from each other and such that rotation of the turnbuckle in a direction opposite the first direction causes the cam blocks to move toward each other. The inner face of each of the engaging plates may include sloped tracks as previously described. At least one end of the turnbuckle may include an indentation sized and shaped such that a tip of an adjusting tool may be inserted into the indentation. The adjusting tool may be a screwdriver. Preferably, the adjusting tool is an allen wrench. The adjusting tool may be used to rotate the turnbuckle.

The turnbuckle may include a middle portion disposed between the first end and the second end and having a thickness greater than a thickness of the first end and a thickness of the second end. The bracket assembly may include lateral projections into the interior of the fusion device. The middle portion of the turnbuckle may be configured to fit between the lateral projections from the bracket assembly. The lateral projections may include openings of a size sufficient to allow the ends of the turnbuckle to pass through without allowing the middle portion to pass through, thus maintaining the turnbuckle in the bracket assembly.

The alignment device may include a single turnbuckle coupled to a pair of cam blocks and situated substantially parallel to and substantially adjacent an edge of the fusion device. Alternatively, the alignment device may include a pair of turnbuckles that are each coupled to a pair of cam blocks. The turnbuckles may be situated such that a first turnbuckle is substantially parallel to and substantially adjacent a first edge of the fusion device. A second turnbuckle may be situated substantially parallel to and substantially adjacent a second edge of the fusion device opposite the first edge. Alternatively, the first turnbuckle may be substantially parallel to and substantially adjacent a first edge of the fusion device, and the second turnbuckle may be substantially parallel to and substantially adjacent a second edge of the fusion device adjacent to the first edge. Alternatively, the alignment device may include three turnbuckles that are each coupled to a pair of cam blocks, such that a first turnbuckle is substantially parallel to and substantially adjacent a first edge of the fusion device. A second turnbuckle may then be situated substantially parallel to and substantially adjacent a second edge of the fusion device opposite the first edge, and a third turnbuckle may be situated substantially parallel to and substantially adjacent a third edge of the fusion device located substantially perpendicular to the first edge and the second edge.

The above embodiments may be used independently or in combination.

An advantage of the invention relates to an intervertebral body fusion device that substantially maintains the natural lordosis of the human spine.

Another advantage of the invention relates to an intervertebral body fusion device adapted to correct a lateral deviation in the spinal column.

Anther advantage of the invention relates to an intervertebral body fusion device that substantially maintains the natural lordosis of the human spine while simultaneously being adapted to correct a lateral deviation in the spinal column.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 20 depicts a top view of a fusion device located on a vertebral body;

FIG. 21 depicts a cross-sectional view of the fusion device taken along plane VI of FIG. 3;

FIG. 22 depicts a top view of a conventional fusion cage having a pair of cylindrical elements disposed on a vertebra;

FIG. 23 depicts a side view of one of the cylindrical elements in FIG. 22 disposed between neighboring vertebrae;

FIG. 24 depicts a front view of the cylindrical element in FIG. 23;

Figure 1:
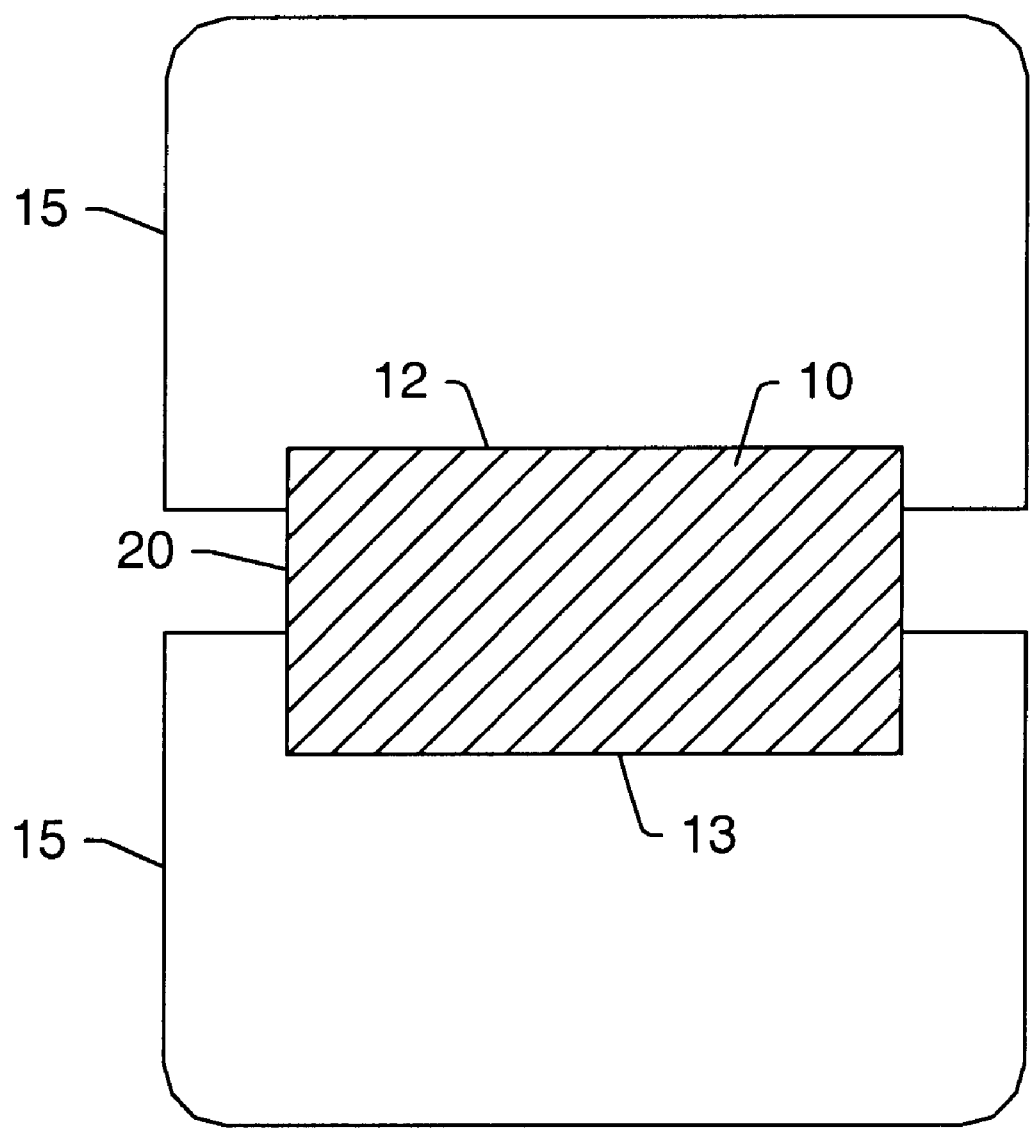
FIG. 1 depicts a conventional intervertebral body fusion implant positioned between neighboring vertebrae.
Figure 2:
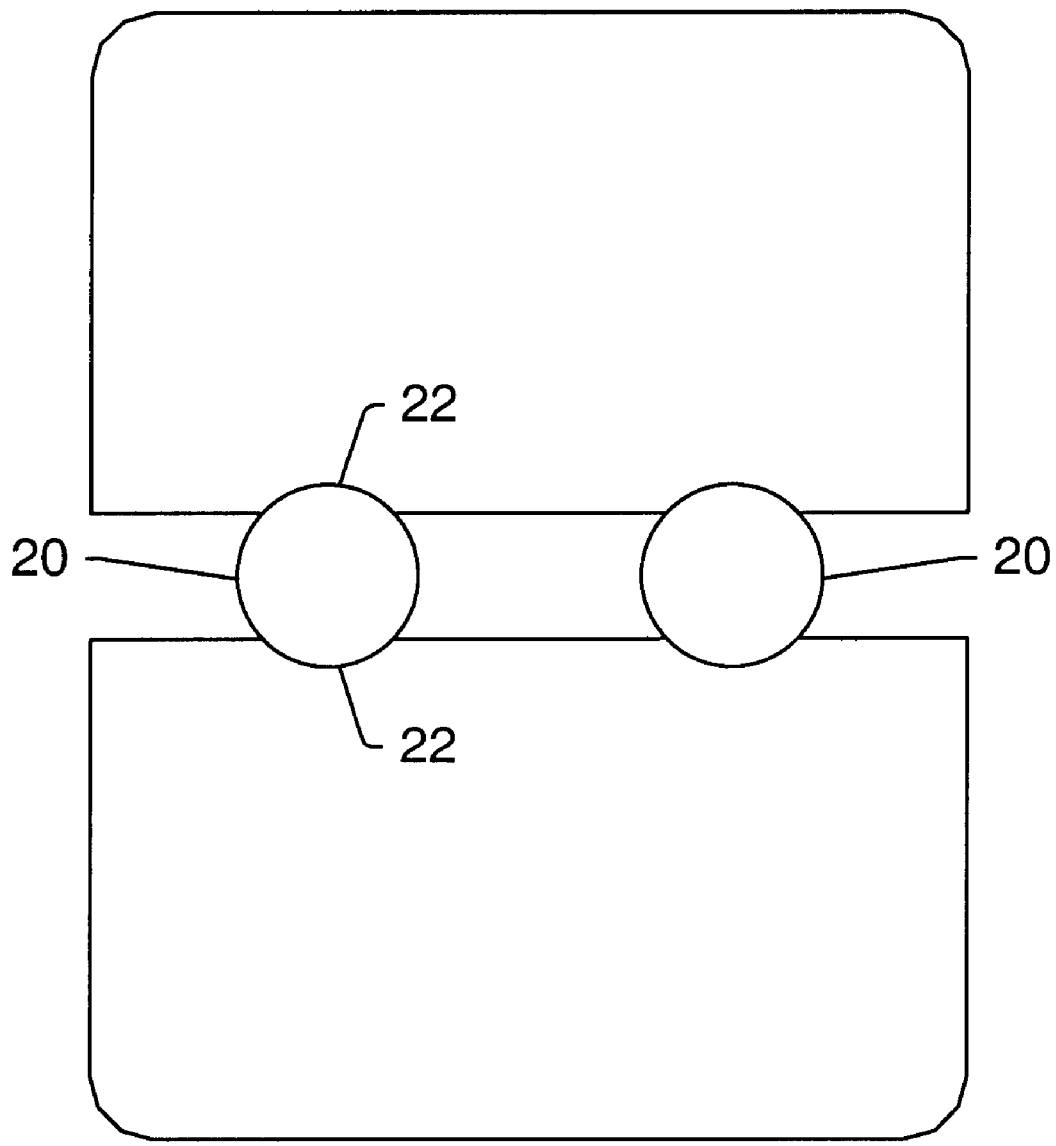
FIG. 2 depicts another conventional intervertebral body fusion implant that includes a pair of cylindrical members positioned between neighboring vertebrae.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 3:
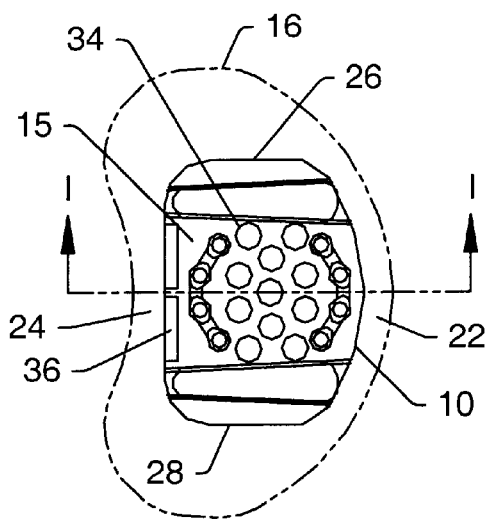
FIG. 3 depicts a top view of a fusion device located on a vertebral body.
Figure 5:
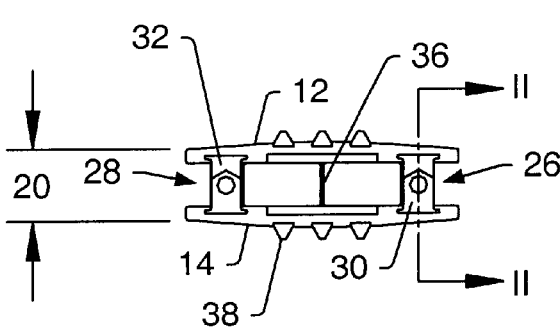
FIG. 5 depicts a front view of a fusion device.

A preferred embodiment of an interbody fusion implant device 10 for facilitating the formation of a spinal fusion is depicted in FIGS. 3–5. A top view of the fusion device is depicted in FIG. 3. Fusion device 10 preferably includes a pair of sides or engaging plates 12 and 14 for engaging vertebral bodies 16 and 18. The engaging plates may contain curved edges such that the outer face 15 of the plates conforms to the shape of the cross section of the vertebral bodies as shown in FIG. 3. The fusion device has a height 20 defined by the vertical distance from the outer face 15 of the engaging plate 12 to the outer face of the engaging plate 14. The height 20 of the fusion device is preferably adjustable and may vary along the fusion device between anterior end 22 and posterior end 24 to maintain the natural lordosis of the spine. Height 20 may also vary along device 10 from first side 26 to second side 28 to correct for a lateral deviation in the spine as may occur in scoliosis. Fusion device 10 preferably further includes an alignment device for adjusting the height 20 so that the natural lordosis of the spine is substantially maintained after the fusion device is implanted. The alignment device may be used to adjust the separation distance between the engaging plates proximate the anterior end and independently adjust the separation distance between the engaging plates proximate the posterior end.

A spinal fusion is typically employed to eliminate pain caused by the motion of degenerative disk material. Upon successful fusion, fusion device 10 becomes permanently fixed within the disc space. The fusion device is preferably packed with bone graft 40 to promote the growth of bone through and around the fusion device. Such bone graft may be packed between engaging plates 12 and 14 prior to, subsequent to, or during implantation of the fusion device. Bone substitute material that is well known to those skilled in the art may be used instead of bone graft. A bone harvester kit, commercially available from Spine-Tech, Inc. located in Minneapolis, Minn., may be used to inject bone graft between the engaging plates. The pamphlet entitled "Bone Harvester: Minimally Invasive Bone Harvesting Kit" (available from Spine-Tech, Inc.) details the use of the bone harvesting kit.

In an embodiment of the invention, the faces 15 of engaging plates 12 and 14 contain a plurality of openings 34 disposed therein to allow bone development and growth through the engaging plates 12 and 14 and between fusion device 10 and neighboring vertebrae 16 and 18. In an embodiment, the openings 34 have a combined area that is greater than about 50 percent of the area of face 15 (including the area of the openings 34), more preferably between about 60 percent and about 80 percent of the area of face 15, and more preferably still about 70 percent or more of the area of face 15.

The fusion device may contain a retaining plate 36 proximate posterior end 24 to provide a backing against which bone graft may be packed and to maintain the bone graft between the engaging plates. Retaining plate 36 may be substantially planar and may contain openings to allow bone ingrowth therethrough. A removable endcap 25 may be positioned proximate anterior end 22 to contain bone graft within the fusion device and to prevent the migration of bone graft outside the engaging plates. The endcap 25 may contain one or more openings for allowing bone ingrowth between a vertebral body and bone graft contained between the engaging plates. Endcap 25 is preferably made of a plastic material such as polyethylene that tends to be non-irritating and non-abrasive to the surrounding tissues.

Figure 4A:
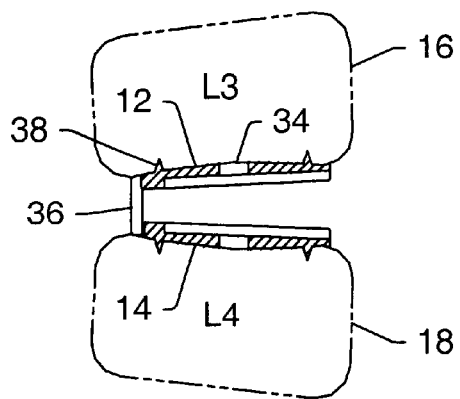
FIG. 4a depicts a cross-sectional view of the fusion device of FIG. 3 taken along plane I.
Figure 4B:
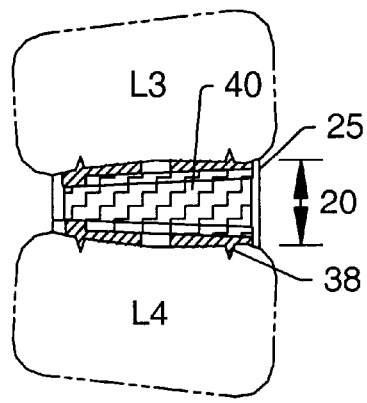
FIG. 4b depicts a cross-sectional view of the fusion of FIG. 3 device taken along plane I wherein the fusion device contains bone graft and has been adjusted to maintain a substantially natural lordosis.

A cross section of the fusion device taken through plane I of FIG. 3 is depicted in FIG. 4a and FIG. 4b. FIG. 4a shows the relative position of engaging plates 12 and 14 before height 20 has been adjusted with an alignment device to achieve a substantially natural lordosis. FIG. 4b shows the relative position of the plates after height 20 has been adjusted and bone graft 40 has been packed between the engaging plates. FIG. 4b shows that height 20 is greater in the vicinity of anterior end 22 as compared to posterior end 24 to maintain the natural lordosis of the spinal column. The faces 15 of the engaging plates 12 and 14 are preferably planar to provide a relatively large contact area between the engaging plates and the neighboring vertebrae. In this manner, subsidence of the vertebrae may be prevented because the force imparted to the vertebrae from the fusion device is not concentrated across a relatively small area of the vertebrae as in some conventional implants. Alternately, the engaging plates may be non-planar. The engaging plates also preferably contain a plurality of spikes or protrusions 38 extending from the face 15 for enhancing an engagement between the vertebra and the engaging plate. The protrusions may extend into the vertebra to prevent the fusion device from moving out of the disc space. The engaging plates are preferably constructed of titanium or a titanium alloy, although it is to be understood that other materials (e.g., ceramics, metals, carbon composites) may be used.

A front view of the fusion implant device is depicted in FIG. 5. In an embodiment of the invention, the alignment device includes a first strut 30 and a second strut 32 that each extend between engaging plates 12 and 14 along the length of the fusion device from anterior end 22 to posterior end 24. As described herein, a "strut" is taken to mean any support member disposed between the engaging plates to separate the engaging plates. Strut 30 preferably extends along the fusion device proximate first side 26. Strut 32 is preferably substantially parallel to strut 30 and may extend along the fusion device proximate second side 28. The struts 30 and 32 serve to create a predetermined spacing between the engaging plates. The predetermined spacing is preferably such that the height 20 is approximately equal to the height of the disc material that formerly occupied the disc space between the vertebral bodies.

Figure 6A:
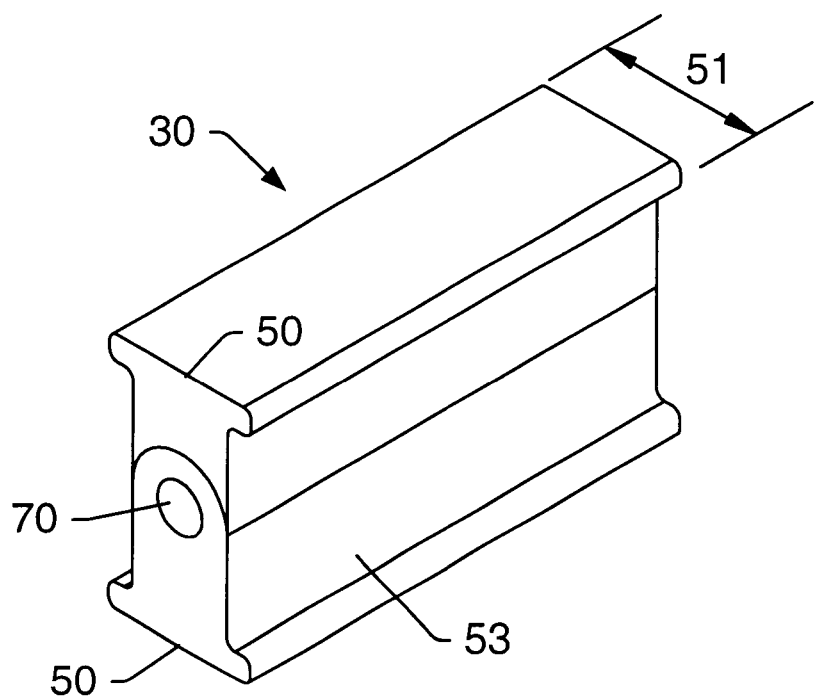
FIG. 6a depicts a perspective view of a strut.

A perspective view of an embodiment of the strut is depicted in FIG. 6a. The strut may have an "I-beam" shape and preferably includes a pair of ends 50. The ends 50 may have a lateral width 51 that is greater than that of the sides 53. The ends preferably have a "dovetail" shaped cross-section as shown in FIG. 6a. The engaging plates preferably contain elongated slots 60 (shown in FIGS. 7 and 8) sized to receive ends 50 of the first and second struts. The slots 60 preferably have a complementary dovetail shape as depicted in FIG. 8 that conforms to the shape of the end 50. The struts may be connected to the engaging plates by sliding ends 50 into the slots 60 in a direction from anterior end 22 to posterior end 24 or vice versa.

Figure 7:
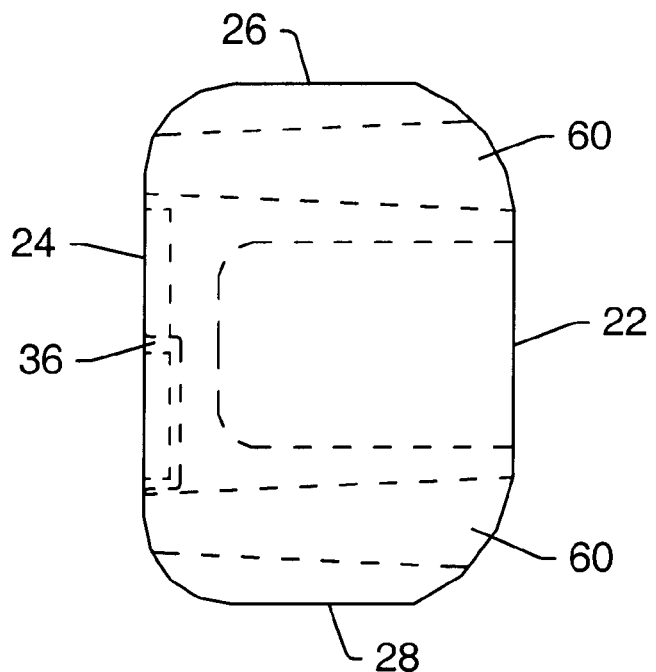
FIG. 7 depicts a top view of a fusion device.
Figure 8:
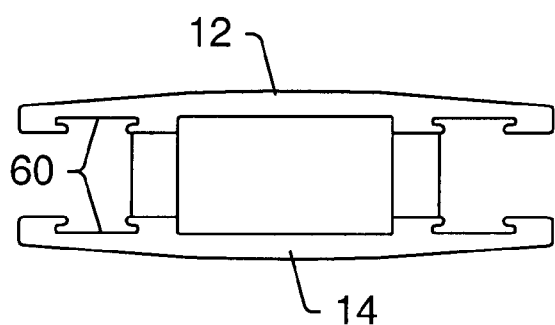
FIG. 8 depicts a front view of a pair of engaging plates.
Figure 17:
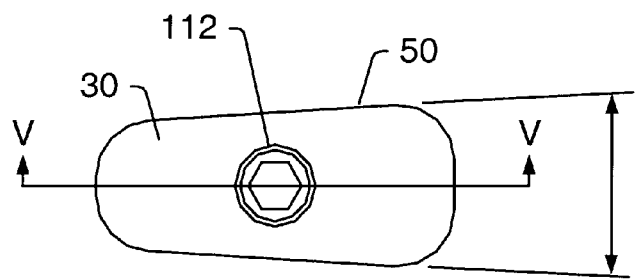
FIG. 17 depicts a top view of a strut having a tapered end.

In an embodiment, the slots are tapered such that their width narrows in a direction from the anterior end to the posterior end as shown in FIG. 7. The ends 50 may be tapered (as shown in FIG. 17) such that the lateral width 51 narrows along the length of the strut. The taper of the lateral width of the strut preferably matches that of slot 60. The width of the slot proximate the anterior end is preferably sized to allow the strut end to be slid into the slot. The width of the slot proximate the posterior end is preferably less than the lateral width 51 of the narrowest portion of end 50. The tapering of the slots preferably allows a "locking taper engagement" of the strut ends within the slots. A "locking taper engagement" is taken to mean a fixable interference fit formed between end 50 and slot 60 whereby the strut resists dislodgment when force is imparted to the fusion device from the adjacent vertebrae. In an alternate embodiment, the slots may be tapered such that the width of the slots narrows in a direction from the posterior end to the anterior end.

Figure 6B:
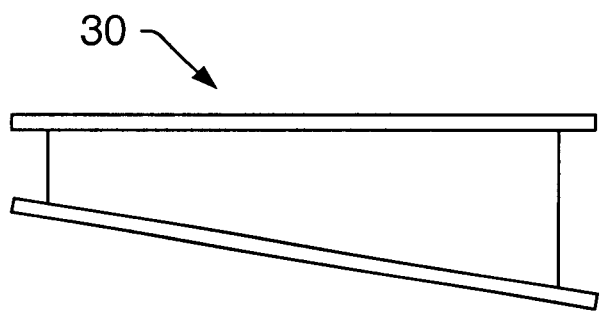
FIG. 6b depicts a side view of a tapered strut.

The first and second struts preferably each have a predetermined height that defines the height of the fusion device. The engaging plates 12 and 14 are preferably adapted to receive struts of various heights to allow height 20 to be varied to fit the needs of the patient. A side view of a tapered strut is depicted in FIG. 6b. The tapered strut preferably has a height that varies along its length. In this manner, the tapered strut is positionable between the engaging plates 12 and 14 to cause height 20 to decrease in a direction from anterior end 22 to posterior end 24 whereby the natural lordosis of the human spine is maintained by the fusion device. The degree of taper of the strut corresponds to a desired lordosis and may vary depending upon the size of the patient.

Figure 9:
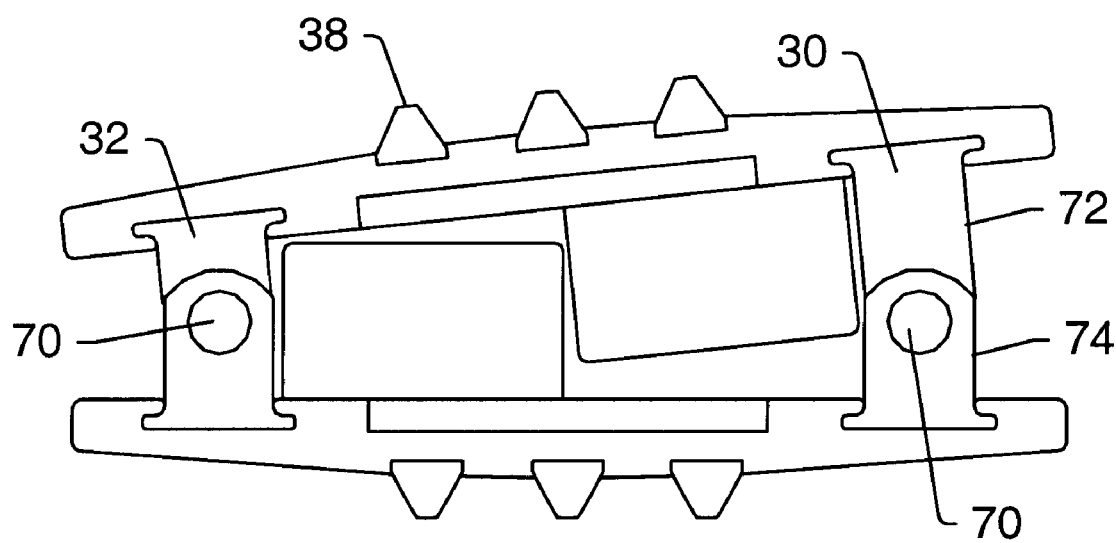
FIG. 9 depicts a front view of a fusion device having pivotable struts.

In an embodiment, the first and second struts have differing heights to cause height 20 to vary between first end 14 and second end 16. In this manner, the fusion device may be used to correct a lateral deviation in the spinal column as may occur in scoliosis. A front view of a fusion device containing struts having different heights is depicted in FIG. 9. Each of the struts preferably contains a hinge pin 70 to allow an upper member 72 of the strut to pivot with respect to a lower member 74 of the strut. In this manner, the struts may be pivoted as shown in FIG. 9 such that the ends of the struts are properly aligned with the slots of the engaging plates when a height difference exists between the first and second struts.

To install the fusion device, a discectomy is preferably performed from an anterior approach. All cartilage and soft tissue are preferably removed from the vertebral endplate as would normally be done for placement of a femoral strut graft. Such a procedure is well within the knowledge of a skilled practitioner of the art. The engaging plates may be deployed in the disc space between the adjacent vertebrae. A distraction force may be applied to the engaging plates using a laminae spreader or similar device to force the vertebrae to a selected separation distance and lordotic alignment. The use of a laminae spreader is well known to those skilled in the art. The proper heights for the first and second struts may be determined beforehand using x-ray techniques in which the posterior and anterior portions of the intervertebral disc space are examined.

Appropriately sized and tapered struts are preferably slipped into slots 60 and tapped until a locking taper engagement is achieved between the strut ends and the slots. If struts of differing heights are used to correct for a lateral deviation in the spinal column, each strut may be pivoted about hinge pin 70 prior to insertion so that ends 50 are properly aligned for placement into grooves 60. Bone graft material is preferably inserted through the anterior end and packed between the engaging plates. Retaining plate 36 preferably prevents the bone graft material from passing through the fusion device during packing. Endcap 25 may then be placed onto the anterior end.

Figure 10:
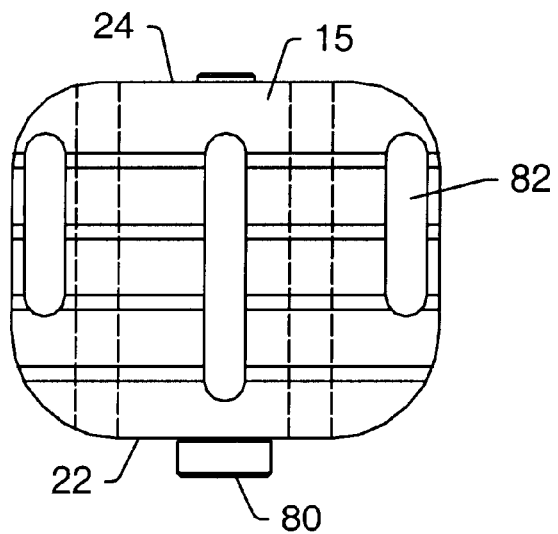
FIG. 10 depicts a top view of a fusion device containing a connector.

In an alternate embodiment depicted in FIGS. 10–16, the alignment device includes a connector 80 for adjusting the height 20 of the device to achieve a desired lordotic alignment. FIG. 10 depicts a top view of the fusion device. Connector 80 is preferably a drive screw that is rotatable to adjust height 20. Connector 80 preferably extends between engaging plates 12 and 14 and may be adapted to move axially through the fusion device in a direction from anterior end 22 to posterior end 24. The engaging plates may contain elongated openings 82 for allowing bone growth through the faces 15 of the plates.

Figure 11:
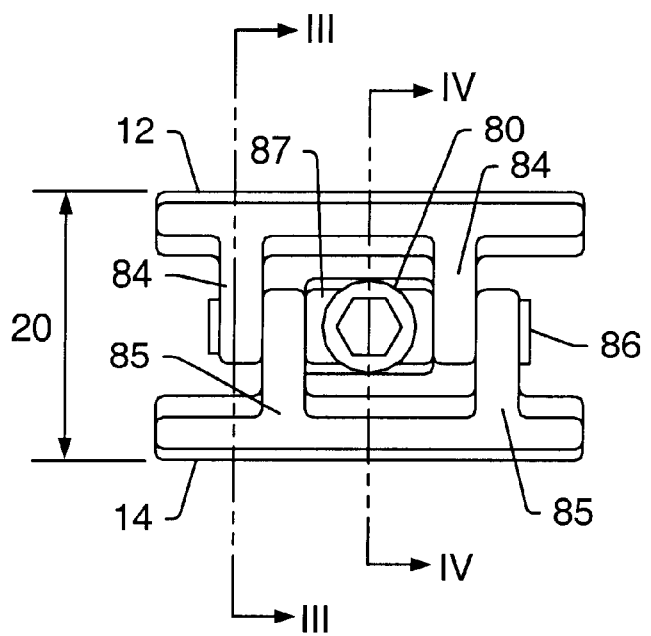
FIG. 11 depicts an anterior view of a fusion device having a connector and cam pins.
Figure 12:
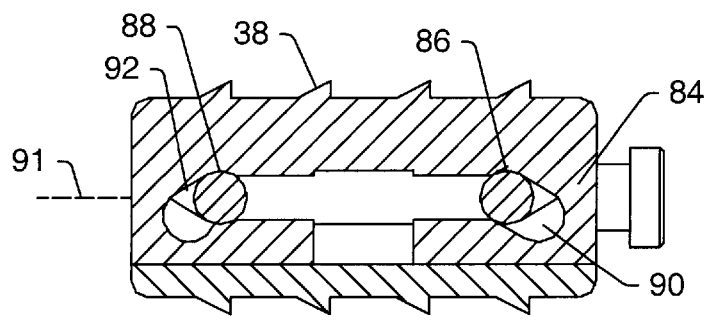
FIG. 12 depicts a cross-sectional view taken along plane III of FIG. 11 of the fusion device in a lowered position.
Figure 13:
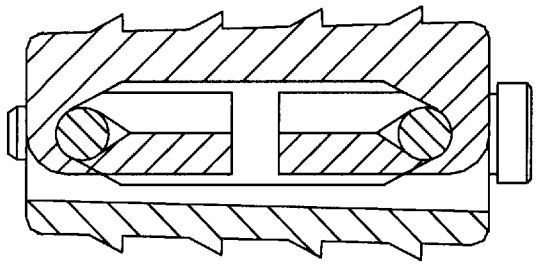
FIG. 13 depicts a cross-sectional view taken along plane III of FIG. 11 of the fusion device in a raised position.

FIG. 11 depicts a front (anterior) view of the fusion device in a raised position. In an embodiment, the engaging plates include ribs 84 and 85 that may extend substantially perpendicularly from face 15. A cross-sectional view taken along plane III of FIG. 11 is depicted in each of FIG. 12 and FIG. 13. FIG. 12 depicts rib 84 and cam pins 86 and 88 in section with the fusion device in a "lowered position" (i.e., unadjusted for lordotic alignment). FIG. 13 depicts the rib and cam pins in section with the fusion device in the "raised position" (i.e., adjusted for lordotic alignment). As described herein, "cam pin" is taken to mean any connecting element capable of extending from the connector into the slots 90 and 92. Each of the cam pins may be intersected by an imaginary longitudinal axis 91 axially extending through the fusion device.

Rib 84 preferably contains a slot 90 having a first end and a second end. The ends of slot 90 preferably terminate in a direction below axis 91. The first end of slot 90 preferably extends downwardly substantially toward either the face of engaging plate 14 or the anterior end. The second end of slot 90 preferably extends downwardly substantially toward either the face of engaging plate 14 or the posterior end. Rib 85 preferably contains a slot 92 having a pair of ends that extend in diverging directions from the slot ends of rib 84. The ends of slot 92 preferably terminate in a direction above axis 91. The first end of slot 92 preferably extends upwardly substantially toward either the face of engaging plate 12 or the anterior end. The second end of slot 90 preferably extends upwardly substantially toward either the face of engaging plate 12 or the posterior end. The engaging plates are preferably connected together with cam pins 86 and 88, which preferably have ends sized to fit within slots 90 and 92. The cam pins preferably are disposed through the fusion device in a direction from the first side to the second side. Pins 86 and 88 preferably contain a receiving section 87 having an opening for receiving connector 80. Receiving section 87 may have a greater width (e.g., diameter) than the ends of pins 86 and 88 disposed in slots 90 and 92.

Figure 14:
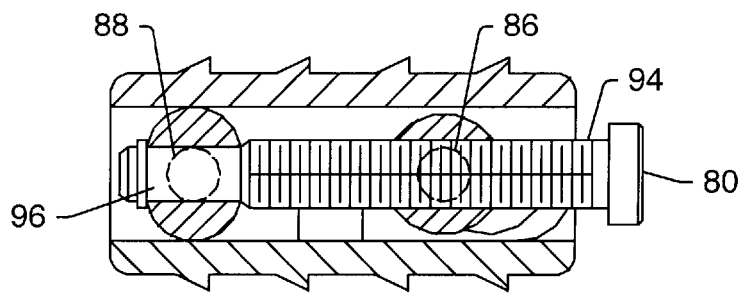
FIG. 14 depicts a cross-sectional view taken along plane IV of FIG. II of the fusion device in a lowered position.
Figure 15:
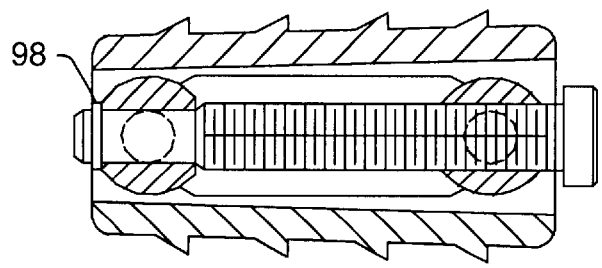
FIG. 15 depicts a cross-sectional view taken along plane IV of FIG. 11 of the fusion device in a raised position.

FIG. 14 and FIG. 15 each depict a cross-sectional view of the fusion device taken along plane IV of FIG. 11. FIG. 14 depicts the connector and cam pins in section with the fusion device in the lowered position. FIG. 15 depicts the connector and the cam pins in section with the fusion device in the raised position. In an embodiment, connector 80 contains a threaded portion 94 and an unthreaded portion 96. Pin 86 is preferably connected to the threaded portion and pin 88 is preferably connected to the unthreaded portion.

In an embodiment, a torque delivered to the connector is converted into a separation force between the cam pins. Rotating the connector in a counterclockwise direction preferably moves the connector in a direction from the anterior end to the posterior end. Pin 88 is preferably attached to the connector and preferably moves in the same manner as the connector. Pin 86 preferably contains an opening having complementary threading to that of the connector. Pin 86 preferably moves toward the anterior end in a direction opposite the motion of the connector to increase the separation between pin 88 and pin 86. The ends of the pins preferably move along the angled portions of the slots 90 and 92, causing the ends of the slots to be drawn together. In this manner, the separation between the engaging plates is increased. The connector may be rotated in a counterclockwise direction to move the connector in a direction from the posterior end to the anterior end, thereby decreasing height 20.

Conventional methods of surgically implanting fusion devices tend to require that distraction instruments be inserted between the vertebrae to separate them and allow insertion of the fusion device therebetween. The surgical incision typically must be widened to accommodate the distraction instruments. In an embodiment, the fusion device in the lowered position has a height that is less than the disc space between the vertebrae. In this manner, the fusion device may be inserted between the vertebrae with minimal distraction. Connector 80 is preferably operable to separate the engaging plates (hence the vertebrae) and create a desired lordotic alignment.

The distance that the engaging plates are separated per unit torque applied to the connector will tend to depend upon the angle of the slots 90 and 92. The slots are preferably angled such that the height 20 proximate the anterior end changes at a greater rate than the height 20 proximate the posterior end when the connector is adjusted to alter the distance between the plates. In this manner, a desired lordotic alignment may be achieved. It is to be understood that the fusion device is operable in a semi-raised position that is intermediate the raised and lowered positions depicted in FIGS. 12–15. The connector is preferably rotated to a selected degree to achieve a preferred height 20 proximate the anterior and posterior ends to suit the particular patient. The angle of the slots 90 and 92 may vary among patients and is preferably selected to achieve a desired lordotic alignment. The connector may include a retaining ring 98 for contacting one or both of the engaging plates to limit the degree to which the connector can move through the fusion device.

Figure 16:
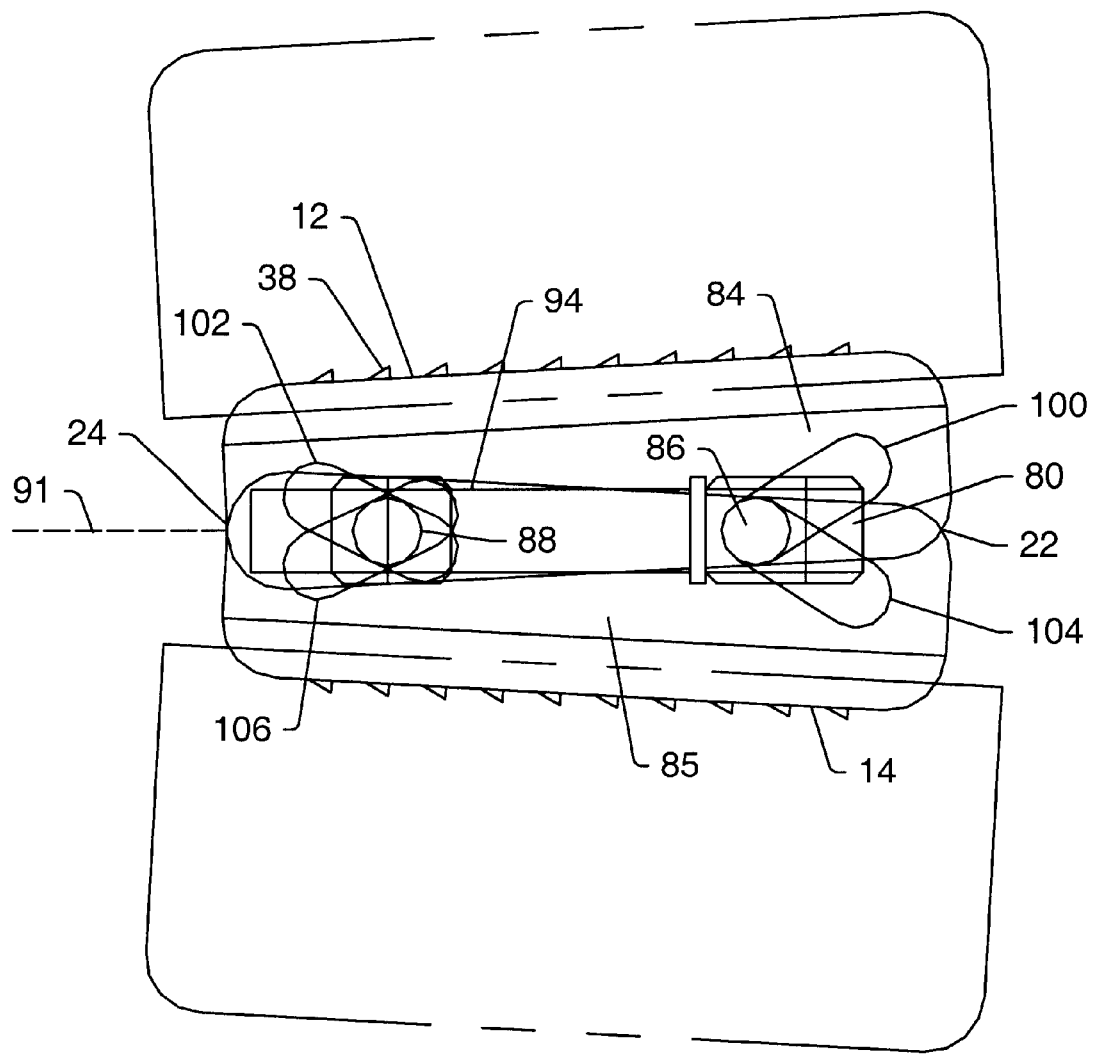
FIG. 16 depicts a side view of a fusion device disposed between vertebrae.

FIG. 16 depicts a side view of an alternate embodiment of the fusion device installed between neighboring vertebrae. Pin 86 may be located on the unthreaded portion of the shank adjacent to the head of connector 80. Pin 88 may be located on threaded portion 94 of the shank of connector 80. Rib 84 preferably includes a first slot 100 that is angled diagonally upward from axis 91 in a direction substantially toward either the face of engaging plate 12 or the anterior end 22. Rib 84 preferably also includes a second slot 102 that is angled diagonally upward from axis 91 in a direction substantially toward either the face of engaging plate 12 or the posterior end 24. Rib 85 preferably includes a first slot 104 that is angled diagonally downward from axis 91 in a direction substantially toward either the face of engaging plate 14 or the anterior end 22. Rib 85 preferably also includes a second slot 106 that is angled diagonally downward from axis 91 in a direction substantially toward either the face of engaging plate 14 or the posterior end 24. To adjust the fusion device into the raised position, the connector may be rotated to cause the cam pins to be moved in a direction toward one another. Pin 86 preferably moves with the connector in a direction from the anterior end to the posterior end to increase the separation between the engaging plates proximate the anterior end. Pin 88 preferably contains a threaded opening for receiving the connector and may move in a direction toward the posterior end to increase the separation between the engaging plates proximate the posterior end.

In an alternate embodiment, each of the pins 86 and 88 contains a threaded opening for receiving the connector 80. The connector may be a "double-threaded" screw having two threaded portions for complementing the threaded openings of the pins 86 and 88. Rotation of the screw in a first direction preferably causes the pins to move toward one another to increase the separation between the engaging plates. Rotation of the screw in an opposite direction preferably causes the pins to move away from one another to reduce the separation between the engaging plates.

In an alternate embodiment, the alignment device includes a load-sharing member to allow the engaging plates to move in response to a compressive force of predetermined magnitude. In accordance with Wolff's law, bone growth tends to occur in the presence of stress (e.g., load), and bone tends to be absorbed in the absence of stress. The load-sharing member preferably enables the fusion device to "share" compressive forces exerted onto the spinal column with the bone graft in the vicinity of the fusion device. The load-sharing member preferably is deflected upon receiving a predetermined force to cause the engaging plates to move, thereby shifting load from the fusion device to the bone graft proximate the fusion device. It is believed that providing a selected amount of stress to the bone graft in a such a manner will tend to result in a higher fusion rate as well as a stronger fusion mass.

Figure 18:
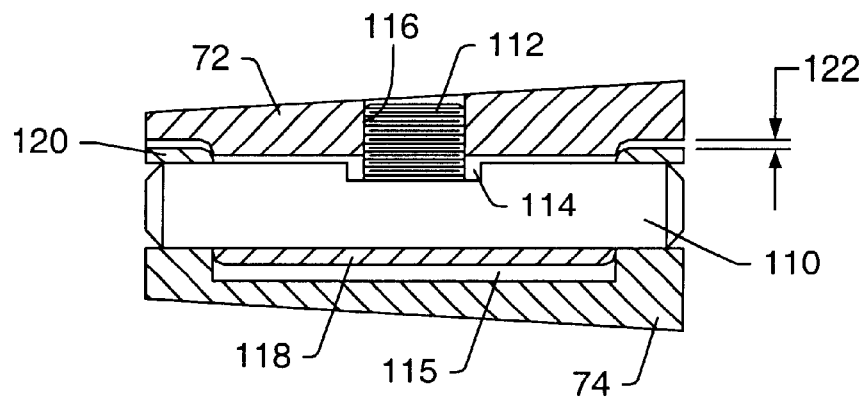
FIG. 18 depicts a cross-sectional view taken along plane V of FIG. 17 of the strut in an unloaded position.
Figure 19:
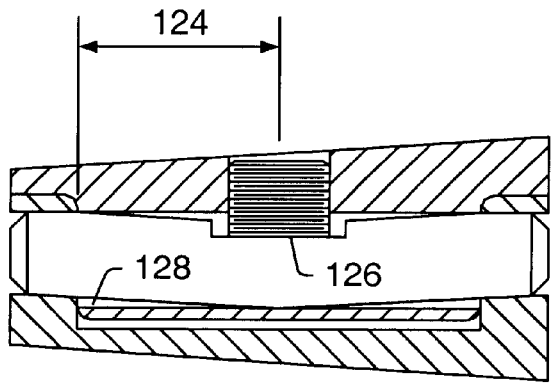
FIG. 19 depicts a cross-sectional view taken along plane V of FIG. 17 of the strut in a loaded position.

An embodiment of the load-sharing fusion device is depicted in FIGS. 17–19. A top view of a strut 30 containing a load-sharing member is depicted in FIG. 17. FIGS. 18 and 19 depict cross-sectional views of the strut taken along plane V of FIG. 17. Load-sharing member 110 is preferably disposed axially through the strut. The load-sharing member may be contained in a bore extending into the strut. The bore preferably has a width (e.g., diameter) that is greater than that of the load-sharing member to allow sufficient space for the load-sharing member to be deflected. The bore is preferably disposed within lower member 74. Portion 118 of the upper member may substantially surround the bore and the load-sharing member, thereby allowing attachment of the upper and lower members. In an embodiment, the load-sharing member is a pin having a substantially circular cross-section. The pin preferably fits loosely within the bore such that its rotational freedom is maintained. The pin may be hinge pin 70 about which the upper member 72 pivots with respect to the lower member 74. The load-sharing member preferably contains an indention 114 forming a substantially planar surface about which the load-sharing member may be deflected.

A connector 112 preferably extends through an opening 116 in the end 50 of the strut. The connector preferably fixes the load-sharing member to the upper member 72 and may contact the load-sharing member at fulcrum point 126, which is preferably located on the planar surface formed by indention 114. Connector 122 is preferably a set screw, and opening 116 preferably contains threading for engaging the set screw. FIG. 18 depicts the strut in an "unloaded" position whereby a predetermined spacing 122 exists between upper member 72 and portion 120 of lower member 74. The predetermined spacing 122 may be adjusted by altering the location of connector 112 within opening 116. For instance, the screw may be rotated through opening 116 to increase spacing 122. The load-sharing member preferably remains substantially undeflected in the unloaded position.

Upon application of a compressive force onto the end 50 of the upper member 72, force is preferably imparted from connector 112 to the load-sharing member at fulcrum point 126. The compressive force is preferably sufficient to cause deflection of the load-sharing member and movement of upper member 72 toward portion 120 of the lower member such that predetermined spacing 122 is decreased. The deflection of the load-sharing member may force portion 118 of the upper member into a cavity 115 formed within the axial bore. The load-sharing member is preferably deflected in a three point bending arrangement as shown in FIG. 19.

FIG. 19 depicts the strut in the "loaded" position with the load-sharing member deflected. The predetermined spacing 22 is preferably adjustable and may be adjusted to set the maximum strain that can be imparted to the load-sharing member. When the load-sharing member has been deflected a vertical distance equal to predetermined spacing 22, the upper member 72 contacts portion 120, thereby inhibiting further strain on the load-sharing member. In this manner, the maximum amount of strain on the load-sharing member can be limited to reduce the possibility that the member will experience fatigue failure.

The load-sharing member may be constructed of any of a variety of metals or alloys. In a preferred embodiment, the load-sharing member is constructed of titanium or a titanium alloy. The material properties and cross-sectional area of the load-sharing member are preferably controlled to allow a predetermined amount of stress to occur across the fusion device. The horizontal distance 124 or moment arm between fulcrum point 126 and support point 128 on the lower member is preferably selected such that the fusion device has an "effective" modulus of elasticity in the vicinity of the modulus of elasticity of bone to facilitate bone development. The "effective" modulus of elasticity of the fusion device is taken to mean the ratio of stress to strain across the fusion device in a direction along height 20 as the device moves from the unloaded position to the loaded position upon receiving a compressive force. As described herein, "in the vicinity of the modulus of elasticity of bone" is taken to mean a Young's modulus between about 3 GPa and about 25 GPa. In an embodiment, the effective modulus of the fusion device is between about 16 GPa and about 20 GPa. The paper entitled "Variation of Young's Modulus and Hardness" in Human Lumbar Vertebrae Measured by Nanoindentation" by Marcel Roy and Jae-Young Rho (Department of Biomedical Engineering, University of Memphis, Memphis, Tenn.), and Ting Y. Tsui and George M. Pharr (Department of Materials Science, Rice University, Houston, Tex.) relates to the mechanical properties of bone and is incorporated by reference as if fully set forth herein.

The stresses exerted onto the spinal column are preferably shared by the fusion device and surrounding bone graft. As the spinal fusion develops, the proportion of stress experienced by the surrounding bone material preferably increases and the required load on the fusion device preferably decreases. After completion of the fusion, the fusion device preferably remains in the unloaded position during normal daily activity of the patient.

Fusion device 10 preferably provides a relatively large contact area between the engaging plates and the vertebral bodies defining the disc space occupied by the fusion device. FIG. 20 depicts a top view of an embodiment of a fusion device of the present invention. FIG. 21 depict a cross-sectional view of the fusion device taken along plane VI of FIG. 20. Depicted in FIGS. 22–24 is a conventional fusion cage such as that described in U.S. Pat. No. 4,961,740 to Ray et al. This patent is incorporated by reference as if fully set forth herein. The devices in FIGS. 20–24 are sized for use in the L3-L4 disc space of an average size middle-aged female. Dimensions of the fusion devices are indicated in millimeters.

The "effective contact area" between an engaging plate and a vertebral body may be calculated by subtracting the fenestration area, a (i.e., the combined area of the openings 34 intended for bone ingrowth), from the total contact area, A (the area of the face 15 including the area of the openings 34). The total contact area and the fenestration area of the fusion device in FIGS. 20 and 21 is 581 mm$^2$ and 96 mm$^2$, respectively. Therefore, the effective contact area between the engaging plate and the vertebra is 485 mm$^2$.

For the fusion cage depicted in FIGS. 22–24, it is assumed that threads on the outer surface of the fusion cage penetrate into the vertebra a total of 3 mm per side as recommended by the manufacturer. It should be noted that such penetration is often difficult to achieve. In addition, the cortical layer of a vertebral body is often only 1–2 mm thick. Each of the cylindrical elements of the fusion cage has a total contact area of 283.5 mm$^2$ and a fenestration area of 198.5 mm$^2$. Therefore, the combined effective contact area of both of the cylindrical elements is 170 mm$^2$. If the threads of the fusion cage penetrate into the vertebra a distance less than 3 mm per side, the contact area will be less than that calculated above.

The maximum axial compressive forces in the lumbar spine resulting from everyday activity were estimated to be 3200 N in a paper entitled "The BAK™ Interbody Fusion: An Innovative Solution" by Bagby et al. and available from Spine Tech, Inc. in Minneapolis Minn. (see page 3, bottom paragraph). For a 3200 N compressive force, the stress per unit area is calculated to be 18.8 N/mm$^2$ for the fusion cage depicted in FIGS. 22–24 as compared to 6.6 N/mm$^2$ for the fusion device depicted in FIG. 20 and FIG. 21. It is believed that such a reduction in stress per unit area will result in a significant reduction in post surgical subsidence at the interface of the fusion device and vertebral body. Typically, the loss of disc height is estimated to be about 1–3 mm at one month follow-up when conventional devices such as that depicted in FIGS. 22–24 are employed.

Further Improvements

Figure 25:
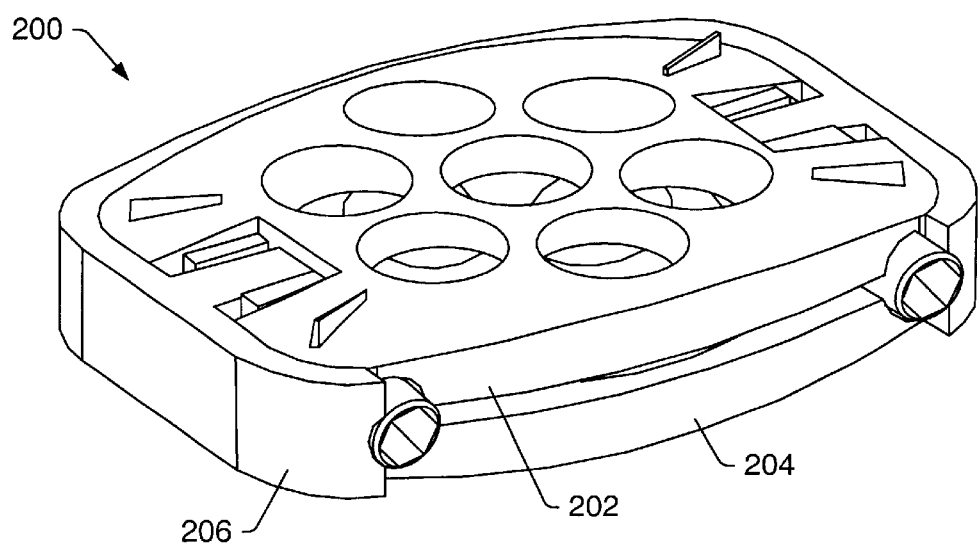
FIG. 25 depicts a perspective view of a fusion device in the lowered position, the fusion device including a pair of turnbuckles oriented perpendicular to the anterior and posterior edges of the fusion device.
Figure 26:
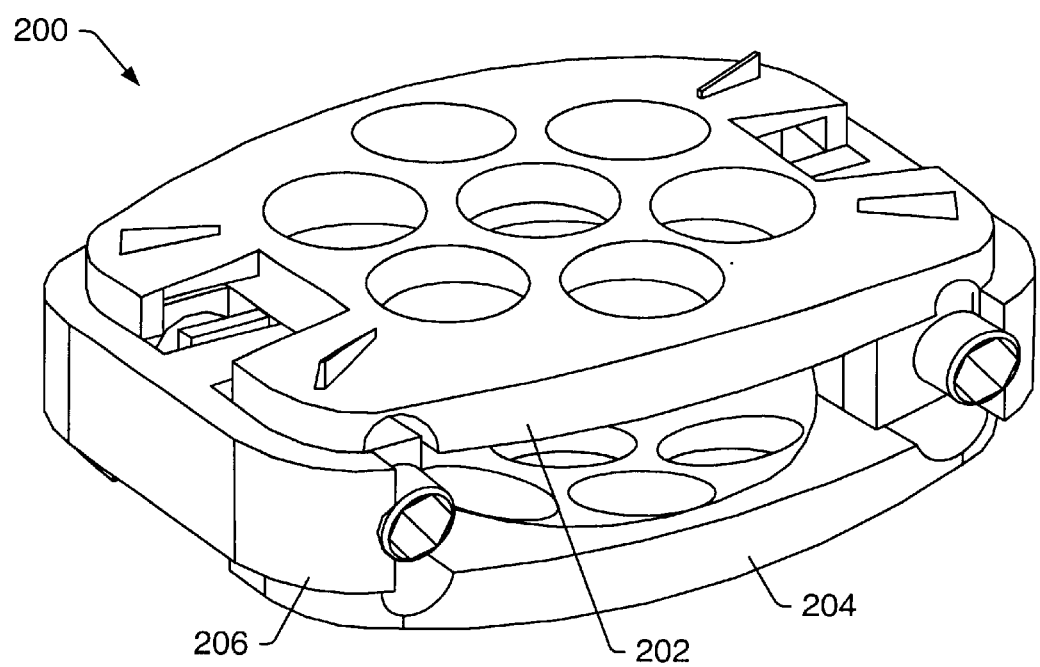
FIG. 26 depicts a perspective view of the fusion device of FIG. 25 in the raised position.
Figure 27:
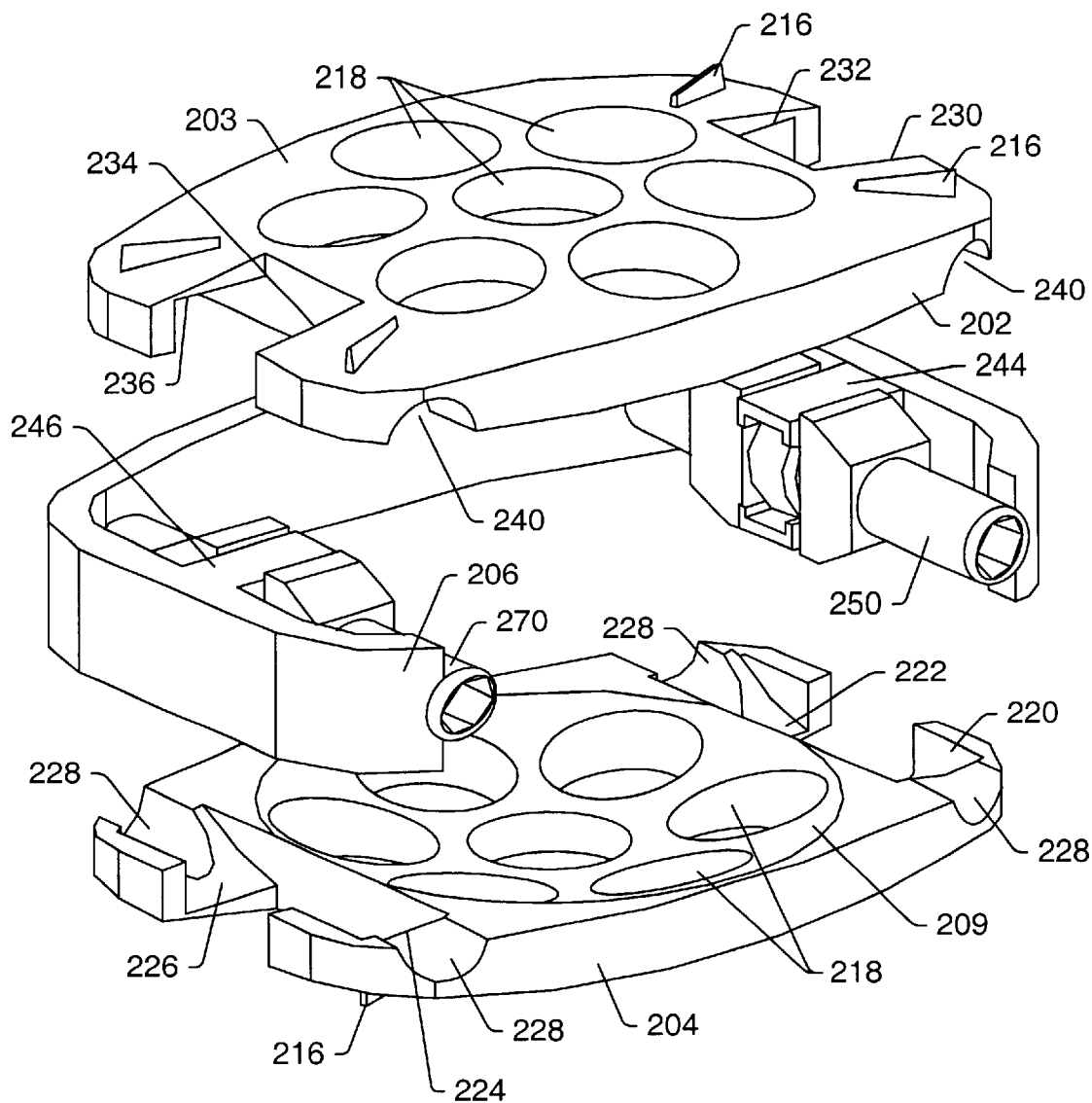
FIG. 27 depicts an exploded view of the fusion device of FIG. 25.

An alternate embodiment of an interbody fusion device is depicted in FIGS. 25–27. FIG. 25 is a perspective view of the fusion device in a lowered position. FIG. 26 is a perspective view of the fusion device in a raised position. FIG. 27 is an exploded view of the fusion device. Fusion device 200 includes a pair of engaging plates 202 and 204 for engaging adjacent vertebrae. Engaging plates 202 and 204 are preferably separated by bracket assembly 206. Engaging plates 202 and 204 and bracket assembly 206 may be formed of titanium, stainless steel, polymer, ceramic, composite material, or any other biocompatible material. For purposes of this description, "biocompatible material" is material not rejected by the body and/or not causing infection following implantation.

As depicted in FIG. 27, engaging plates 202 and 204 may contain a plurality of protrusions 216 from outer surfaces 203 for enhancing an engagement between the vertebrae and the engaging plates. In this manner, subsidence of the vertebrae may be substantially prevented as previously described. Outer surfaces 203 are preferably substantially planar to provide a large contact area between the engaging plates and the vertebrae; alternately, outer surfaces 203 may be non-planar. Protrusions 216 may extend into the vertebrae to prevent the fusion device from moving out of the disc space. Engaging plates 202 and 204 may include a plurality of openings 218 to allow bone development and growth through the engaging plates and between fusion device 200 and the neighboring vertebrae. In an embodiment, openings 218 have a combined area that is greater than about 50% of the total area of outer surfaces 203 (including the area of openings 218). More preferably, openings 218 have a total area between 60% and 80% of the total area of outer surfaces 203. More preferably still, openings 218 have a total area of 70% or more of the total area of outer surfaces 203.

Bracket assembly 206 (depicted in perspective view in FIG. 28) preferably includes an alignment device for changing a height. between engaging plates 202 and 204. In an embodiment, the alignment device includes first turnbuckle 250 and second turnbuckle 270 positioned substantially parallel to and substantially adjacent first side edge 212 and second side edge 214, respectively, and extending between anterior edge 208 and posterior edge 210. Bracket assembly 206 includes lateral projections 244 and 246 extending into the interior of the bracket assembly and supporting turnbuckles 250 and 270, respectively. The turnbuckles include middle portions (e.g., middle portion 256 of turnbuckle 250) disposed between the ends of the turnbuckles and having a diameter greater than a diameter of the threaded portions. Lateral projection 244 is sized such that middle portion 256 is retained within lateral projection 244 while turnbuckle 250 is free to rotate within lateral projection 244. Ends 296 of bracket assembly 206 (shown in detail in FIG. 29A) may include arcuate grooves 297 which correspond to the curvature of turnbuckles 250 and 270. Inner surface 209 (FIG. 27) of engaging plates 204 and the inner surface of engaging plate 202 (not readily visible in FIG. 27) also may include arcuate grooves 228 and 240 (FIG. 27), respectively, which correspond to the curvature of turnbuckles 270 and 250.

Returning to FIG. 28, first threaded portion 252 of first turnbuckle 250 is preferably threaded in a first direction and second threaded portion 254 of first turnbuckle 250 is preferably threaded in a direction opposite the first direction. First threaded portion 272 of second turnbuckle 270 is preferably threaded in a second direction and second threaded portion 274 of second turnbuckle 270 is preferably threaded in a direction opposite the second direction. First threaded portions 252 and 272 may be threaded in the same direction or in opposite directions. First turnbuckle 250 is preferably configured to be coupled to cam blocks 260 and 261; second turnbuckle 270 is preferably configured to be coupled to cam blocks 280 and 281. Cam block 260 is preferably coupled to first turnbuckle 250 through opening 266 (FIG. 29B). Opening 266 is preferably threaded complementarily to first portion 252 of first turnbuckle 250. Cam blocks 261, 280, and 281 are preferably similarly configured for coupling to turnbuckle portions 254, 272, and 274, respectively.

Cam block 260 preferably includes upper surface 262 having a first slope and lower surface 264 having a second slope (FIG. 29C); cam blocks 261, 280, and 281 are preferably similarly configured. The slopes of corresponding features on paired cam blocks (e.g., the slopes of upper surface 262 of cam block 260 and upper surface 263 of cam block 261) are preferably equivalent. Alternatively, the slopes of corresponding features on paired cam blocks may differ. In addition, the slope of upper surface 262 of cam block 260 need not be equivalent to the slope of lower surface 264 of cam block 260. Further, the slope of upper surface 262 of cam block 260 need not be equivalent to the slope of upper surface 282 of cam block 280, to the slope of upper surface 283 of cam block 281, or to the slopes of the lower surfaces of cam blocks 280 and 281 (not visible in FIG. 28).

Referring to FIG. 27, inner surface 209 of engaging plate 204 preferably includes sloped tracks 220, 222, 224, and 226. Sloped tracks 220, 222, 224, and 226 are preferably constructed such that the slopes of sloped tracks 220, 222, 224, and 226 are substantially equivalent to the slopes of lower surface 264 of cam block 260 and to the lower surfaces of cam blocks 261, 280, and 281, respectively. The inner surface of engaging plate 202 also preferably includes sloped tracks 230, 232, 234, and 236 (the ends of which are visible in FIG. 27). Sloped tracks 230, 232, 234, and 236 are preferably constructed such that the slopes of sloped.tracks 230, 232, 234, and 236 are substantially equivalent to the slopes of upper surfaces 262, 263, 282, and 283 (FIG. 28), respectively, of cam blocks 260, 261, 280, and 281.

Figure 28:
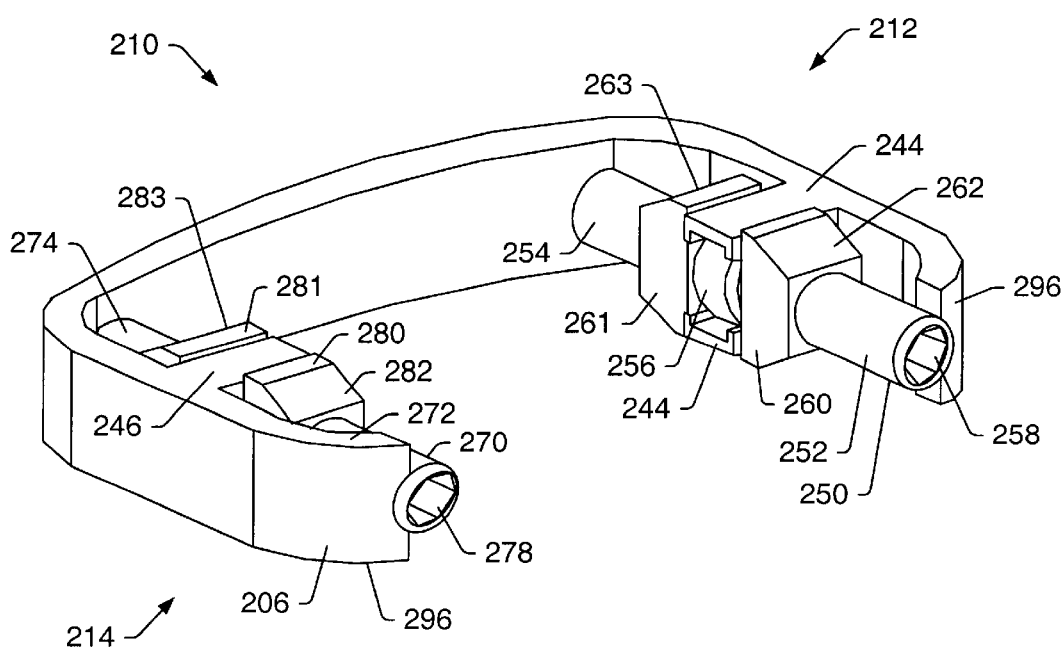
FIG. 28 depicts a perspective view of a bracket assembly of the fusion device of FIG. 25.
Figure 29A:
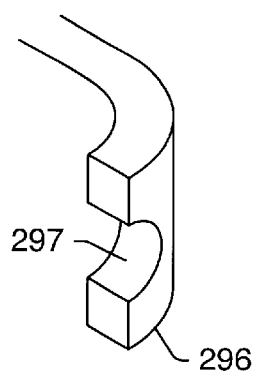
FIG. 29a depicts a perspective view of the end of the bracket assembly of FIG. 25.
Figure 29B:
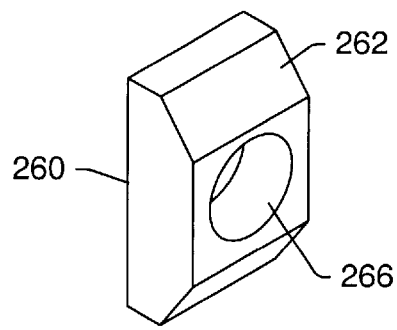
FIG. 29b depicts a perspective view of a cam block of the fusion device of FIG. 25.

Referring to FIG. 28, turnbuckles 250 and 270 may still further include indentations 258 and 278. Indentations 258 and 278 may be configured to receive the tip of an adjusting tool (not shown). The adjusting tool may be a screwdriver. In a preferred embodiment, the adjusting tool is an alien wrench. The adjusting tool may be used to rotate the turnbuckles. Rotation of first turnbuckle 250 in a first angular direction (e.g., clockwise or counterclockwise) may cause cam blocks 260 and 261 to move away from each other; rotation of first turnbuckle 250 in an angular direction opposite the first angular direction may cause cam blocks 260 and 261 to move toward each other. Rotation of second turnbuckle 270 in a second angular direction may cause cam blocks 280 and 281 to move away from each other; rotation of second turnbuckle 270 in an angular direction opposite the second angular direction may cause cam blocks 280 and 281 to move toward each other. The second angular direction may be the same as the first angular direction; alternatively, the second angular direction may be opposite the first angular direction. The turnbuckles are preferably fixed with respect to the bracket assembly. As shown in FIGS. 25–28, rotation of a fixed turnbuckle in a first direction will cause cam blocks coupled to the turnbuckle and having threading complementary to the threading of the turnbuckle to move. Because the ends of the turnbuckle are threaded in opposite directions, the cam blocks will move laterally in opposite directions.

Figure 30A:
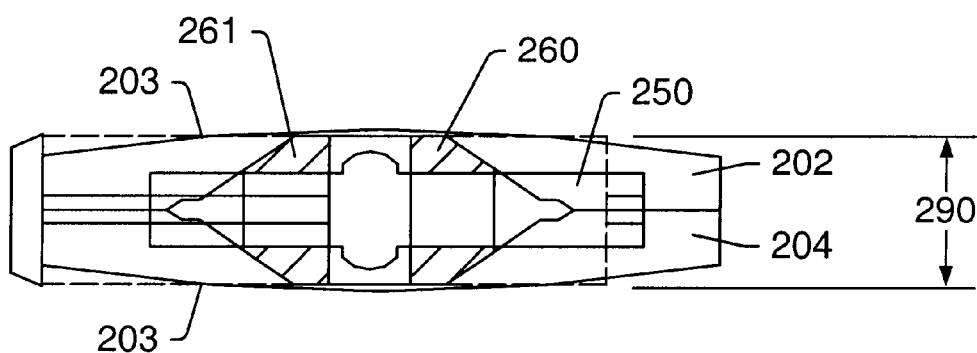
FIG. 30a depicts a cutaway view of the fusion device of FIG. 25 in a lowered position.
Figure 30B:
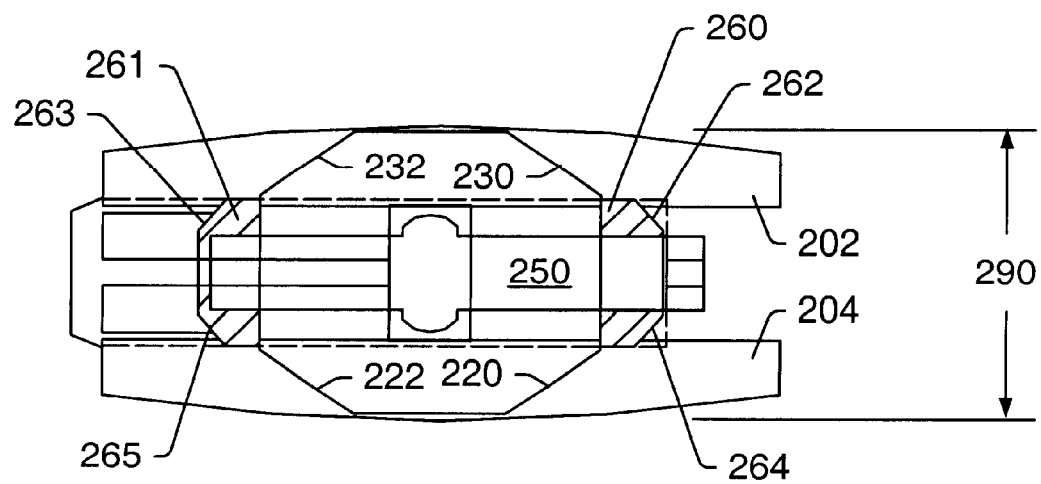
FIG. 30b depicts a cutaway view of the fusion device of FIG. 25 in a raised position.

As depicted in FIGS. 25–28, the cam blocks and sloped tracks are preferably constructed such that motion of the cam blocks toward the edges of the engaging plates causes the separation distance between the engaging plates to increase. FIGS. 30A and 30B depicts a cutaway view of interbody fusion device 200 in a lowered position and a raised position, respectively. Sloped tracks 230, 232, 220, and 222 correspond to the slopes of cam block surfaces 262, 263, 264, and 265, respectively. In order for the cam blocks to move laterally toward the exterior of the fusion device, as shown in FIGS. 30A and 30B, the interior separation distance between engaging plates 202 and 204 must be increased to accommodate the height of the cam blocks. Increasing the interior separation distance in turn increases the height 290 of the device, shown as distance from exterior surface 203 of one engaging plate to exterior surface 203 of another engaging plate. Rotation of turnbuckle 250 in a first direction causes lateral motion of cam blocks 260 and 261 toward the anterior or posterior edges of interbody fusion device 200. Because the slopes of surfaces 262, 263, 264, and 265 of the cam blocks match the slopes of sloped tracks 230, 232, 220, and 222, the lateral motion of the cam blocks forces engaging plates 202 and 204 apart and increases height 290. Rotation of turnbuckle 250 in a direction opposite the first direction will cause the cam blocks to move toward each other, decreasing height 290.

Figure 31A:
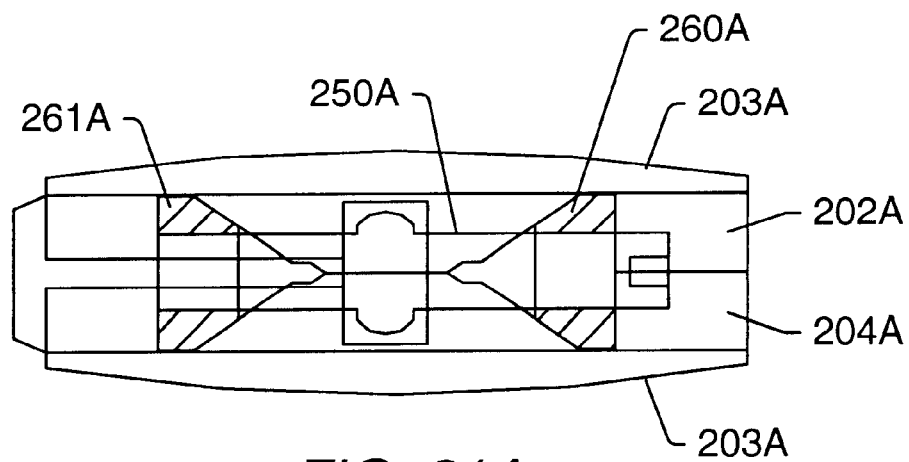
FIG. 31a depicts a cutaway view of an alternative configuration of the fusion device of FIG. 25 in a lowered position.
Figure 31B:
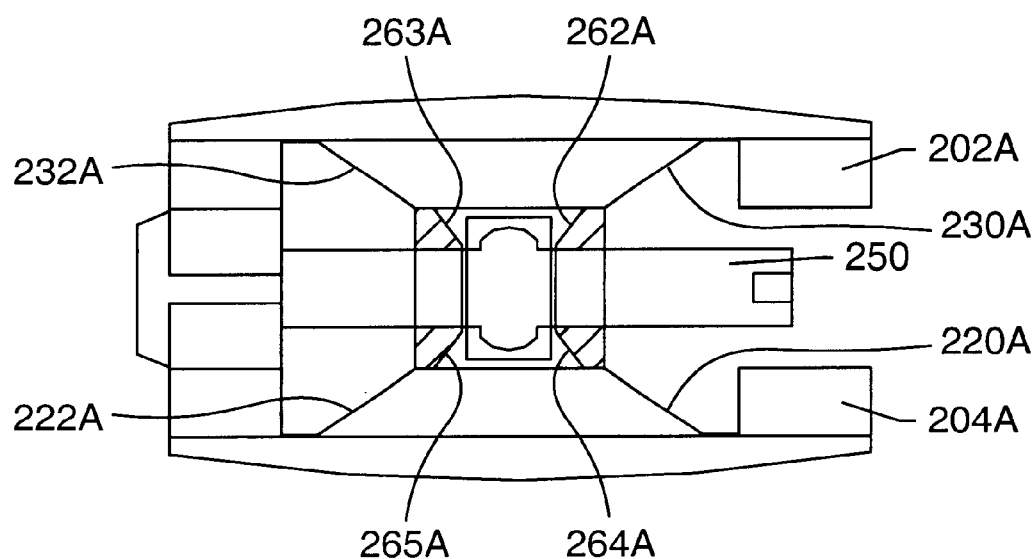
FIG. 31b depicts a cutaway view of an alternative configuration of the fusion device of FIG. 25 in a raised position.

The cam blocks and sloped tracks, however, may be constructed such that motion of the cam blocks away from the edges of the engaging plates causes the distance between the engaging plates to increase, as depicted in FIGS. 31A and 31B. Features of the interbody fusion device are labeled with the suffix "A" in FIGS. 31A and 31B to denote the alternate configuration (e.g., cam block 260A is similar to cam block 260 except for the orientation). As depicted in FIGS. 31A and 31B, rotation of turnbuckle 250A in a first direction causes lateral motion of cam blocks 260A and 261A toward the interior of interbody fusion device 200A. Because the slopes of surfaces 262A, 263A, 264A, and 265A of the cam blocks match the slopes of sloped tracks 230A, 232A, 220A, and 222A, the lateral motion of the cam blocks forces engaging plates 202A and 204A apart, increasing height 290A from surface 203A of one engaging plate to surface 203A of another engaging plate. Rotation of turnbuckle 250A in a direction opposite the first direction will cause. the cam blocks to move toward the anterior or posterior edges of the fusion device, decreasing height 290A.

Figure 32A:
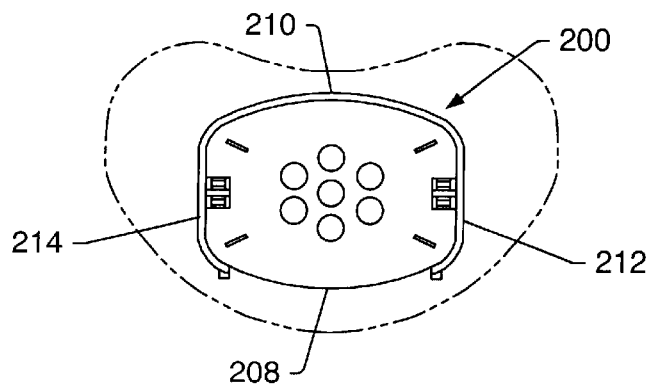
FIG. 32a depicts a top view of the alignment device of FIG. 25 in use.
Figure 32B:
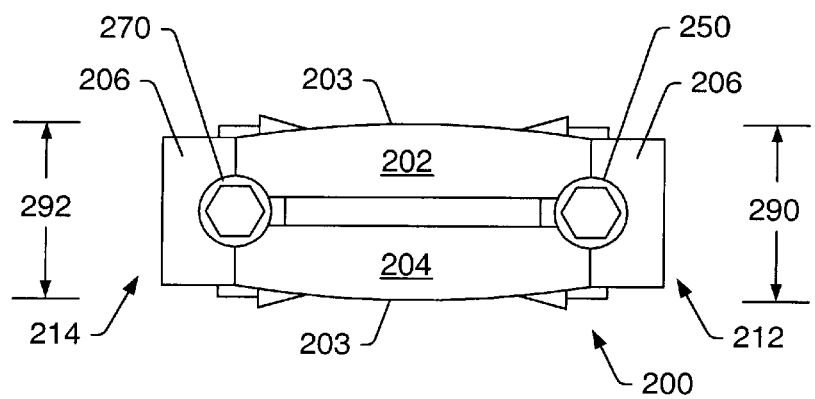
FIG. 32b depicts a front view of the alignment device of FIG. 25 in use in a lowered position.
Figure 32C:
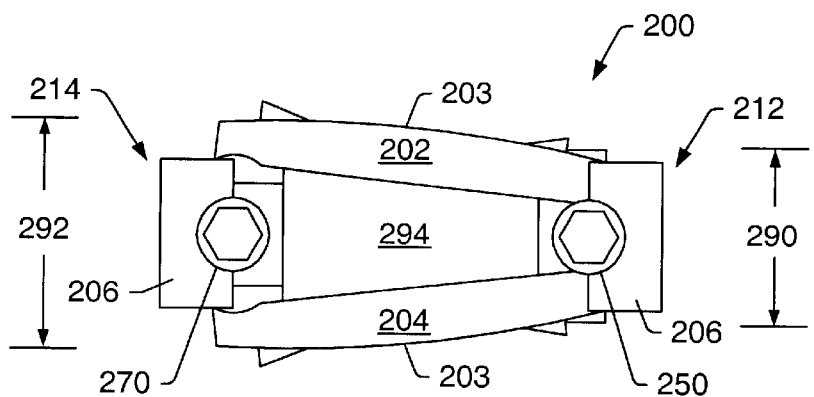
FIG. 32c depicts a front view of the alignment device of FIG. 25 in use in a raised position.

FIG. 32A is a top view of fusion device 200 as inserted between two vertebrae (shown in phantom). Anterior edge 208, posterior edge 210, first side edge 212, and second side edge 214 are indicated in FIG. 32A. FIG. 32B is a front (anterior) view of alignment device 200 in a lowered position. Height 290 (the distance from the outer surface of engaging plate 202 to the outer surface of engaging plate 204 at a location lying on first side edge 212 a specified distance from anterior edge 208) and height 292 (the distance from the outer surface of engaging plate 202 to the outer surface of engaging plate 204 at a location lying on second side edge 214 the same specified distance from anterior edge 208) are substantially equivalent when alignment device 200 is in the lowered position as pictured. First turnbuckle 250 and second turnbuckle 270 may be rotated independently of one another to independently adjust heights 290 and 292 to correct a lateral deviation of the spine, as depicted in FIG. 32C. Heights 290 and 292 may be substantially uniform between anterior edge 208 and posterior edge 210 (e.g., when the slopes of upper surfaces 262 and 263 of cam blocks 260 and 261 (depicted in FIG. 28) are substantially equivalent). Alternatively, heights 290 and 292 may be substantially different proximate anterior edge 208 than proximate posterior edge 210 to maintain a substantially natural lordosis of the spine (e.g., when the slope of surface 262 is substantially different from the slope of surface 263).

Referring to FIG. 32C, bone graft material 294 may be packed between engaging plates 202 and 204. A removable endcap (not shown) similar to endcap 25 (FIG. 4B) may be positioned proximate anterior edge 208 to contain bone graft material 294 within the fusion device and to prevent migration of the bone graft outside the engaging plates. The removable endcap may contain one or more openings for allowing bone ingrowth between a vertebral body and bone graft contained between the engaging plates. The removable endcap is preferably made of a plastic material such as polyethylene that tends to be non-irritating and non-abrasive to the surrounding tissues.

To install the fusion device, a discectomy is preferably performed from an anterior approach. All cartilage and soft tissue are preferably removed from the vertebral endplate as would normally be done for placement of a femoral strut graft. Such a procedure is well within the knowledge of a skilled practitioner of the art. The engaging plates may be deployed in the disc space between the adjacent vertebrae. Turnbuckles 250 and 270 may be rotated to achieve the desired heights 290 and 292 from outer surface 203 of engaging plate 202 to outer surface 203 of engaging plate 204 at first side edge 212 and second side edge 214. The proper heights may be determined beforehand using x-ray techniques in which the side portions of the intervertebral disc space are examined.

Figure 33:
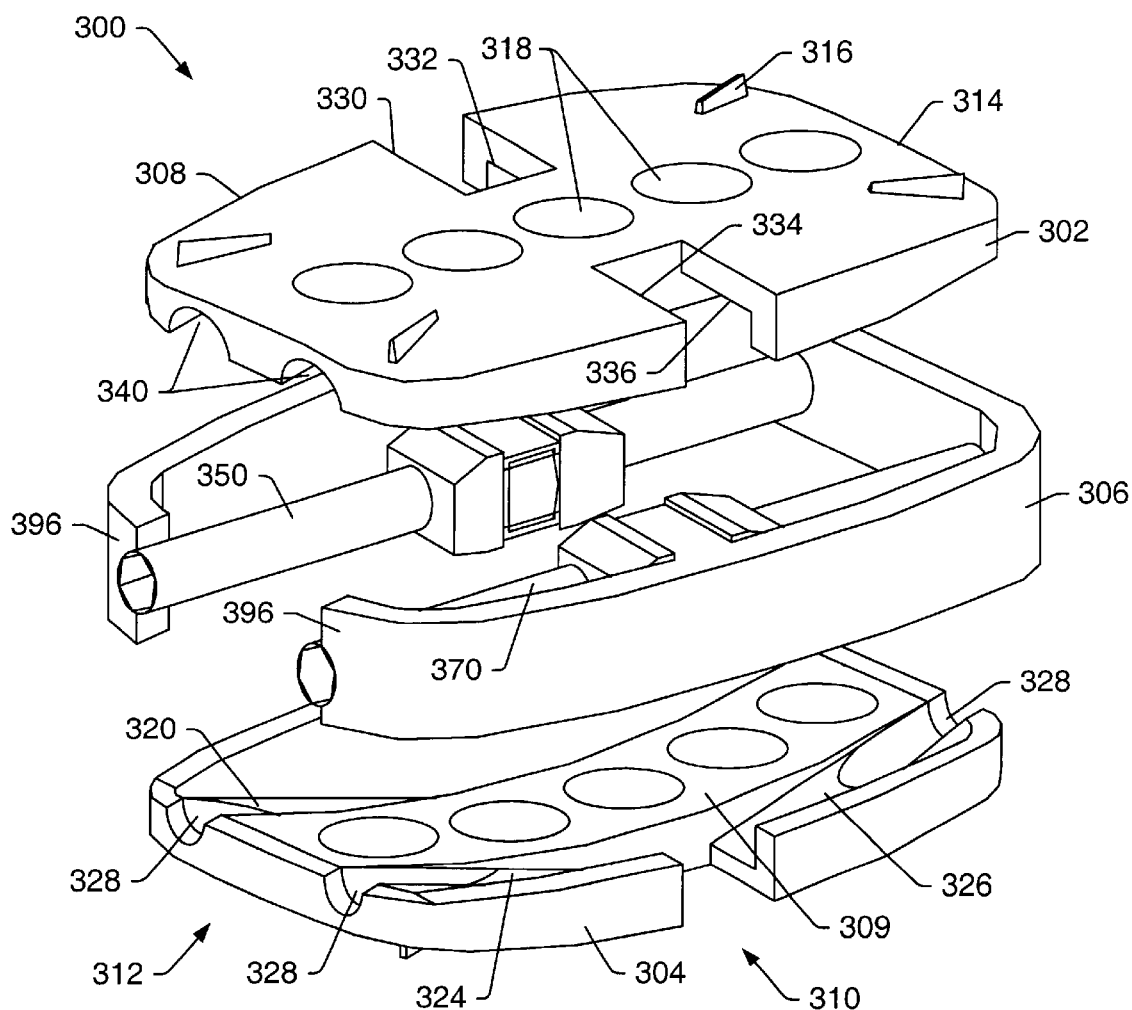
FIG. 33 depicts an exploded view of a fusion device including a pair of turnbuckles oriented parallel to the anterior and posterior edges of the fusion device.

FIG. 33 is an exploded view of an alternate embodiment of an interbody fusion device. Interbody fusion device 300 preferably includes engaging plates 302 and 304 and bracket assembly 306. Engaging plates 302 and 304 and bracket assembly 306 may be formed of titanium, stainless steel, polymer, ceramic, composite material, or any other biocompatible material. Engaging plates 302 and 304 may include protrusions 316 and openings 318. Bracket assembly 306 is depicted in perspective view in FIG. 34. First turnbuckle 350 and second turnbuckle 370 are preferably positioned substantially parallel to and substantially adjacent anterior edge 308 and posterior edge 310, respectively, of interbody fusion device 300 and extend between first side edge 312 and second side edge 314.

Figure 34:
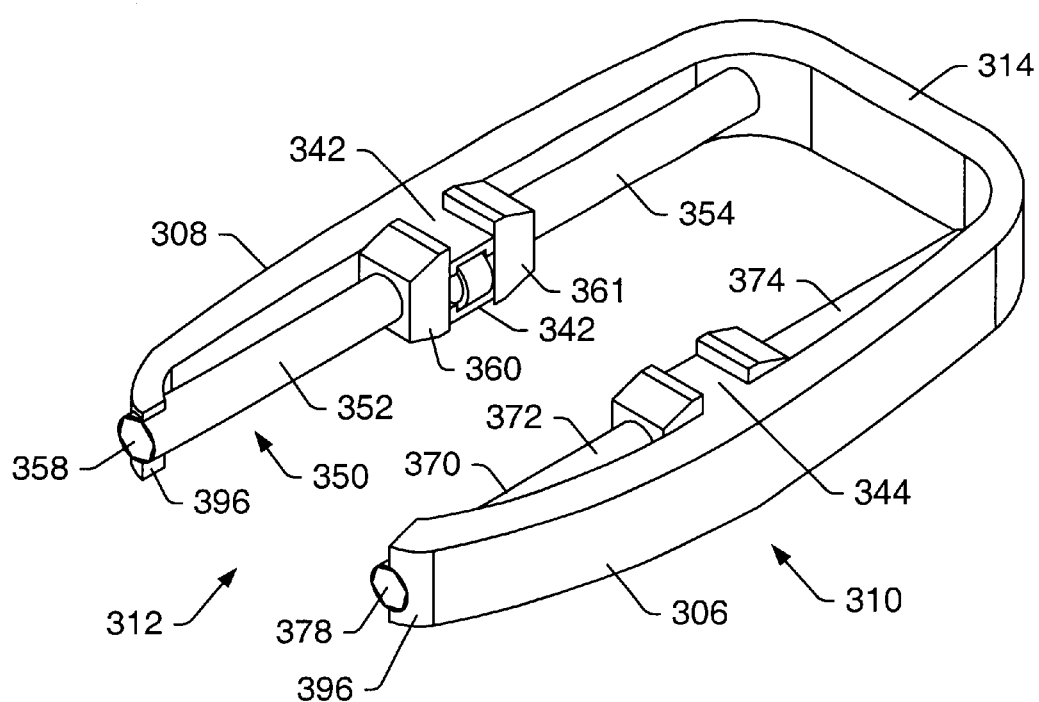
FIG. 34 depicts a perspective view of the bracket assembly of the fusion device of is FIG. 32.

Interbody fusion device 300 as depicted is similar to interbody fusion device 200 depicted in FIGS. 25–28 except for the orientation of the adjusting mechanism. Thus, first turnbuckle 350 is preferably coupled to cam blocks 360 and 361 at first and second threaded portions 352 and 354, respectively; second turnbuckle 370 is preferably coupled to cam blocks 380 and 381 at first and second threaded portions 372 and 374, respectively (FIG. 34). Cam blocks 360 and 361 may contact engaging plate 302 in sloped tracks 330 and 332, respectively (the ends of which are visible in FIG. 33); cam blocks 360 and 361 may contact engaging plate 304 in sloped track 320 and in a sloped track (not visible) similar to sloped track 320, respectively. Cam blocks 380 and 381 may contact engaging plate 302 in sloped tracks 334 and 336, respectively (the ends of which are visible in FIG. 33); cam blocks 380 and 381 may contact engaging plate 304 in sloped tracks 324 and 326, respectively. Inner surface 309 (FIG. 33) of engaging plate 304 and the inner surface of engaging plate 302 (not readily visible in FIG. 33) also may include arcuate grooves 328 and 340, respectively, which correspond to the curvature of turnbuckles 370 and 350. First turnbuckle 350 may contact bracket assembly 306 at lateral projection 342 and second turnbuckle 370 may contact bracket assembly 306 at lateral projection 344 (FIG. 34). In addition, the turnbuckles may contact bracket assembly 306 in arcuate grooves (similar to arcuate grooves 297 in FIG. 29A) in ends 396.

Adjustment of the distance between engaging plates 302 and 304 by rotation of turnbuckles 350 and 370 is preferably similar to the adjustment process by rotation of turnbuckles 250 and 270 as previously described for interbody fusion device 200. Distances between engaging plates 302 and 304 along anterior edge 308 and along posterior edge 310 may be varied substantially independently to maintain a substantially natural lordosis. In addition, slopes of upper and lower surfaces of the cam blocks may be unequal such that distances between engaging plates 302 and 304 along first side edge 312 and second side edge 314 may vary between anterior edge 308 and posterior edge 310 to maintain a substantially natural lateral alignment.

Figure 35:
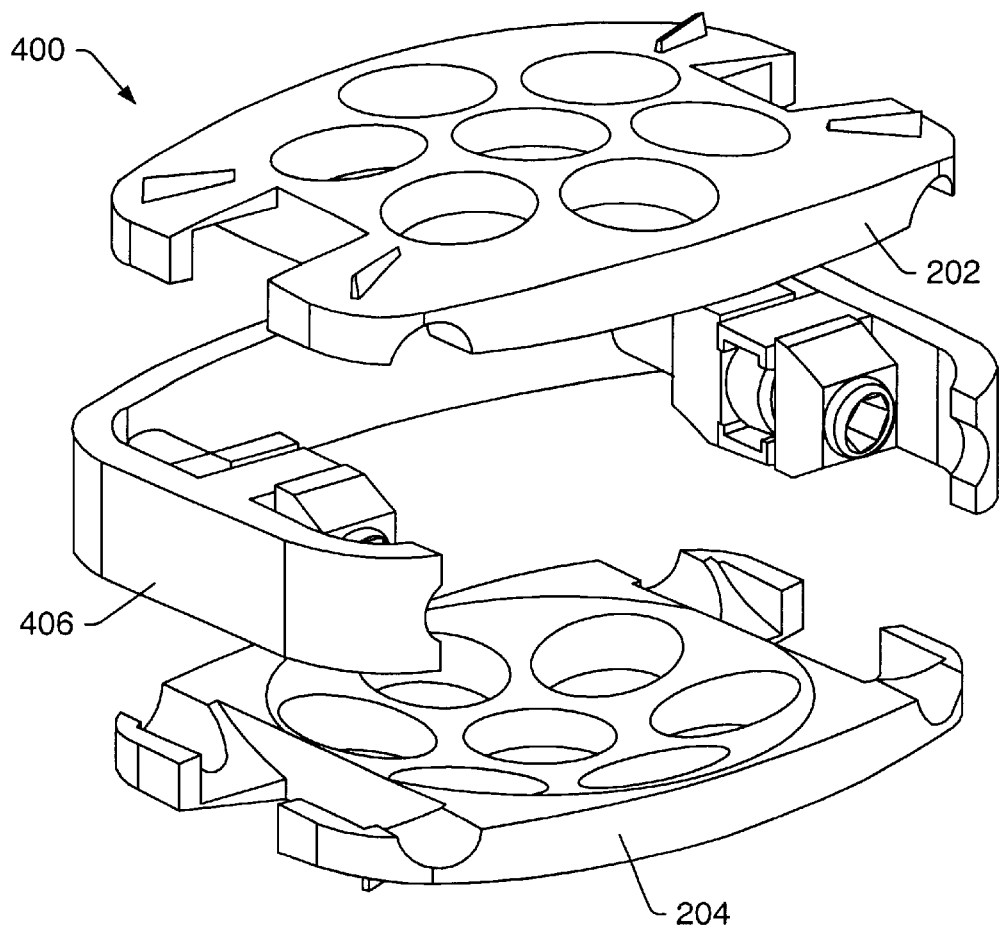
FIG. 35 depicts an exploded view of a fusion device including a pair of screws, each of which is threaded through a pair of cam blocks.
Figure 36:
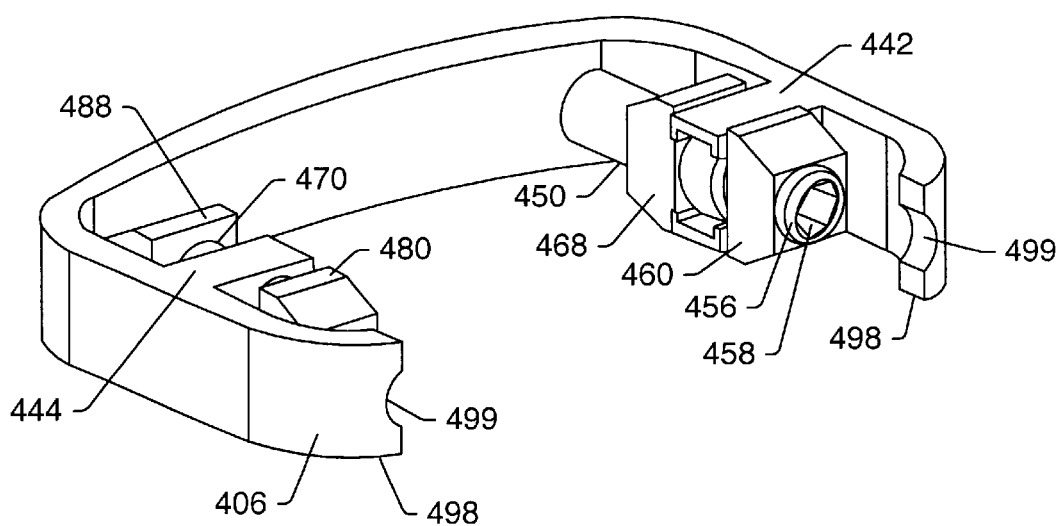
FIG. 36 depicts a perspective view of the alternative bracket assembly of the fusion device of FIG. 34.
Figure 37A:
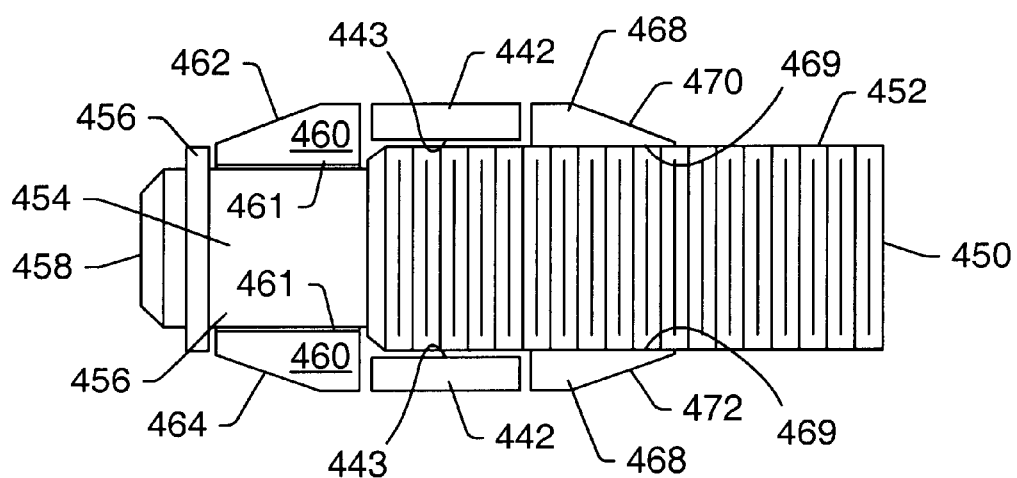
FIG. 37a depicts a cross-sectional view of the screws and cam blocks of FIGS. 35–36 in use in a first position.

FIG. 35 is an exploded view of interbody fusion device 400, which includes engaging plates 202 and 204 (see FIGS. 25–27) and bracket assembly 406. Engaging plates 202 and 204 and bracket assembly 406 may be formed of titanium, stainless steel, polymer, ceramic, composite material, or any other biocompatible material. FIG. 36 is a perspective view of alternative bracket assembly 406 which may be placed between engaging plates 202 and 204. Lateral projections 442 and 444 of bracket assembly 406 may support screws 450 and 470, respectively. FIG. 37A depicts a cross-sectional view of screw 450. Screw 450 preferably includes threaded portion 452 and unthreaded portion 454. A diameter of threaded portion 452 may be greater than a diameter of unthreaded portion 454. Cam block 460 may include an opening such that inner surface 461 of the opening is substantially unthreaded. Unthreaded portion 454 of screw 450 may then be free to rotate within cam block 460. Cam block 468 may include an opening such that inner surface 469 of the opening is threaded complementarily to threaded portion 452 of screw 450. Projection 442 of bracket assembly 406 may also include openings with inner surfaces 443 threaded complementarily to threaded portion 452 of screw 450.

Screw 450 may further include flange 456. A diameter of flange 456 may be substantially greater than a diameter of unthreaded portion 454. Flange 456 may maintain coupling between cam block 460 and unthreaded portion 454 of screw 450. Screw 450 may still further include indentation 458. Indentation 458 may be configured to receive the tip of an adjusting tool (not shown). The adjusting tool may be a screwdriver. In a preferred embodiment, the adjusting tool is an allen wrench. Ends 498 of bracket assembly 406 may include arcuate grooves 499 to allow access of the adjusting tool to indentations 458 and 478 (shown in FIG. 36) of screws 450 and 470, respectively.

Figure 37B:
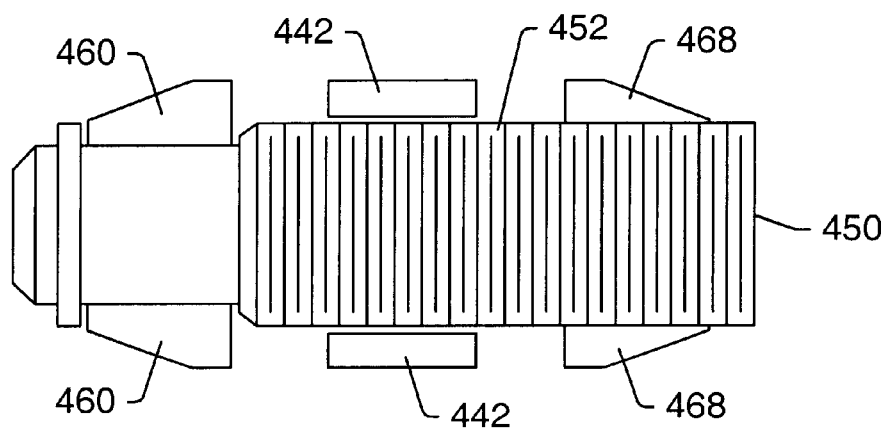
FIG. 37b depicts a cross-sectional view of the screws and cam blocks of FIGS. 35–36 in use in a second position.

Rotation of screw 450 in a first angular direction may cause cam blocks 460 and 468 to move away from each other, as depicted in FIG. 37B. Rotation of screw 450 in an angular direction opposite the first angular direction may cause cam blocks 460 and 468 to move toward one another, as depicted in FIG. 37A. Alternatively, rotation of screw 450 in a first angular direction may cause cam blocks 460 and 468 to move toward each other, and rotation of screw 450 in an angular direction opposite the first angular direction may cause cam blocks 460 and 468 to move away from one another. Screw 470, cam blocks 480 and 488, and lateral projection 444 (FIG. 36) may possess features similar to those of screw 450, cam blocks 460 and 468, and lateral projection 442, respectively.

Distances between engaging plates 402 and 404 along first side edge 412 and along second side edge 414 may be varied substantially independently to maintain a substantially natural lateral alignment. In addition, slopes of upper and lower surfaces of the cam blocks may be unequal such that distances between engaging plates 402 and 404 along anterior edge 408 and posterior edge 410 may vary between first side edge 412 and second side edge 414 to maintain a substantially natural lordosis.

Figure 38:
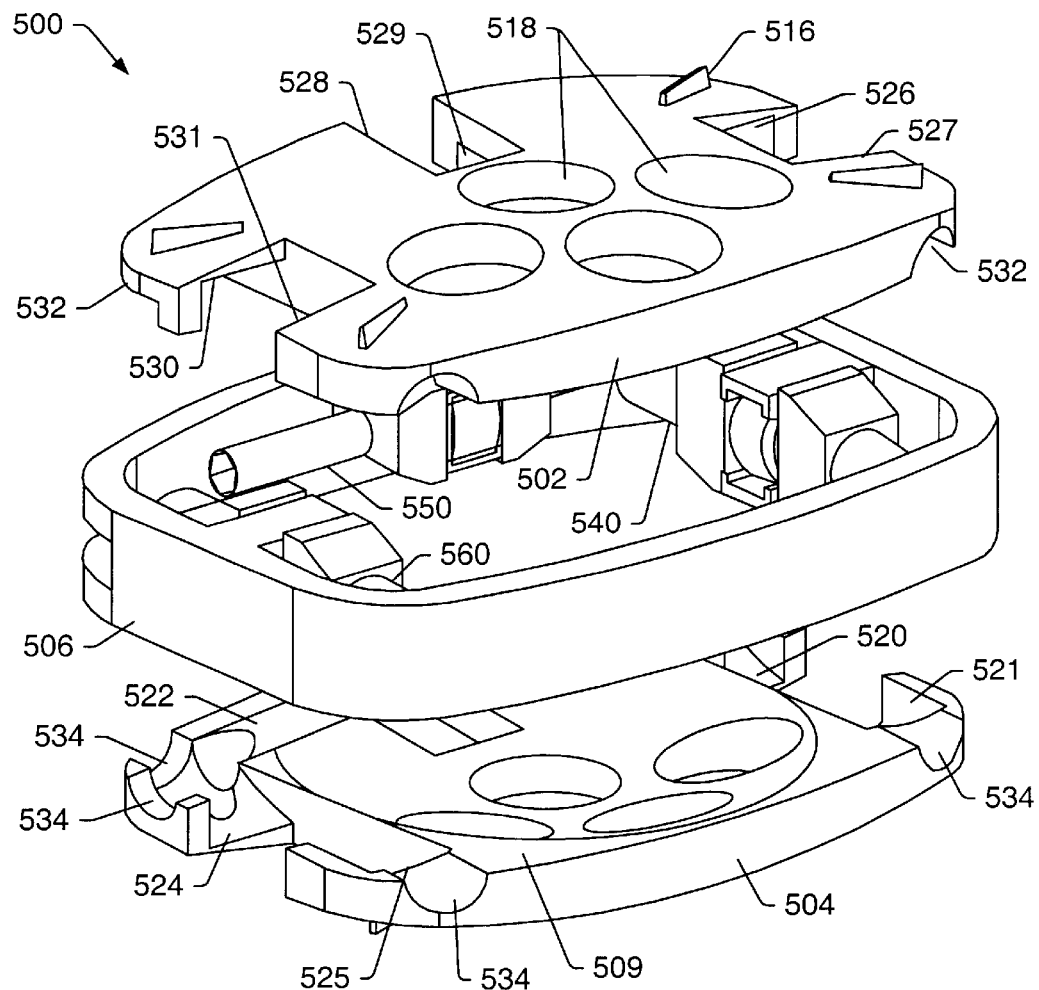
FIG. 38 depicts an exploded view of a fusion device including three turnbuckles.

An alternate embodiment of an interbody fusion device is depicted in an exploded view in FIG. 38. Interbody fusion device 500 preferably includes engaging plates 502 and 504 and bracket assembly 506. Engaging plates 502 and 504 and bracket assembly 506 may be formed of titanium, stainless steel, polymer, ceramic, composite material, or any other biocompatible material. Engaging plates 502 and 504 may include protrusions 516 and openings 518. Bracket assembly 506 (depicted in perspective view in FIG. 39) may include an alignment device for changing a height between engaging plates 502 and 504. In an embodiment, the alignment device includes first turnbuckle 540 positioned substantially parallel to and substantially adjacent second side edge 514, second turnbuckle 550 positioned substantially parallel to and substantially adjacent anterior edge 508, and third turnbuckle 560 positioned substantially parallel to and substantially adjacent first side edge 512. Bracket assembly 506 may include lateral projections 584, 586, and 588 extending into the interior of the bracket assembly and supporting turnbuckles 540, 550, and 560, respectively. The turnbuckles may include middle portions (e.g., middle portions 543 and 553 of turnbuckles 540 and 550, respectively) disposed between the ends of the turnbuckles and having a diameter greater than a diameter of the threaded portions. Lateral projections 584, 586, and 588 are preferably sized such that the middle portions are retained within the lateral projections while the turnbuckles are free to rotate within the lateral projections. Inner surface 509 of engaging plate 504 (FIG. 38) and the inner surface of engaging plate 502 (not readily visible in FIG. 38) may include arcuate grooves 534 and 532, respectively, which correspond to the curvature of turnbuckles 540, 550, and 560.

Returning to FIG. 39, first threaded portion 541 of first turnbuckle 540 may be threaded in a first direction and second threaded portion 542 of first turnbuckle 540 may be threaded in a direction opposite the first direction. First threaded portion 551 of second turnbuckle 550 may be threaded in a second direction and second threaded portion 552 of second turnbuckle 550 may be threaded in a direction opposite the second direction. First threaded portion 561 of third turnbuckle 560 may be threaded in a third direction and second threaded portion 562 of third turnbuckle 560 may be threaded in a direction opposite the third direction. First threaded portions 541, 551, and 561 may be threaded in the same direction; alternatively, one of the first threaded portions may be threaded in a direction opposite the direction of the other two fist threaded portions.

Figure 29C:
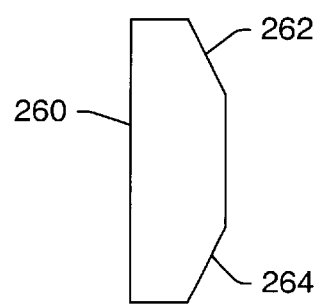
FIG. 29c depicts a side view of the cam block of FIG. 29b.

First turnbuckle 540 is preferably configured to be coupled to cam blocks 544 and 545. Second turnbuckle 550 is preferably configured to be coupled to cam blocks 554 and 555. Third turnbuckle 560 is preferably configured to be coupled to cam blocks 564 and 565. The cam blocks are preferably coupled to the turnbuckles as depicted for cam block 260 and turnbuckle 250 (FIG. 29B). The surfaces of cam blocks 544, 545, 554, 555, 564, and 565 are preferably sloped as previously described for cam block 236 (FIG. 29C).

Inner surface 509 of engaging plate 504 preferably includes sloped tracks (e.g., 520, 521, 522, 524, and 525 visible in FIG. 38) configured to correspond to the lower surfaces of cam blocks 544, 545, 554, 555, 564, and 565, respectively. The inner surface of engaging plate 502 preferably also includes sloped tracks 526, 527, 528, 529, 530, and 531 (the ends of which are visible in FIG. 38) configured to correspond to the upper surfaces of cam blocks 544, 545, 554, 555, 564, and 565, respectively.

Figure 39:
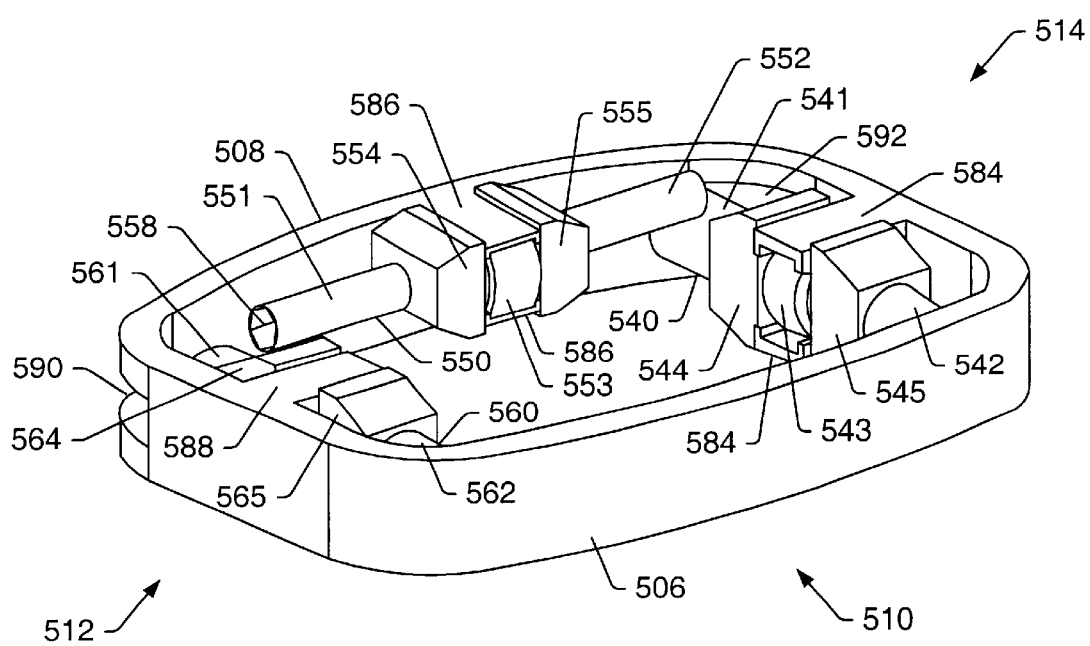
FIG. 39 depicts a perspective view of the bracket assembly of the fusion device of FIG. 38.

Turnbuckles 540, 550, and 560 may still further include indentations (indentation 558 of second turnbuckle 550 is visible in FIG. 39). The indentations may be configured to receive the tip of an adjusting tool (not shown). The adjusting tool may be a screwdriver. In a preferred embodiment, the adjusting tool is an allen wrench. Bracket assembly 506 preferably contains fenestrations 590 and 592 to facilitate access of the adjusting tool to the indentations. The adjusting tool may be used to rotate the turnbuckles. Rotation of first turnbuckle 540 in a first angular direction may cause cam blocks 544 and 545 to move away from each other; rotation of first turnbuckle 540 in an angular direction opposite the first angular direction may cause cam blocks 544 and 545 to move toward each other. Rotation of second turnbuckle 550 in a second angular direction may cause cam blocks 554 and 555 to move away from each other; rotation of second turnbuckle 550 in an angular direction opposite the second angular direction may cause cam blocks 554 and 555 to move toward each other. Rotation of third turnbuckle 560 in a third angular direction may cause cam blocks 564 and 565 to move away from each other; rotation of third turnbuckle 560 in an angular direction opposite the third angular direction may cause cam blocks 564 and 565 to move toward each other. The first, second, and third angular directions may be the same; alternatively, one of the angular directions may be opposite the other two angular directions.

As depicted in FIGS. 38–39, cam blocks 540, 550, and 560 and sloped tracks 520–531 may be configured such that motion of the cam blocks toward the edges of the engaging plates causes the height between the engaging plates to increase. The cam blocks and sloped tracks, however, may be configured such that motion of the cam blocks away from the edges of the engaging plates causes the height between the engaging plates to increase.

The turnbuckles in fusion device 500 may be positioned such that distances between engaging plates 502 and 504 along first side edge 512 and along second side edge 514 may be varied substantially independently to maintain a substantially natural lateral alignment. The turnbuckles in fusion device 500 may also be positioned such that distances between engaging plates 502 and 504 along anterior edge 508 and posterior edge 510 be varied substantially independently to maintain a substantially natural lordosis. In addition, slopes of upper and lower surfaces of the cam blocks may be unequal such that distances between engaging plates 502 and 504 along first side edge 512 and second side edge 514 may vary between anterior edge 508 and posterior edge 510 to maintain a substantially natural lateral alignment and such that distances between engaging plates 502 and 504 along anterior edge 508 and posterior edge 510 may vary between first side edge 512 and second side edge 514 to maintain a substantially natural lordosis.

Figure 40:
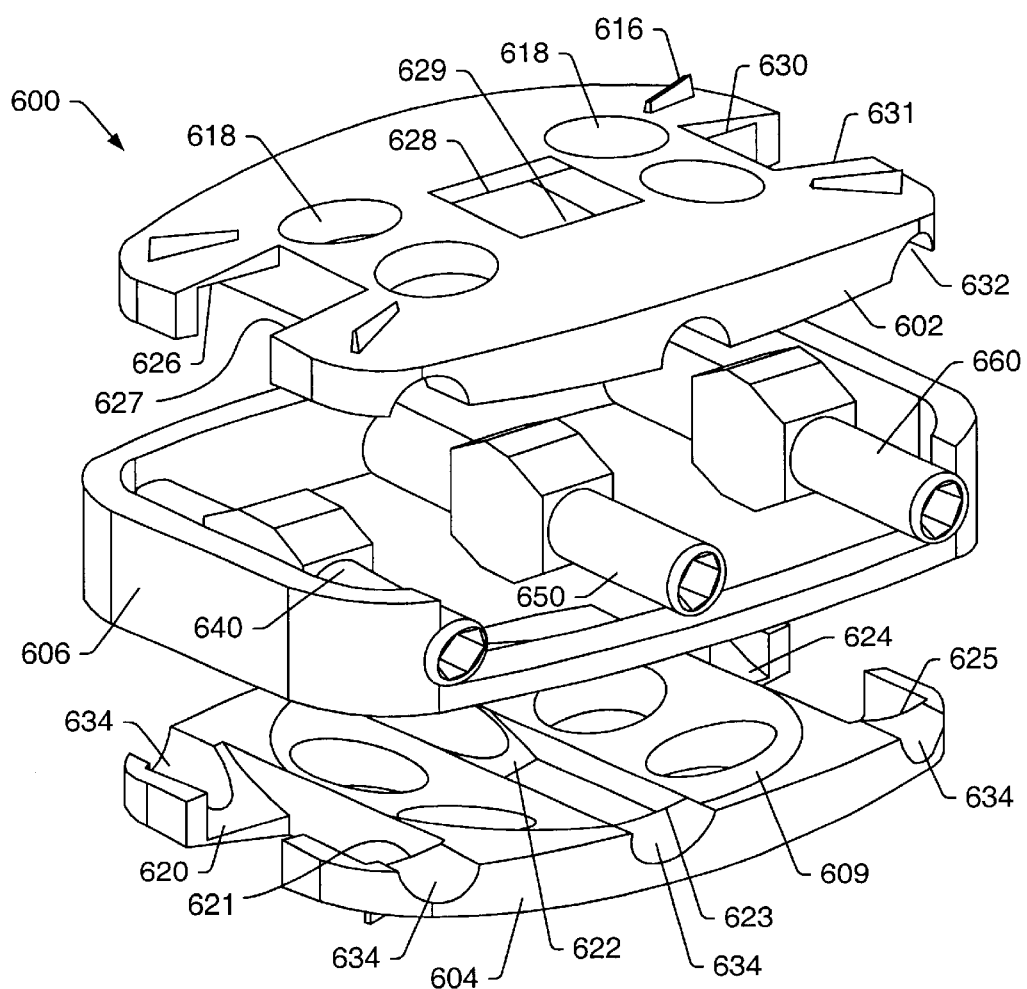
FIG. 40 depicts an exploded view of a fusion device including three substantially parallel screws.

An alternate embodiment of an interbody fusion device is depicted in an exploded view in FIG. 40. Interbody fusion device 600 preferably includes engaging plates 602 and 604 and bracket assembly 606. Engaging plates 602 and 604 and bracket assembly 606 may be formed of titanium, stainless steel, polymer, ceramic, composite material, or any other biocompatible material. Engaging plates 602 and 604 may include protrusions 616 and openings 618. Bracket assembly 606 (depicted in perspective view in FIG. 41) preferably includes an alignment device for changing a height between engaging plates 602 and 604. In an embodiment, the alignment device includes first screw 640 positioned substantially parallel to and substantially adjacent second side edge 614; second screw 650 positioned substantially parallel to and substantially centered between first side edge 612 and second side edge 614; and third screw 660 positioned substantially parallel to and substantially adjacent first side edge 612. Inner surfaces 609 of engaging plate 604 (FIG. 40) and the inner surface of engaging plate 602 (not readily visible in FIG. 40) include arcuate grooves 634 and 632, respectively, which correspond to the curvature of screws 640, 650, and 660. Bracket assembly 606 may include support portion 607 (FIG. 41) to support the ends of the screws. Support portion 607 may include arcuate grooves (not readily visible) corresponding to the curvature of screws 640, 650, and 660.

Threaded portion 641 of first screw 640 is preferably threaded in a first direction. Threaded portion 651 of second screw 650 is preferably threaded in a second direction. Threaded portion 661 of third screw 660 is preferably threaded in a third direction. Threaded portions 641, 651, and 661 may be threaded in the same direction; alternatively, one of the threaded portions may be threaded in a direction opposite the direction of the other two threaded portions.

First screw 640 is preferably coupled to cam block 644. Second screw 650 is preferably coupled to cam block 654. Third screw 660 is preferably coupled to cam block 664. Cam blocks 644, 654, and 664 preferably differ from the cam blocks of previously described embodiments substantially only in shape. Thus, cam blocks 644, 654, and 664 are preferably coupled to screws 640, 650, and 6600 in a manner similar to that depicted for cam block 260 and turnbuckle 250 (FIG. 29B). Cam blocks 644, 654, and 664 preferably include sloped upper and lower surfaces similar to the sloped upper and lower surfaces as previously described for cam blocks in other embodiments.

Inner surface 609 of engaging plate 604 preferably includes sloped tracks 620 and 621 corresponding to the slopes of the lower surfaces of cam block 644, sloped tracks 622 and 623 corresponding to the slopes of the lower surfaces of cam block 654, and sloped tracks 624 and 625 corresponding to the slopes of the lower surfaces of cam block 664. The inner surface of engaging plate 602 also preferably includes sloped tracks (the ends of which are visible in FIG. 40). Sloped tracks 626 and 627 preferably correspond to the slope of the upper surfaces of cam block 644. Sloped tracks 628 and 629 preferably correspond to the slope of the upper surfaces of cam block 654. Sloped tracks 630 and 631 preferably correspond to the slope of the upper surfaces of cam block 664.

Figure 41:
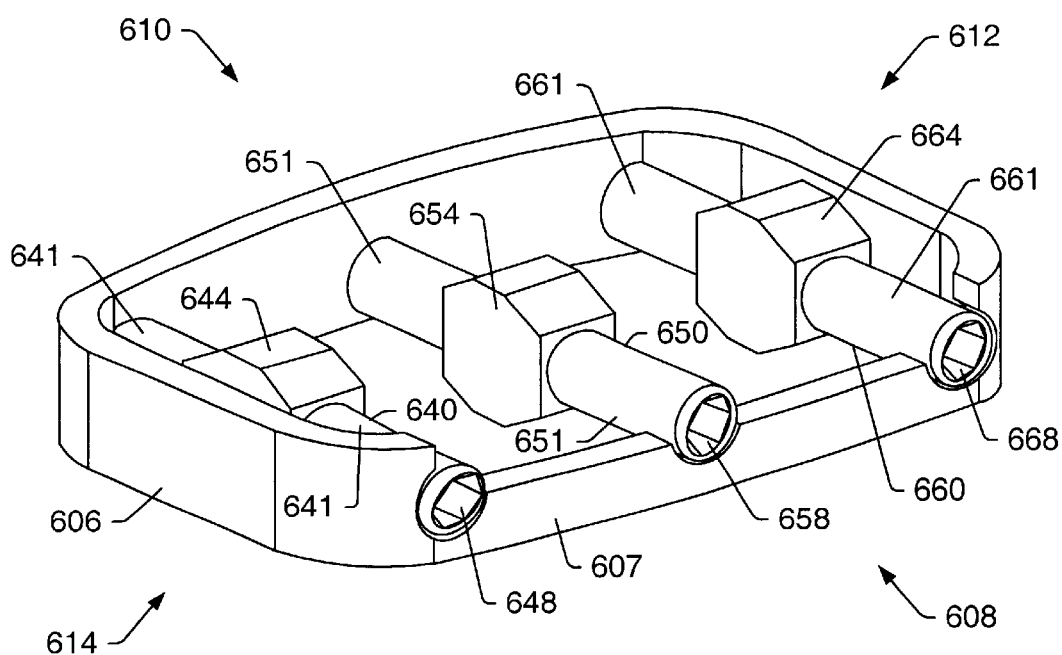
FIG. 41 depicts a perspective view of the bracket assembly of the fusion device of FIG. 40.

Screws 640, 650, and 660 may still further include indentations 648, 658, and 668 (FIG. 41). The indentations may be configured to receive the tip of an adjusting tool (not shown). The adjusting tool may be a screwdriver. In a preferred embodiment, the adjusting tool is an allen wrench. Rotation of first screw 640 in a first angular direction may cause cam block 644 to move toward anterior edge 608; rotation of first screw 640 in an angular direction opposite the first angular direction may cause cam block 644 to move toward posterior edge 610. Rotation of second screw 650 in a second angular direction may cause cam block 654 to move toward anterior edge 608; rotation of second screw 650 in an angular direction opposite the second angular direction may cause cam block 654 to move toward posterior edge 610. Rotation of third screw 660 in a third angular direction may cause cam block 664 to move toward anterior edge 608; rotation of third screw 660 in an angular direction opposite the third angular direction may cause cam block 664 to move toward posterior edge 610. The first, second, and third angular directions may be the same; alternatively, one of the first, second, and third angular directions may be opposite the other two of the first, second, and third angular directions.

As depicted in FIGS. 40–41, the cam blocks and sloped tracks are preferably configured such that motion of the cam blocks toward the edges of the engaging plates causes the height between the engaging plates to increase. The cam blocks and sloped tracks, however, may be configured such that motion of the cam blocks away from the edges of the engaging plates causes the height between the engaging plates to increase.

The screws in fusion device 600 may be positioned such that distances between engaging plates 602 and 604 along first side edge 612 and along second side edge 614 may be varied substantially independently to maintain a substantially natural lateral alignment. The screws in fusion device 600 may also be positioned such that distances between engaging plates 602 and 604 along anterior edge 608 and posterior edge 610 may be varied substantially independently to maintain a substantially natural lordosis. In addition, slopes of upper and lower surfaces of the cam blocks may be unequal such that distances between engaging plates 602 and 604 along first side edge 612 and second side edge 614 may vary between anterior edge 608 and posterior edge 610 to maintain a substantially natural lateral alignment and such that distances between engaging plates 602 and 604 along anterior edge 608 and posterior edge 610 may vary between first side edge 612 and second side edge 614 to maintain a substantially natural lordosis.

Figure 42:
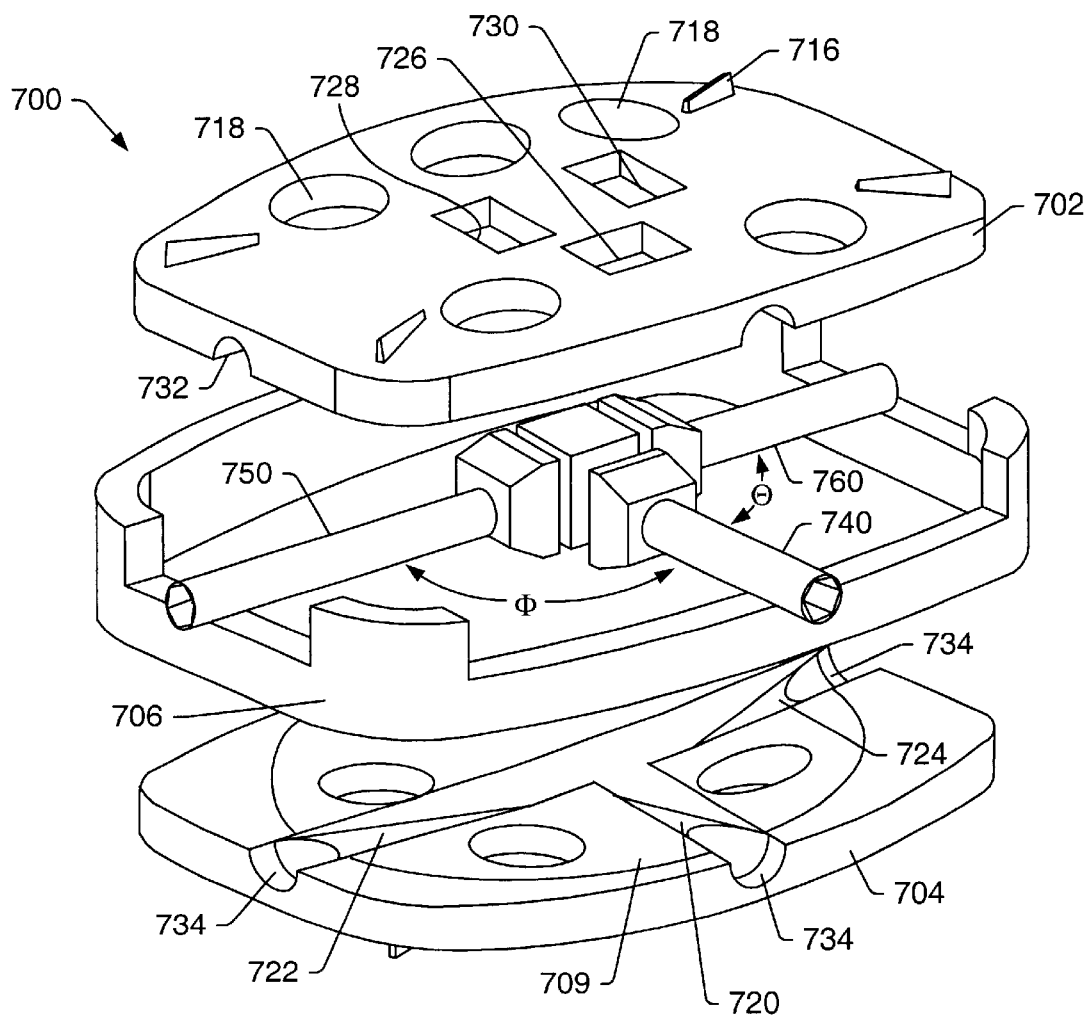
FIG. 42 depicts an exploded view of a fusion device including three non-parallel screws.

An alternate embodiment of an interbody fusion device is depicted in an exploded view in FIG. 42. Interbody fusion device 700 preferably includes engaging plates 702 and 704 and bracket assembly 706. Engaging plates 702 and 704 and bracket assembly 706 may be formed of titanium, stainless steel, polymer, ceramic, composite material, or any other biocompatible material. Engaging plates 702 and 704 may include protrusions 716 and openings 718. Bracket assembly 706 (depicted in perspective view in FIG. 43A) preferably includes an alignment device for changing a height between engaging plates 702 and 704. In an embodiment, the alignment device includes first screw 740, positioned substantially parallel to and substantially centered between first side edge 712 and second side edge 714; second screw 750 positioned at a first angle Φ (FIG. 42) with respect to first screw 740; and third screw 760 positioned at a second angle θ to first screw 740. In the embodiment pictured in FIGS. 42 and 43A, Φ=90° and θ=90°, such that second screw 750 and third screw 760 are preferably positioned substantially parallel to and substantially centered between anterior edge 708 and posterior edge 710 (FIG. 43A) and such that second screw 750 and third screw 760 preferably share a common axis of rotation. The alignment device further includes stationary block 790 to maintain the spatial relationship between screws 740, 750, and 760. In an alternate embodiment, Φ=90° and θ>90°. In a further alternate embodiment, Φ>90° and θ=90°. In a further alternate embodiment still, Φ>90° and θ>90°. In another embodiment, first screw 740 may be positioned other than parallel to and centered between opposite edges of the fusion device, screws 750 and 760 being positioned at angles Φ and θ, respectively, with respect to first screw 740.

The inner surfaces of engaging plates 702 and 704 preferably include arcuate grooves 732 and 734 (FIG. 42), respectively, which correspond to the curvature of screws 740, 750, and 760. Bracket assembly 706 preferably includes support portions 707 (FIG. 43A) to support the ends of the screws. Support portions 707 preferably include arcuate grooves (not readily visible in FIGS. 42 and 43A) corresponding to the curvature of screws 740, 750, and 760.

Threaded portion 741 of first screw 740 preferably is threaded in a first direction. Threaded portion 751 of second screw 750 preferably is threaded in a second direction. Threaded portion 761 of third screw 760 preferably is threaded in a third direction. Threaded portions 741, 751, and 761 may be threaded in the same direction; alternatively, one of the threaded portions may be threaded in a direction opposite the direction of the threading of the other two threaded portions. Screws 740, 750, and 760 may also include unthreaded portions (e.g., unthreaded portion 762 visible in FIG. 43A).

Figure 43A:
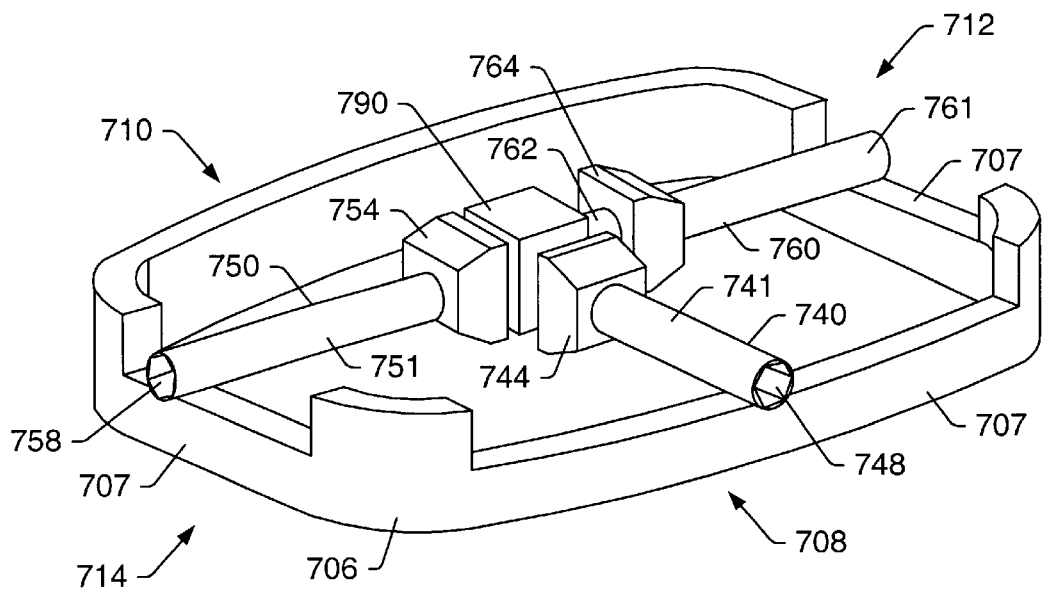
FIG. 43a depicts a perspective view of the bracket assembly of the fusion device of FIG. 42.
Figure 43B:
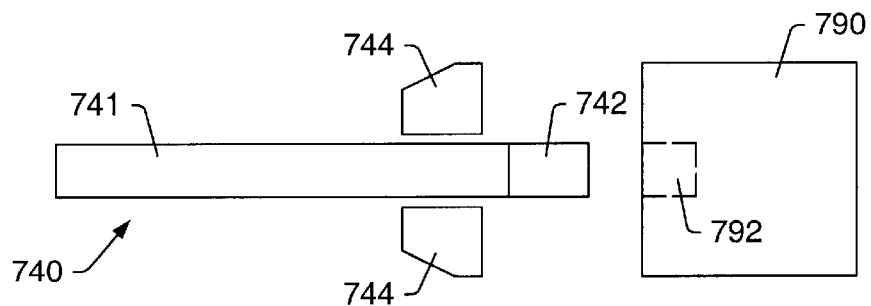
FIG. 43b depicts a cross-sectional view of a screw, a cam block, and the stationary block of FIG. 42.

FIG. 43B shows a detail of screw 740 including unthreaded portion 742. Unthreaded portion 742 may be inserted into cavity 792 (shown in phantom) in stationary block 790. Screw 740 thus may be free to rotate within stationary block 790. Stationary block 790 may be configured to be similarly coupled to screws 750 and 760. Engagement between stationary block 790 and screws 740, 750, and 760 preferably maintains coupling between screws 740, 750, and 760 and cam blocks 744, 754, and 764, respectively (that is, stationary block 790 preferably serves to stop motion of the cam blocks toward the interior of the fusion device such that the cam blocks are not separated from the screws). Stationary block 790 is pictured as a cube; however, stationary block 790 be of virtually any shape (e.g., cylinder, sphere, "T" shape similar to the positioning of screws 740, 750, and 760) that will maintain coupling between the screws and the cam blocks. Cam blocks 744, 754, and 764 are preferably coupled to screws 740, 750, and 760 in a manner similar to that depicted for cam block 236 and turnbuckle 226 (FIG. 29B). Cam blocks 744, 754, and 764 preferably include sloped upper and lower surfaces similar to the sloped upper and lower surfaces as previously described for cam blocks in other embodiments.

Returning to FIG. 42, inner surface 709 of engaging plate 704 preferably includes sloped tracks 720, 722, and 724 configured to correspond to the lower surfaces of cam blocks 744, 754, and 764, respectively. The inner surface of engaging plate 702 (not readily visible) also preferably includes sloped tracks 726, 728 and 730 (the ends of which are visible in FIG. 42). Sloped tracks 726, 728, and 730 are preferably configured to correspond to the upper surfaces of cam blocks 744, 754, and 764, respectively.

Screws 740, 750, and 760 may still further include indentations (e.g., indentations 748 and 758, visible in FIG. 43A). The indentations may be configured to receive the tip of an adjusting tool (not shown). The adjusting tool may be a screwdriver. In a preferred embodiment, the adjusting tool is an alien wrench. Rotation of first screw 740 in a first angular direction may cause cam block 744 to move toward anterior edge 708; rotation of first screw 740 in an angular direction opposite the first angular direction may cause cam block 744 to move away from anterior edge 708. Rotation of second screw 750 in a second angular direction may cause cam block 754 to move toward second side edge 714; rotation of second screw 750 in an angular direction opposite the second angular direction may cause cam block 754 to move away from second side edge 714. Rotation of third screw 760 in a third angular direction may cause cam block 764 to move toward first side edge 712; rotation of third screw 760 in an angular direction opposite the third angular direction may cause cam block 764 to move away from first side edge 712. The first, second, and third angular directions may be the same; alternatively, one of the first, second, and third angular directions may be opposite the other two angular directions.

Sloped tracks 720, 722, and 724 in lower engaging plate 704 and sloped tracks 726, 728, and 730 in upper engaging plate 702 are preferably configured to guide the motion of the cam blocks as the screws are rotated. As depicted in FIGS. 42 and 43A, the cam blocks and sloped tracks may be configured such that motion of the cam blocks toward the edges of the engaging plates causes the height between the engaging plates to increase. The cam blocks and sloped tracks, however, may be configured such that motion of the cam blocks away from the edges of the engaging plates causes the height between the engaging plates to increase.

The screws in fusion device 700 may be positioned such that distances between engaging plates 702 and 704 along first side edge 712 and along second side edge 714 may be varied substantially independently to maintain a substantially natural lateral alignment. The screws in fusion device 700 may also be positioned such that distances between engaging plates 702 and 704 along anterior edge 708 and posterior edge 710 may be varied substantially independently to maintain a substantially natural lordosis. In addition, slopes of upper and lower surfaces of the cam blocks may be unequal. Distances between engaging plates 702 and 704 along first side edge 712 and second side edge 714 may vary between anterior edge 708 and posterior edge 710 to maintain a substantially natural lateral alignment. Distances between engaging plates 702 and 704 along anterior edge 708 and posterior edge 710 may vary between first side edge 712 and second side edge 714 to maintain a substantially natural lordosis.

Figure 44:
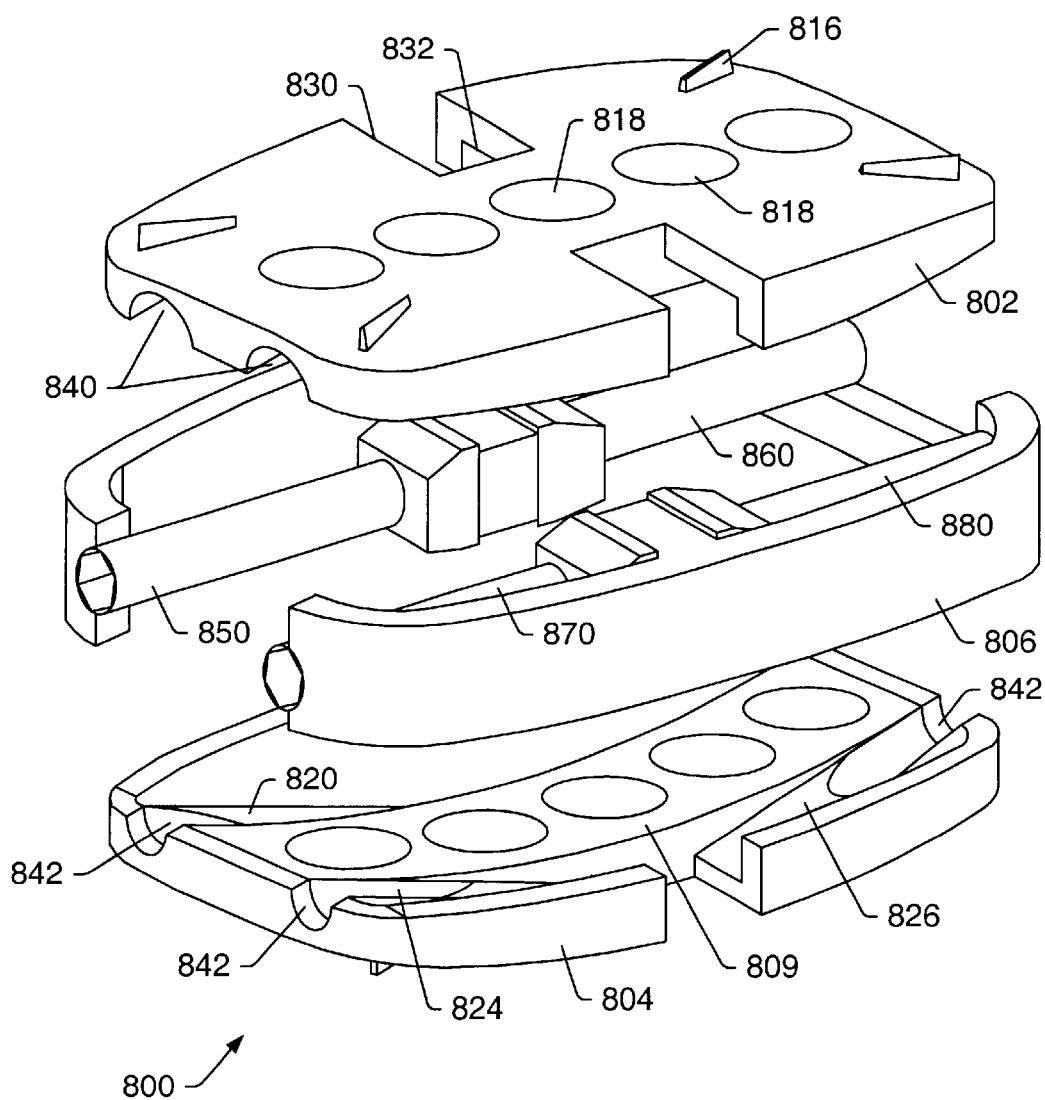
FIG. 44 depicts an exploded view of a fusion device including four screws oriented as two parallel pairs.

An alternate embodiment of an interbody fusion device including two parallel pairs of screws is depicted in an exploded view in FIG. 44. Interbody fusion device 800 preferably includes engaging plates 802 and 804 and bracket assembly 806. Engaging plates 802 and 804 and bracket assembly 806 may be formed of titanium, stainless steel, polymer, ceramic, composite material, or any other biocompatible material. Engaging plates 802 and 804 may include protrusions 816 and openings 818. Bracket assembly 806 (depicted in perspective view in FIG. 45) preferably includes an alignment device for changing a height between engaging plates 802 and 804. In an embodiment, the alignment device includes first screw 850 and second screw 860 having a common axis of rotation and positioned substantially parallel to and substantially adjacent posterior edge 810 and third screw 870 and fourth screw 880 having a common axis of rotation and positioned substantially parallel to and substantially adjacent anterior edge 808. The inner surfaces of engaging plates 802 and 804 preferably include arcuate grooves 840 and 842 (FIG. 44), respectively, which correspond to the curvature of screws 850, 860, 870, and 880. Bracket assembly 806 may include support portion 807 to support the ends of screws 860 and 880. Support portion 807 may include arcuate grooves corresponding to the curvature of screws 860 and 880 (not readily visible in FIGS. 44 and 45). Bracket assembly 806 preferably further includes ends 898 including arcuate grooves (not readily visible) corresponding to the curvature of screws 850 and 870.

Threaded portion 851 of first screw 850 may be threaded in a first direction. Threaded portion 861 of second screw 860 may be threaded in a second direction. Threaded portion 871 of third screw 870 may be threaded in a third direction. Threaded portion 881 of fourth screw 880 may be threaded in a fourth direction. Threaded portions 851, 861, 871, and 881 may be threaded in the same direction. Alternatively, one of the threaded portions may be threaded in a direction opposite the direction of the other three threaded portions. Alternatively, two of the threaded portions may be threaded in a direction opposite the direction of the other two threaded portions.

Screws 850, 860, 870, and 880 may include unthreaded portions (e.g., unthreaded portion 862 visible in FIG. 45) similar to unthreaded portion 742 of screw 740 (FIG. 43A). Lateral projections 894 and 896 may include substantially unthreaded openings, similar to unthreaded openings 792 of stationary block 790 (FIG. 43B), adapted to receive the unthreaded portions of the screws and in which the unthreaded portions of the screws are free to rotate.

First screw 851 is preferably configured to be coupled to cam block 854. Second screw 860 is preferably configured to be coupled to cam block 864. Third screw 870 is preferably configured to be coupled to cam block 874. Fourth screw 880 is preferably configured to be coupled to cam block 884. Cam blocks 854, 864, 874, and 884 are preferably coupled to screws 850, 860, 870 and 880 in a manner similar to that depicted for cam block 236 and turnbuckle 226 (FIG. 29B). Cam blocks 850, 860, 870, and 880 preferably include sloped upper and lower surfaces similar to the sloped upper and lower surfaces as previously described for cam blocks in other embodiments.

Returning to FIG. 42, inner surface 809 of engaging plate 804 preferably includes sloped track 820 configured to correspond to the lower surface of cam block 850; a sloped track (not visible) configured to correspond to the lower surface of cam block 860; sloped track 824 configured to correspond to the lower surface of cam block 870; and a sloped track 826 configured to correspond to the lower surface of cam block 880. The inner surface of engaging plate 802 preferably includes sloped tracks 830, 832, 834, and 836 (the ends of which are visible in FIG. 44). Sloped tracks 830, 832, 834, and 836 are preferably configured to correspond to the upper surfaces of cam blocks 850, 860, 870, and 880, respectively.

Figure 45:
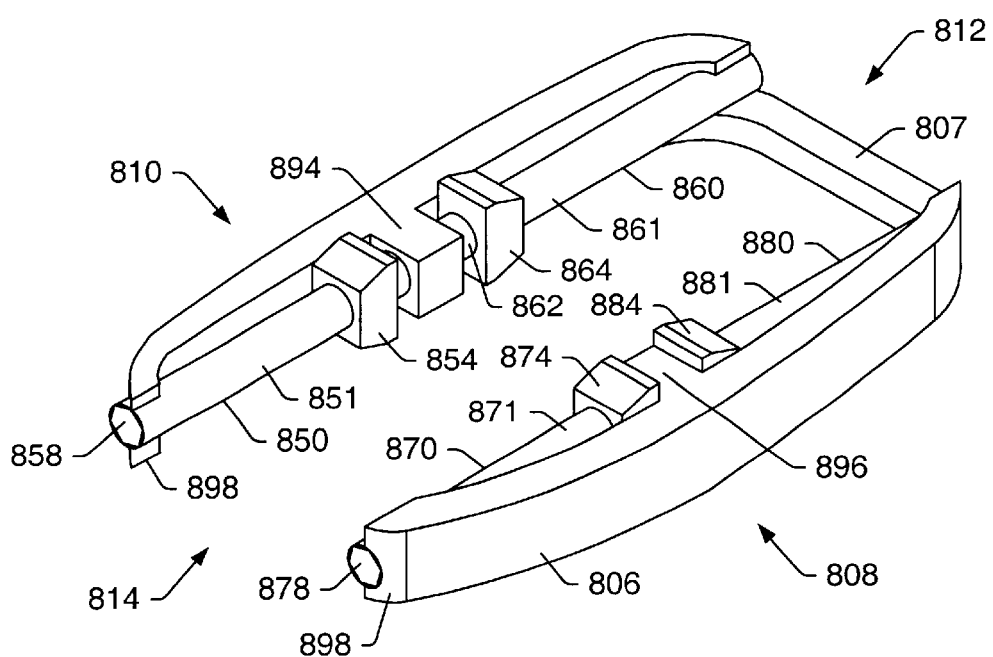
FIG. 45 depicts a perspective view of the bracket assembly of the fusion device of FIG. 42.

Screws 850, 860, 870, and 880 may still further include indentations (e.g., indentations 858 and 878, visible in FIG. 45). The indentations may be configured to receive the tip of an adjusting tool (not shown). The adjusting tool may be a screwdriver. In a preferred embodiment, the adjusting tool is an allen wrench. Rotation of first screw 850 in a first angular direction may cause cam block 854 to move toward second side edge 814; rotation of first screw 850 in an angular direction opposite the first angular direction may cause cam block 854 to move toward first side edge 812. Rotation of second screw 860 in a second angular direction may cause cam block 864 to move toward first side edge 812; rotation of second screw 860 in an angular direction opposite the second angular direction may cause cam block 864 to move toward second side edge 814. Rotation of third screw 870 in a third angular direction may cause cam block 874 to move toward second side edge 814; rotation of first screw 870 in an angular direction opposite the third angular direction may cause cam block 874 to move toward first side edge 812. Rotation of fourth screw 880 in a fourth angular direction may cause cam block 884 to move toward first side edge 812; rotation of fourth screw 880 in an angular direction opposite the fourth angular direction may cause cam block 884 to move toward second side edge 814. The first, second, third, and fourth angular directions may be the same. Alternatively, one of the first, second, third, and fourth angular directions may be opposite the other three of the first, second, third, and fourth angular directions. Alternatively, two of the first, second, third, and fourth angular directions may be opposite the other two of the first, second, third, and fourth angular directions.

As depicted in FIGS. 44–45, the cam blocks and sloped tracks are preferably configured such that motion of the cam blocks toward the edges of the engaging plates causes the height between the engaging plates to increase. The cam blocks and sloped tracks, however, may be configured such that motion of the cam blocks away from the edges of the engaging plates causes the height between the engaging plates to increase.

The screws in fusion device 800 may be positioned such that distances between engaging plates 802 and 804 along first side edge 812 and along second side edge 814 may be varied substantially independently to maintain a substantially natural lateral alignment. The screws in fusion device 800 may also be positioned such that distances between engaging plates 802 and 804 along anterior edge 808 and posterior edge 810 may be varied substantially independently to maintain a substantially natural lordosis. In addition, slopes of upper and lower surfaces of the cam blocks may be unequal such that distances between engaging plates 802 and 804 along first side edge 812 and second side edge 814 may vary between anterior edge 808 and posterior edge 810 to maintain a substantially natural lateral alignment and such that distances between engaging plates 802 and 804 along anterior edge 808 and posterior edge 810 may vary between first side edge 812 and second side edge 814 to maintain a substantially natural lordosis.

Figure 46:
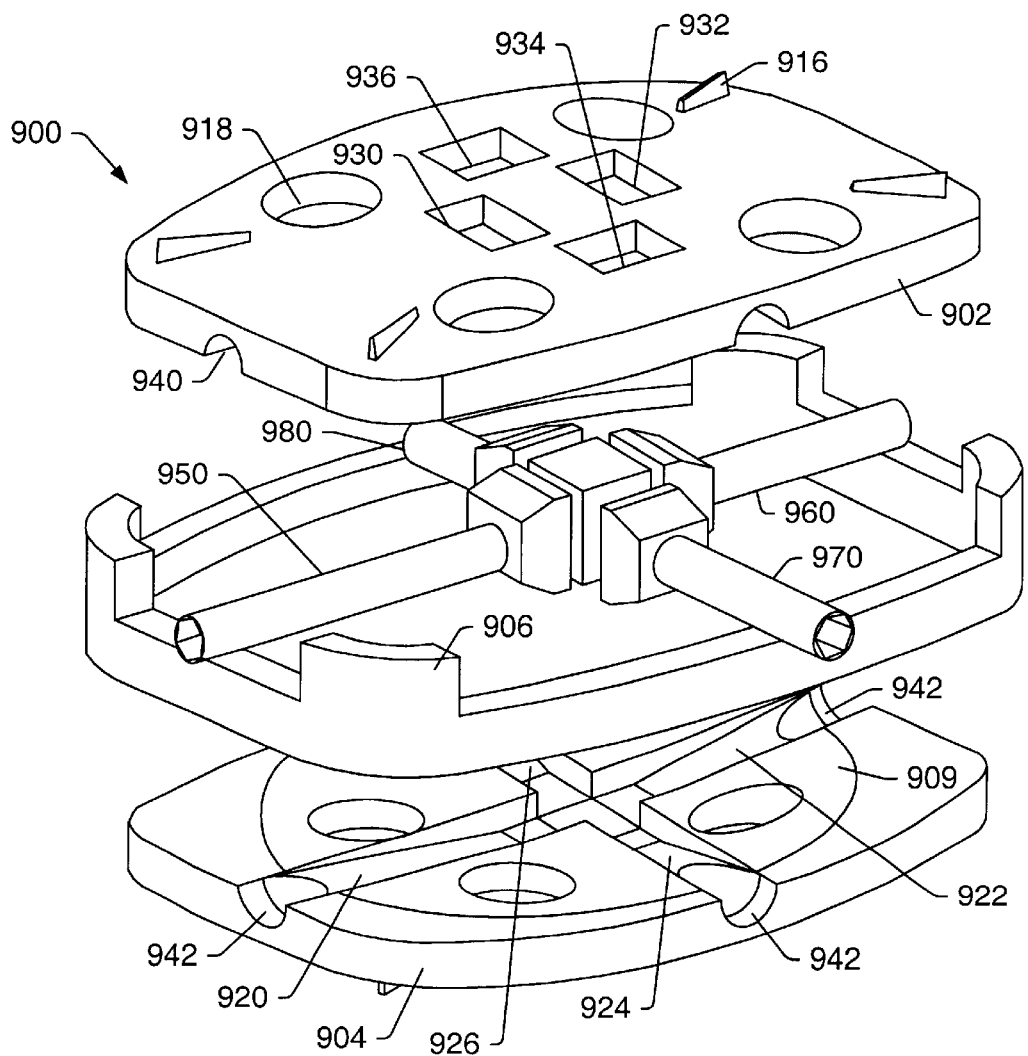
FIG. 46 depicts an exploded view of a fusion device including four screws oriented in a "+" configuration.

An alternate embodiment of an interbody fusion device including four screws oriented in a "+" configuration is depicted in an exploded view in FIG. 46. Interbody fusion device 900 preferably includes engaging plates 902 and 904 and bracket assembly 906. Engaging plates 902 and 904 and bracket assembly 906 may be formed of titanium, stainless steel, polymer, ceramic, composite material, or any other biocompatible material. Engaging plates 902 and 904 may include protrusions 916 and openings 918. Bracket assembly 906 (depicted in perspective view in FIG. 47) preferably includes an alignment device for changing a height between engaging plates 902 and 904. In an embodiment, the alignment device includes first screw 950 and second screw 960 having a common axis of rotation and positioned substantially parallel to and substantially centered between anterior edge 908 and posterior edge 910 and third screw 970 and fourth screw 980 having a common axis of rotation and positioned substantially parallel to and substantially centered between first side edge 912 and second side edge 914. The inner surfaces of engaging plates 902 and 904 preferably include arcuate grooves 940 and 942 (FIG. 46), respectively, which correspond to the curvature of screws 950, 960, 970, and 980. Bracket assembly 906 preferably includes support portions 907 to support the ends of screws 950, 960, 970, and 980. Support portions 907 may include arcuate grooves (not readily visible in FIGS. 46–47) corresponding to the curvature of screws 950, 960, 970, and 980.

Returning to FIG. 47, threaded portion 951 of first screw 950 preferably is threaded in a first direction. Threaded portion 961 of second screw 960 preferably is threaded in a second direction. Threaded portion 971 of third screw 970 preferably is threaded in a third direction. Threaded portion 981 of fourth screw 980 preferably is threaded in a fourth direction. Threaded portions 951, 961, 971, and 981 may be threaded in the same direction. Alternatively, one of the threaded portions may be threaded in a direction opposite the direction of the other three threaded portions. Alternatively, two of the threaded portions may be threaded in a direction opposite the direction of the other two threaded portions.

Screws 950, 960, 970, and 980 may include unthreaded portions 952, 962, 972, and 982, similar to unthreaded portion 730 of screw 728 (FIG. 43A). Stationary block 990 may include substantially unthreaded openings, similar to unthreaded openings 792 of stationary block 790 (FIG. 43A), adapted to receive the unthreaded portions of the screws and in which the unthreaded portions of the screws are free to rotate.

First screw 951 preferably is configured to be coupled to cam block 954. Second screw 960 preferably is configured to be coupled to cam block 964. Third screw 970 preferably is configured to be coupled to cam block 974. Fourth screw 980 preferably is configured to be coupled to cam block 984. Cam blocks 954, 964, 974, and 984 may be coupled to screws 950, 960, 970 and 980 in a manner similar to that depicted for cam block 236 and turnbuckle 226 (FIG. 29B). Cam blocks 950, 960, 970, and 980 preferably include sloped upper and lower surfaces similar to the sloped upper and lower surfaces as previously described for cam blocks in other embodiments.

Inner surface 909 of engaging plate 904 preferably includes sloped tracks 920, 922, 924, and 926 configured to correspond to the lower surface of cam blocks 950, 960, 970, and 980, respectively. The inner surface of engaging plate 902 preferably includes sloped tracks 930, 932, 934, and 936 (the ends of which are visible in FIG. 46) configured to correspond to the upper surfaces of cam blocks 950, 960, 970, and 980, respectively.

Figure 47:
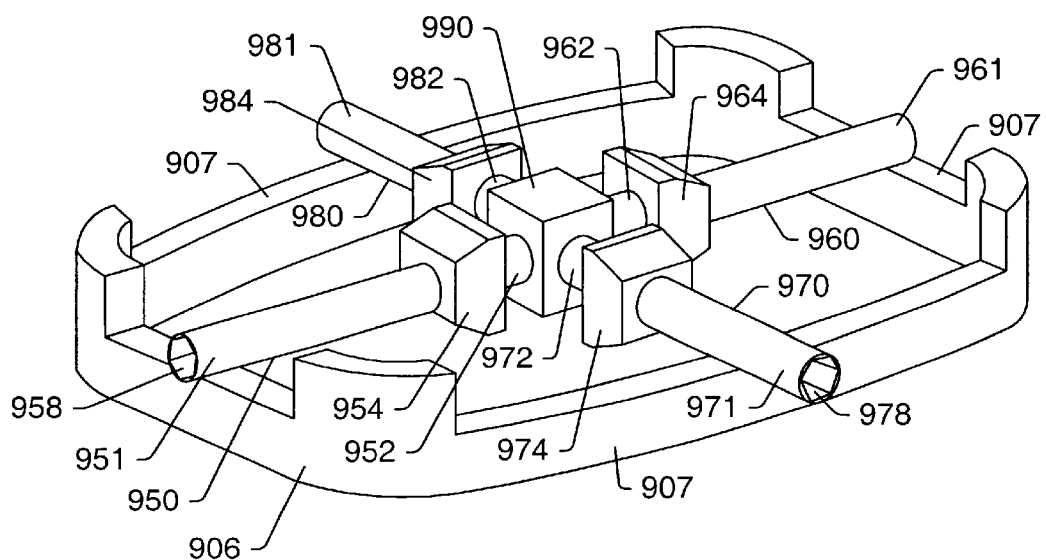
FIG. 47 depicts a perspective view of the bracket assembly of the fusion device of FIG. 46.

Screws 950, 960, 970, and 980 may still further include indentations (e.g., indentations 958 and 978, visible in FIG. 47). The indentations may be configured to receive the tip of an adjusting tool (not shown). The adjusting tool may be a screwdriver. In a preferred embodiment, the adjusting tool is an allen wrench. Rotation of first screw 950 in a first angular direction may cause cam block 954 to move away from stationary block 990; rotation of first screw 950 in an angular direction opposite the first angular direction may cause cam block 954 to move toward stationary block 990. Rotation of second screw 960 in a second angular direction may cause cam block 964 to move away from stationary block 990; rotation of second screw 960 in an angular direction oppo-site the second angular direction may cause cam block 964 to move toward stationary block 990. Rotation of third screw 970 in a third angular direction may cause cam block 974 to move away from stationary block 990; rotation of third screw 970 in an angular direction opposite the third angular direction may cause cam block 974 to move toward stationary block 990. Rotation of fourth screw 980 in a fourth angular direction may cause cam block 984 to move away from stationary block 990; rotation of second screw 980 in an angular direction opposite the fourth angular direction may cause cam block 984 to move toward stationary block 990. The first, second, third, and fourth angular directions may be the same. Alternatively, one of the first, second, third, and fourth angular directions may be opposite the other three of the first, second, third, and fourth angular directions. Alternatively, two of the first, second, third, and fourth angular directions may be opposite the other two of the first, second, third, and fourth angular directions.

As depicted in FIGS. 46–47, the cam blocks and sloped tracks are preferably configured such that motion of the cam blocks toward the edges of the engaging plates causes the height between the engaging plates to increase. The cam blocks and sloped tracks, however, may be configured such that motion of the cam blocks away from the edges of the engaging plates causes the height between the engaging plates to increase.

The screws in fusion device 900 may be positioned such that distances between engaging plates 902 and 904 along first side edge 912 and along second side edge 914 may be varied substantially independently to maintain a substantially natural lateral alignment. The screws in fusion device 900 may also be positioned such that distances between engaging plates 902 and 904 along anterior edge 908 and posterior edge 910 may be varied substantially independently to maintain a substantially natural lordosis. In addition, slopes of upper and lower surfaces of the cam blocks may be unequal such that distances between engaging plates 902 and 904 along first side edge 912 and second side edge 914 may vary between anterior edge 908 and posterior edge 910 to maintain a substantially natural lateral alignment and such that distances between engaging plates 902 and 904 along anterior edge 908 and posterior edge 910 may vary between first side edge 912 and second side edge 914 to maintain a substantially natural lordosis.

Figure 48:
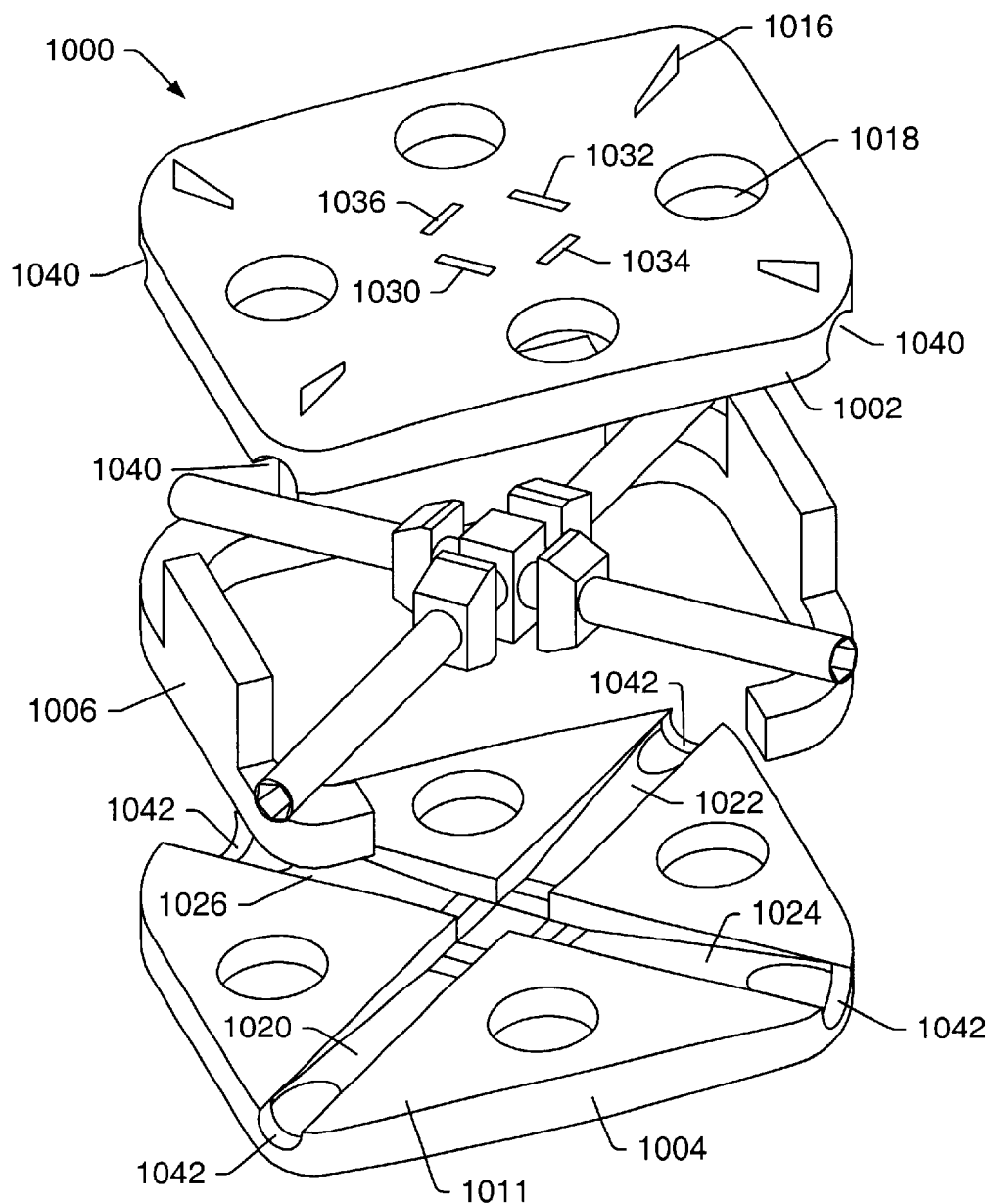
FIG. 48 depicts an exploded view of a fusion device including four screws oriented in an "×" configuration.

An alternate embodiment of an interbody fusion device including four screws oriented in an "×" configuration is depicted in an exploded view in FIG. 48. Interbody fusion device 1000 preferably includes engaging plates 1002 and 1004 and bracket assembly 1006. Engaging plates 1002 and 1004 and bracket assembly 1006 may be formed of titanium, stainless steel, polymer, ceramic, composite material, or any other biocompatible material. Engaging plates 1002 and 1004 may include protrusions 1016 and openings 1018. Bracket assembly 1006 (depicted in perspective view in FIG. 49) preferably includes an alignment device for changing a height between engaging plates 1002 and 1004. In an embodiment, the alignment device includes first screw 1050 and second screw 1060 having a common axis of rotation and positioned substantially along a diagonal connecting corner 1001 and corner 1005 of bracket assembly 1006. Preferably, bracket assembly 1006 further includes third screw 1070 and fourth screw 1080 having a common axis of rotation and positioned substantially along a diagonal connecting corner 1003 and corner 1007 of bracket assembly 1006. Inner surface 1009 of engaging plate 1004 (FIG. 48) and the inner surface of engaging plate 1002 (not readily visible in FIG. 48) preferably include arcuate grooves 1042 and 1040, respectively, which correspond to the curvature of screws 1050, 1060, 1070, and 1080. Bracket assembly 1006 preferably includes support portions 1098 (FIG. 49) to support the ends of screws 1050, 1060, 1070, and 1080. Support portions 1098 preferably include arcuate grooves (not readily visible) corresponding to the curvature of screws 1050, 1060, 1070, and 1080.

Threaded portion 1051 of first screw 1050 preferably is threaded in a first direction. Threaded portion 1061 of second screw 1060 preferably is threaded in a second direction. Threaded portion 1071 of third screw 1070 preferably is threaded in a third direction. Threaded portion 1081 of fourth screw 1080 preferably is threaded in a fourth direction. Threaded portions 1051, 1061, 1071, and 1081 may be threaded in the same direction. Alternatively, one of the threaded portions may be threaded in a direction opposite the direction of the other three threaded portions. Alternatively, two of the threaded portions may be threaded in a direction opposite the direction of the other two threaded portions.

Screws 1050, 1060, 1070, and 1080 may include unthreaded portions 1052, 1062, 1072, and 1082, similar to unthreaded portion 730 of screw 728 (FIG. 43A). Stationary block 1090 may include substantially unthreaded openings, similar to unthreaded openings 792 of stationary block 790 (FIG. 43B), adapted to receive the unthreaded portions of the screws and in which the unthreaded portions of the screws are free to rotate.

First screw 1051 is preferably configured to be coupled to cam block 1054. Second screw 1060 is preferably configured to be coupled to cam block 1064. Third screw 1070 is preferably configured to be coupled to cam block 1074. Fourth screw 1080 is preferably configured to be coupled to cam block 1084. Cam blocks 1054, 1064, 1074, and 1084 are preferably coupled to screws 1050, 1060, 1070 and 1080 in a manner similar to that depicted for cam block 236 and turnbuckle 226 (FIG. 29B). Cam blocks 1050, 1060, 1070, and 1080 preferably include sloped upper and lower surfaces similar to the sloped upper and lower surfaces as previously described for cam blocks in other embodiments.

Returning to FIG. 48, inner surface 1011 of engaging plate 1004 preferably includes sloped track 1020 configured to correspond to the lower surface of cam block 1050; sloped track 1022 configured to correspond to the lower surface of cam block 1060; sloped track 1024 configured to correspond to the lower surface of cam block 1070; and sloped track 1026 configured to correspond to the lower surface of cam block 1080. The inner surface (not readily visible) of engaging plate 1002 preferably includes sloped tracks 1030, 1032, 1034, and 1036 (the ends of which are visible in FIG. 48) configured to correspond to the upper surfaces of cam blocks 1050, 1060, 1070, and 1080, respectively.

Figure 49:
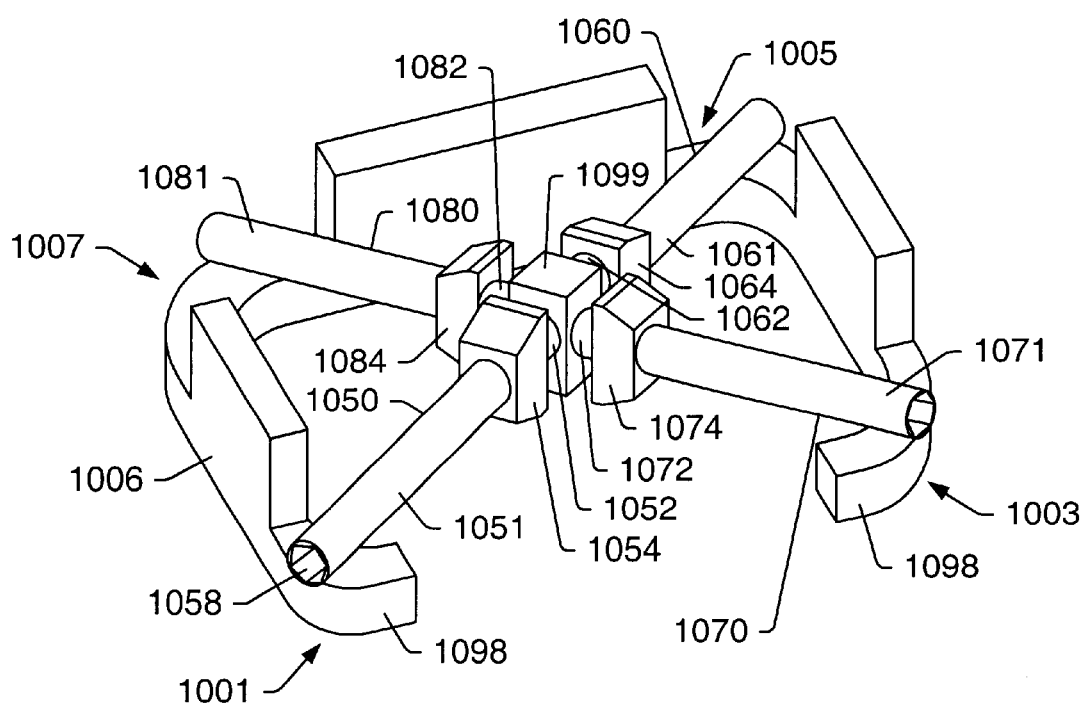
FIG. 49 depicts a perspective view of the bracket assembly of the fusion device of FIG. 48.
Figure 51A:
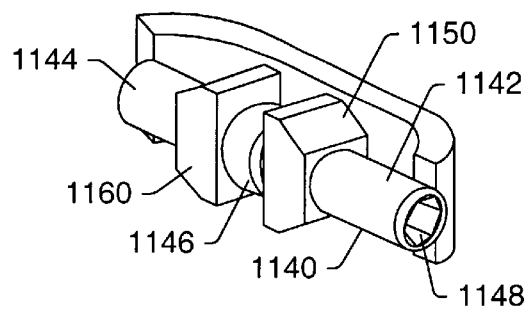
Figure 51B:
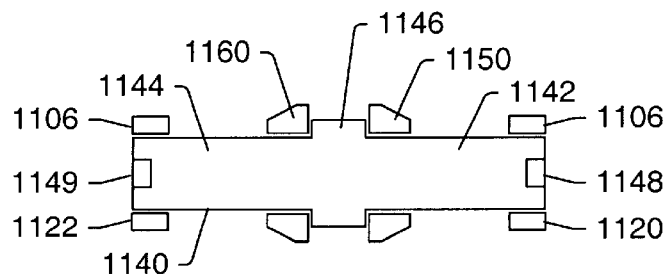
Figure 51C:
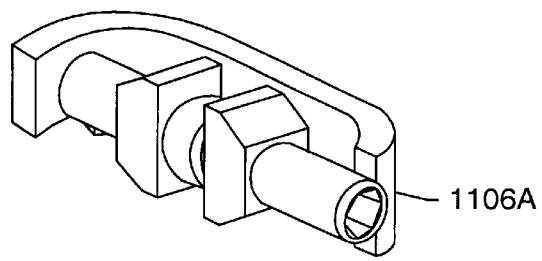
Figure 51D:
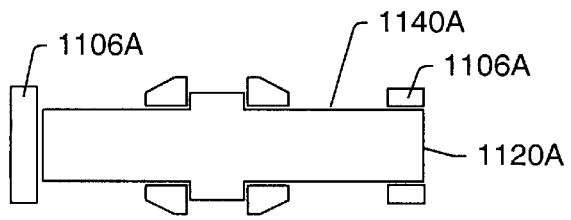

Screws 1050, 1060, 1070, and 1080 may still further include indentations (e.g., indentation 1058, visible in FIG. 49). The indentations may be configured to receive the tip of an adjusting tool (not shown). The adjusting tool may be a screwdriver. In a preferred embodiment, the adjusting tool is an alien wrench. Rotation of first screw 1050 in a first angular direction may cause cam block 1054 to move away from stationary block 1090; rotation of first screw 1050 in an angular direction opposite the first angular direction may cause cam block 1054 to move toward stationary block 1090. Rotation of second screw 1060 in a second angular direction may cause cam block 1064 to move away from stationary block 1090; rotation of second screw 1060 in an angular direction opposite the second angular direction may cause cam block 1064 to move toward stationary block 1090. Rotation of third screw 1070 in a third angular direction may cause cam block 1074 to move away from stationary block 1090; rotation of third screw 1070 in an angular direction opposite the third angular direction may cause cam block 1074 to move toward stationary block 1090. Rotation of fourth screw 1080 in a fourth angular direction may cause cam block 1084 to move away from stationary block 1090; rotation of second screw 1080 in an angular direction opposite the fourth angular direction may cause cam block 1084 to move toward stationary block 1090. The first, second, third, and fourth angular directions may be the same. Alternatively, one of the first, second, third, and fourth angular directions may be opposite the other three of the first, second, third, and fourth angular directions. Alternatively, two of the first, second, third, and fourth angular directions may be opposite the other two of the first, second, third, and fourth angular directions.

As depicted in FIGS. 48–49, the cam blocks and sloped tracks may be configured such that motion of the cam blocks toward the edges of the engaging plates causes the height between the engaging plates to increase. The cam blocks and sloped tracks, however, may be configured such that motion of the cam blocks away from the edges of the engaging plates causes the height between the engaging plates to increase.

The screws in fusion device 1000 may be positioned such that distances between engaging plates 1002 and 1004 along first side edge 1012 and along second side edge 1014 may be varied substantially independently to maintain a substantially natural lateral alignment. The screws in fusion device 1000 may also be positioned such that distances between engaging plates 1002 and 1004 along anterior edge 1008 and posterior edge 1010 may be varied substantially independently to maintain a substantially natural lordosis. In addition, slopes of upper and lower surfaces of the cam blocks may be unequal such that distances between engaging plates 1002 and 1004 along first side edge 1012 and second side edge 1014 may vary between anterior edge 1008 and posterior edge 1010 to maintain a substantially natural lateral alignment and such that distances between engaging plates 1002 and 1004 along anterior edge 1008 and posterior edge 1010 may vary between first side edge 1012 and second side edge 1014 to maintain a substantially natural lordosis.

Figure 52A:
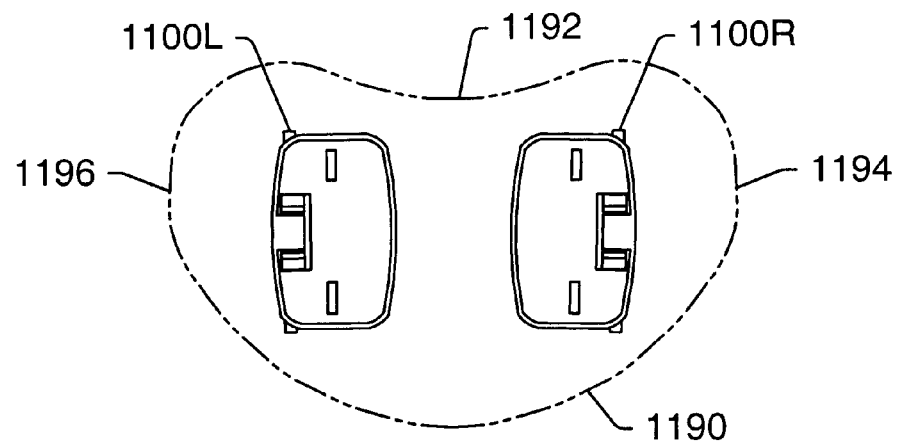

An alternate embodiment of an interbody fusion device is depicted in FIGS. 50–52. FIG. 50A depicts interbody fusion device 1100 in a lowered position. FIG. 50B depicts interbody fusion device 1100 in a raised position. FIG. 50C depicts interbody fusion device 1100 in an exploded view. Interbody fusion device 1100 preferably includes engaging plates 1102 and 1104 supported by bracket assembly 1106 (FIGS. 50A–50C). Engaging plates 1102 and 1104 and bracket assembly 1106 may be formed of titanium, stainless steel, polymer, ceramic, composite material, or any other biocompatible material. Engaging plates 1102 and 1104 may include protrusions 1116. Bracket assembly 1106 may include an alignment device for changing a distance between engaging plates 1102 and 1104. In an embodiment, the alignment device includes turnbuckle 1140 positioned between and substantially parallel to first elongated edge 1112 and second elongated edge 1114. Bracket assembly 1106 may include lateral projection 1124 extending into the interior of the bracket assembly and supporting turnbuckle 1140. Turnbuckle 1140 may include middle portion 1146 (FIG. 51A), similar to middle portion 543 of turnbuckle 540 (FIG. 38), disposed between the ends of the turnbuckle and having a diameter greater than a diameter of the threaded portions. Lateral projection 1124 (FIG. 50C) is preferably sized such that middle portion 1146 of turnbuckle 1140 is retained within the lateral projection while the turnbuckle is free to rotate within the lateral projection. Inner surface 1109 of engaging pates 1104 (FIG. 50C) and the inner surface of engaging plate 1102 (not readily visible in FIG. 50C) may include arcuate grooves 1128 and 1126, respectively, which correspond to the curvature of turnbuckle 1140.

As depicted in FIGS. 50A–50C, cam blocks 1150 and 1160 and sloped tracks 1130, 1132, 1134, and 1136 may be configured such that motion of the cam blocks toward first narrow edge 1108 and second narrow edge 1110 causes the distance between the engaging plates to increase. The cam blocks and sloped tracks, however, may be configured such that motion of the cam blocks toward the first and second narrow edges causes the distance between the engaging plates to decrease.

Figure 52B:
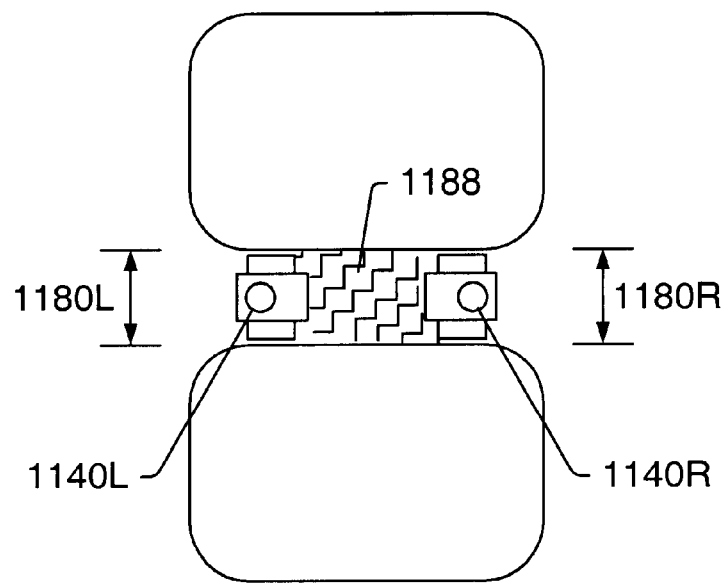

To install the fusion devices, a discectomy is preferably performed from an anterior approach. All cartilage and soft tissue are preferably removed from the vertebral endplate as would normally be done for placement for a femoral strut graft. Such a procedure is well within the knowledge of a skilled practitioner of the art. The engaging plates may be deployed in the disc space between adjacent vertebrae. FIG. 52B is a front (anterior) view of alignment devices 1100L and 1100R installed in the intervertebral disc space. Turnbuckles 1140L and 1140R may be rotated to achieve the desired distances 1180L and 1180R from an outer surface of an engaging plates to an outer surface of another engaging plate. The desired heights may be determined beforehand using x-ray techniques in which the side portions of the intervertebral disc space are examined. Bone graft material 1188 may be packed between alignment devices 1100L and 1100R to facilitate fusion of the vertebrae.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A spinal implant for facilitating fusion between neighboring vertebrae of a spine, comprising:
   a bracket assembly having a first side edge located opposite a second side edge;
   a pair of engaging plates configured to fit between and engage the vertebrae to maintain a disc space between the vertebrae during use, each engaging plate of the pair of engaging plates comprising a width substantially between the first side edge and the second side edge, and wherein an engaging plate of the pair of engaging plates is configured to move relative to the bracket assembly;
   a first alignment device positionable between engaging plates of the pair of engaging plates and coupled to the bracket assembly, wherein activation of the first alignment device moves an engaging plate of the pair of engaging plates relative to the bracket assembly such that a first posterior height of the pair of engaging plates adjacent the first side edge increases and such that a first anterior height of the pair of engaging plates adjacent the first side edge increases;
   a second alignment device positionable between the engaging plates of the pair of engaging plates and coupled to the bracket assembly, wherein activation of the second alignment device moves an engaging plate of the pair of engaging plates relative to the bracket assembly such that a second posterior height of the pair of engaging plates adjacent the second side edge increases and such that a second anterior height of the pair of engaging plates adjacent the second side edge increases; and
   wherein the first alignment device and the second alignment device are independently operable during use to establish a desired separation between the vertebrae.

2. The spinal implant of claim 1, wherein an anterior height of the pair of engaging plates varies between a first location proximate the first side edge and a second location proximate the second side edge, and wherein a posterior height of the pair of engaging plates varies between a third location proximate the first side edge and a fourth location proximate the second side edge.

3. The spinal implant of claim 1, wherein an engaging plate of the pair of engaging plates comprises a protrusion, the protrusion configured to extend into a vertebra of the neighboring vertebrae during use.

4. The spinal implant of claim 1, further comprising a track in a first engaging plate of the pair of engaging plates, wherein a portion of the first alignment device couples to the track.

5. The spinal implant of claim 1, wherein the track comprises a sloped surface, and wherein the first alignment device comprises a sloped surface that fits within the track.

6. The spinal implant of claim 5, wherein movement of the sloped surface of the first alignment device on the sloped track changes a height of the pair of engaging plates.

7. The spinal implant of claim 1, wherein an engaging plate of the pair of engaging plates comprises biocompatible metal.

8. The spinal implant of claim 1, wherein an engaging plate of the pair of engaging plates comprises biocompatible ceramic.

9. The spinal implant of claim 1, wherein an engaging plate of the pair of engaging plates comprises biocompatible polymer.

10. The spinal implant of claim 1, further comprising bone graft material.

11. The spinal implant of claim 10, wherein the bone graft material is positioned between the engaging plates of the pair of engaging plates.

12. The spinal implant of claim 11, further comprising a retaining plate positioned between the engaging plates of the pair of engaging plates to keep the bone graft material within the spinal implant.

13. The spinal implant of claim 1, further comprising openings in an engaging plate of the pair of engaging plates.

14. The spinal implant of claim 13, further comprising bone graft material positioned between engaging plates of the pair of engaging plates.

15. The spinal implant of claim 1, further comprising openings through an engaging plate of the pair of engaging plates, and wherein an area of the openings is greater than about fifty percent of the total surface area of an outer surface of the engaging plate.

16. The spinal implant of claim 1, wherein the bracket assembly supports the first alignment device.

17. The spinal implant of claim 16, wherein the bracket assembly comprises grooves configured to conform to a curvature of the first alignment device.

18. The spinal implant of claim 1, wherein an engaging plate of the pair of engaging plates comprises a groove configured to conform to a curvature of the first alignment device.

19. A spinal implant for facilitating a fusion between neighboring vertebrae of a spine, comprising:

a bracket assembly having a first side edge located opposite a second side edge;

a pair of engaging plates adapted to fit between and engage the vertebrae to maintain a disc space between the vertebrae during use, each engaging plate of the pair of engaging plates comprising an inner surface, wherein an engaging plate of the pair of engaging plates is configured to move relative to the bracket assembly;

a first pair of cam blocks configured to be coupled to inner surfaces of engaging plates of the pair of engaging plates during use;

a second pair of cam blocks configured to be coupled to the inner surfaces of the engaging plates of the pair of engaging plates during use;

a first member coupled to the first pair of cam blocks and to the bracket assembly adjacent the first side edge, wherein the first member is configured such that rotation of the first member in a first direction moves the first pair of cam blocks such that a first posterior height of the pair of engaging plates adjacent the first side edge is increased and such that a first anterior height of the pair of engaging plates adjacent the first side edge is increased; and a second member coupled to the second pair of cam blocks and to the bracket assembly adjacent the second side edge, wherein the second member is configured such that rotation of the second member in a second direction moves the second pair of cam blocks such that a second posterior height of the pair of engaging plates adjacent the second side edge is increased and such that a second anterior height of the pair of engaging plates adjacent the second side edge is increased.

20. The spinal implant of claim 19, wherein a posterior height of the pair of engaging plates varies between a first location proximate the first side edge and a second location proximate the second side edge such that the posterior height ranges between about a height of the pair of engaging plates at the first location and about a height of the pair of engaging plates at the second location.

21. The spinal implant of claim 19, wherein an anterior height of the pair of engaging plates varies between a first location proximate the first side edge and a second location proximate the second side edge such that the anterior height ranges from between about a height of the pair of engaging plates at the first location and a height of the pair of engaging plates at the second location.

22. The spinal implant of claim 19, wherein a posterior height of the pair of engaging plates varies between a first location proximate the first side edge and a second location proximate the second side edge such that the posterior height ranges between about a height of the pair of engaging plates at the first location and about a height of the pair of engaging plates at the second location and wherein an anterior height varies between a third location proximate the first side edge and a fourth location proximate the second side edge such that the anterior height ranges between about a height of the pair of engaging plates at the third location and about a height of the pair of engaging plates at the fourth location.

23. The spinal implant of claim 19, wherein the first member is oriented substantially parallel to and substantially adjacent the first side edge of the bracket assembly, and wherein the second member is oriented substantially parallel to and substantially adjacent the second side edge of the bracket assembly.

24. The spinal implant of claim 19, wherein the bracket assembly supports the first member and the second member.

25. The spinal implant of claim 24, wherein the bracket assembly comprises ends including arcuate grooves configured to conform to a curvature of the first member.

26. The spinal implant of claim 19, wherein the inner surfaces of the engaging plates of the pair of engaging plates include arcuate grooves configured to conform to a curvature of the first member.

27. The spinal implant of claim 19, wherein the inner surface of each of the engaging plates of the pair of engaging plates comprises a sloped track, and wherein the first pair of cam blocks couple to the sloped tracks such that rotation of the first member moves the first pair of cam blocks to adjust the first anterior height of the pair of engaging plates and the first posterior height of the pair of engaging plates during use.

28. The spinal implant of claim 19, wherein the inner surface of each of the engaging plates of the pair of engaging plates comprises a sloped track, wherein the first pair of cam blocks couple to the sloped tracks, and wherein each cam block of the first pair of cam blocks includes a first surface sloped to substantially conform to the sloped tracks in the inner surfaces of the engaging plates of the pair of engaging plates.

29. The spinal implant of claim 28, wherein the first surface of each cam block of the first pair of cam blocks and the sloped tracks in the inner surfaces of the engaging plates of the pair of engaging plates are configured such that movement of the cam blocks of the first pair of cam blocks toward each other increases the first anterior height of the pair of engaging plates and the first posterior height of the pair of engaging plates during use.

30. The spinal implant of claim 25, wherein the first surface of each cam block of the first pair of cam blocks and the sloped tracks in the inner surfaces of the engaging plates of the pair of engaging plates are configured such that movement of the cam blocks of the first pair of cam blocks toward each other decreases the first anterior height of the pair of engaging plates and the first posterior height of the pair of engaging plates during use.

31. The spinal implant of claim 19, wherein the spinal implant comprises a biocompatible material.

32. The spinal implant of claim 19, wherein outer surfaces of the engaging plates of the pair of engaging plates are substantially planar so as to inhibit subsidence of the vertebrae during use.

33. The spinal implant of claim 19, wherein the engaging plates of the pair of engaging plates comprise a plurality of openings to allow bone growth to occur through the engaging plates during use.

34. The spinal implant of claim 19, further comprising bone graft material packed between the engaging plates of the pair of engaging plates, wherein the engaging plates comprise a plurality of openings to allow bone growth to occur through the engaging plates during use.

35. The spinal implant of claim 19, further comprising protrusions extending from at least one of the engaging plates of the pair of engaging plates for enhancing engagement between a vertebra of the neighboring vertebrae and the spinal implant during use.

36. The spinal implant of claim 19, further comprising protrusions extending from at least one of the engaging plates of the pair of engaging plates for enhancing engagement between the spine and the spinal implant during use, the protrusions being adapted to extend into the spine.

37. The spinal implant of claim 19, further comprising bone graft material and a retaining plate, the bone graft material being packed between the engaging plates of the pair of engaging plates, the retaining plate being configured to keep the bone graft material between the engaging plates during use.

38. The spinal implant of claim 19, wherein at least one engaging plate of the pair of engaging plates comprises a face and openings extending through the face to allow bone growth to occur through the at least one engaging plate during use, the openings having a total area that is greater than about fifty percent of a total surface area of the face.

39. The spinal implant of claim 19, wherein at least one engaging plate of the pair of engaging plates comprises a face and openings extending through the face to allow bone growth to occur through the engaging plate during use, the openings having a total area that is between about sixty percent and about eighty percent of a total surface area of the face.

40. The spinal implant of claim 19, wherein an end of the first member includes an indentation adapted to accept a tip of an adjusting tool that rotates the first member.

41. The spinal implant of claim 40, wherein the adjusting tool comprises a tool selected from the group consisting of screwdrivers and allen wrenches.

* * * * *